US012072335B2

(12) United States Patent
Carissimo et al.

(10) Patent No.: US 12,072,335 B2
(45) Date of Patent: Aug. 27, 2024

(54) METHOD OF EVALUATING PROGRESSION OF AN INFECTIOUS DISEASE AND/OR INFLAMMATORY DISEASE

(71) Applicant: Agency for Science, Technology and Research, Singapore (SG)

(72) Inventors: Guillaume Robert Carissimo, Singapore (SG); Immanuel Kwok Weng Han, Singapore (SG); Weili Xu, Singapore (SG); Lisa Fong Poh Ng, Singapore (SG); Laurent Renia, Singapore (SG); Anis Larbi, Singapore (SG); Lai Guan Ng, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 426 days.

(21) Appl. No.: 17/117,455

(22) Filed: Dec. 10, 2020

(65) Prior Publication Data
US 2022/0187296 A1   Jun. 16, 2022

(51) Int. Cl.
*G01N 33/569* (2006.01)
*A61K 49/00* (2006.01)
*G01N 33/50* (2006.01)

(52) U.S. Cl.
CPC ... *G01N 33/56972* (2013.01); *A61K 49/0004* (2013.01); *G01N 33/5094* (2013.01); *G01N 2333/165* (2013.01); *G01N 2800/26* (2013.01); *G01N 2800/50* (2013.01); *G01N 2800/52* (2013.01); *G01N 2800/56* (2013.01); *G01N 2800/60* (2013.01)

(58) Field of Classification Search
CPC ......... G01N 33/56972; G01N 33/5094; G01N 2333/165; G01N 2800/26; G01N 2800/60; A61K 49/0004
See application file for complete search history.

(56) References Cited

U.S. PATENT DOCUMENTS

2011/0207145 A1* 8/2011 Perez ................. G01N 33/5008
435/7.1

OTHER PUBLICATIONS

Morrissey et al. Emergence of Low-density Inflammatory Neutrophils Correlates to Hypercoagulable State and Disease Severity in COVID-19 Patients. MEDRxiv the Preprint Server for Health Sciences. doi 10.1101 2020.05.22.20106724. BMJ Yale. 43 pages (May 26, 2020).*

(Continued)

*Primary Examiner* — Gailene Gabel
(74) *Attorney, Agent, or Firm* — Kilpatrick Townsend & Stockton LLP

(57) ABSTRACT

There is provided a method of evaluating risk of severe outcome of an infectious disease and/or an inflammatory disease in a patient, the method comprising: determining/measuring the number of one or more immune cells selected from the group consisting of VD2 T cells, CD8 T cells, and immature neutrophils in a sample obtained from the patient, wherein the patient has an enhanced risk of severe infectious disease and/or inflammatory disease outcome when: (i) the ratio of immature neutrophils to VD2 T cell is at least 2:1, and/or (ii) the ratio of immature neutrophils to CD8 T cell is at least 0.5:1. Also disclosed are method of treating a patient with a severe infectious disease and/or inflammatory disease and kit for use in methods thereof.

16 Claims, 34 Drawing Sheets

(56) References Cited

OTHER PUBLICATIONS

Figure 1A:
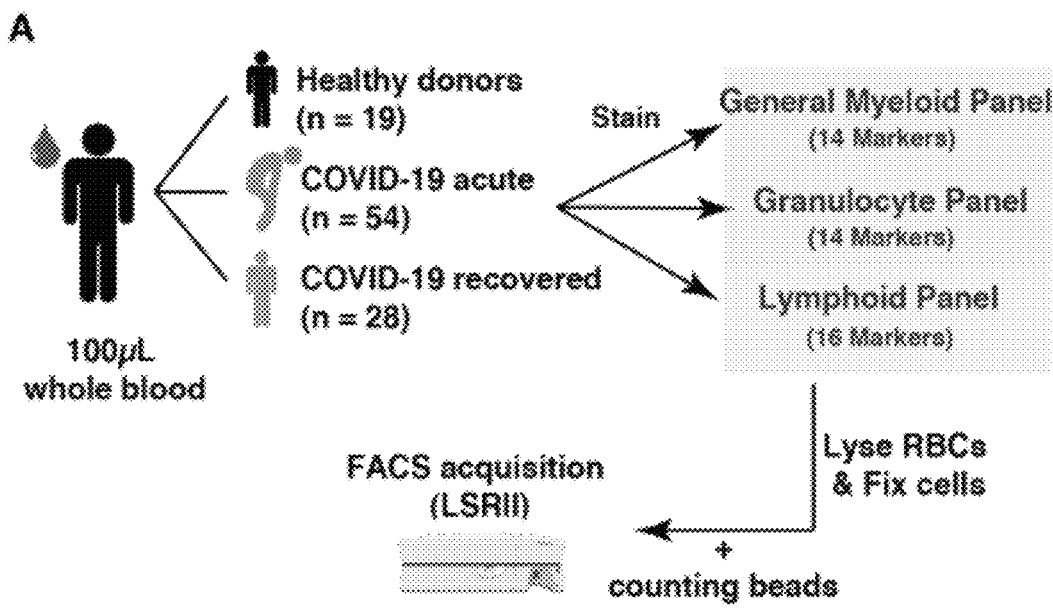

Mitra et al. Leukoerythroblastic reaction in a patient with COVID-19 infection Am J Hematol 95: 999-1000 (Mar. 9, 2020).*

Liu et al. Longitudinal characteristics of lymphocyte responses and cytokine profiles in the peripheral blood of SARS-Cov-2 infected patients. EBioMedicine 55. 10 pages (Apr. 18, 2020).*

Becton Dickinson. CD Marker Handbook pp. 1-6, 48 (2011).*

Caccamo, et al., "A. Differential requirements for antigen or homeostatic cytokines for proliferation and differentiation of human Vg9Vd2 naive, memory and effector T cell subsets", Eur J Immunol 35, 1764-1772, Apr. 19, 2005.

Michishita, et al., Age-associated alteration of gd T-cell repertoire and different profiles of activation induced death of Vd1 and Vd2 T cells, Int J Hematol 94, 230-240, Aug. 20, 2011.

Vasudev, e al., "A. g/d T cell subsets in human aging using the classical a/b T cell model", J Leukoc Biol 96, 647-655, Jun. 19, 2014.

Tan, et al., "Vd2+ and a/b T cells show divergent trajectories during human aging" Oncotarget 7, 44906-44918, Jun. 15, 2016.

Guan, W.-J., et al. "Clinical Characteristics of Coronavirus Disease 2019 in China", *The New England Journal of Medicine*, vol. 382, Issue No. 18, Feb. 28, 2020, pp. 1708-1720, DOI: 10.1056/NEJMoa2002032.

Wu, Z., et al. "Characteristics of and Important Lessons From the Coronavirus Disease 2019 (COVID-19) Outbreak in China: Summary of a Report of 72 314 Cases From the Chinese Center for Disease Control and Prevention", *JAMA*. vol. 323, Issue No. 13, Feb. 24, 2020, pp. 1239-1242, doi:10.1001/jama.2020.2648.

Wang, D., et al. "Clinical Characteristics of 138 Hospitalized Patients With 2019 Novel Coronavirus-Infected Pneumonia in Wuhan, China", *JAMA*. vol. 323, Issue No. 11, Feb. 7, 2020, pp. 1061-1069. doi:10.1001/jama.2020.1585.

Chen, N., et al. "Epidemiological and clinical characteristics of 99 cases of 2019 novel coronavirus pneumonia in Wuhan, China: a descriptive study", The Lancet, vol. 395, Issue No. 10223, Feb. 15, 2020, pp. 507-513, https://doi.org/10.1016/S0140-6736(20)30211-7.

Jose, R. J., et al. "COVID-19 cytokine storm: the interplay between inflammation and coagulation" *The Lancet. Respiratory medicine*, vol. 8, Issue No. 6, Apr. 27, 2020, pp. 1-2, https://doi.org/10.1016/S2213-2600(20)30216-2.

Chen, G., et al. "Clinical and immunological features of severe and moderate coronavirus disease 2019." *The Journal of clinical investigation*, vol. 130, Issue No. 5, May 1, 2020, pp. 2620-2629, doi: 10.1172/JCI137244.

Zheng, H. Y., et al. "Elevated exhaustion levels and reduced functional diversity of T cells in peripheral blood may predict severe progression in COVID-19 patients", Cellular & molecular immunology, vol. 17, Issue No. 5, Mar. 17, 2020, pp. 541-543, https://doi.org/10.1038/s41423-020-0401-3.

Qin, C., et al. "Dysregulation of Immune Response in Patients With Coronavirus 2019 (COVID-19) in Wuhan, China", *Clinical infectious diseases*: an official publication of the Infectious Diseases Society of America, vol. 71, Issue No. 15, Jul. 28, 2020, pp. 762-768, https://doi.org/10.1093/cid/ciaa248.

De Biasi, S., et al. "Marked T cell activation, senescence, exhaustion and skewing towards TH17 in patients with COVID-19 pneumonia", Nature communications, vol. 11, Issue No. 1, Jul. 6, 2020, pp. 1-17, https://doi.org/10.1038/s41467-020-17292-4.

Marini, O., et al., "Mature CD10+ and immature CD10— neutrophils present in G-CSF-treated donors display opposite effects on T cells", *Blood*, vol. 129, Issue No. 10, Mar. 9, 2017, pp. 1343-1356. https://doi.org/10.1182/blood-2016-04-713206.

Young, B. E. et al., "Immunological and Viral Correlates of COVID-19 Disease Severity: A Prospective Cohort Study of the First 100 Patients in Singapore", *Social Science Research Networ (SSRN Electronic Journal)*, Apr. 15, 2020, pp. 1-34, https://dx.doi.org/10.2139/ssrn.3576846.

Liu, J., et al. "Longitudinal characteristics of lymphocyte responses and cytokine profiles in the peripheral blood of SARS-CoV-2 infected patients", EBioMedicine, vol. 55, Issue No. 102763, Apr. 18, 2020, pp. 1-10, https://doi.org/10.1016/j.ebiom.2020.102763.

Lagunas-Rangel F. A., "Neutrophil-to-lymphocyte ratio and lymphocyte-to-C-reactive protein ratio in patients with severe coronavirus disease 2019 (COVID-19): A meta-analysis", *Journal of medical virology*, vol. 92, Issue No. 10, Oct. 1, 2020, pp. 1733-1734, https://doi.org/10.1002/jmv.25819.

Sánchez-Cerrillo, I., et al., "COVID-19 severity associates with pulmonary redistribution of CD1c+ DCs and inflammatory transitional and nonclassical monocytes", *The Journal of clinical investigation*, vol. 130, Issue No. 12, Dec. 1, 2020, pp. 6290-6300, https://doi.org/10.1172/JCI140335.

Morrissey, S., et al. "Emergence of Low-density Inflammatory Neutrophils Correlates with Hypercoagulable State and Disease Severity in COVID-19 Patients", *Cold Spring Harbor Laboratory Press*, May 26, 2020, pp. 1-43, doi.org/10.1101/2020.05.22.20106724.

Silvin, A., et al. "Elevated Calprotectin and Abnormal Myeloid Cell Subsets Discriminate Severe from Mild COVID-19", *Cell*, vol. 182, Issue No. 6, Sep. 17, 2020, 37 pages, https://doi.org/10.1016/j.cell.2020.08.002.

Zhang, D., et al. "COVID-19 infection induces readily detectable morphological and inflammation-related phenotypic changes in peripheral blood monocytes, the severity of which correlate with patient outcome", *Cold Spring Harbor Laboratory Press*, Mar. 24, 2020, pp. 1-17, https://doi.org/10.1101/2020.03.24.20042655.

Laggner, U., et al., "Identification of a novel proinflammatory human skin-homing Vγ9Vδ2 T cell subset with a potential role in psoriasis", *Journal of immunology*, vol. 187, Issue No. 5, Sep. 1, 2011, pp. 2783-2793, https://doi.org/10.4049/jimmunol.1100804.

Urboniene, D., et al., "Distribution of γδ and other T-lymphocyte subsets in patients with chronic obstructive pulmonary disease and asthma", *Respiratory medicine*, vol. 107, Issue No. 3, Mar. 2013, pp. 413-423, https://doi.org/10.1016/j.rmed.2012.11.012.

Li, J., et al., "Epidemiology of COVID-19: A systematic review and meta-analysis of clinical characteristics, risk factors, and outcomes", *Journal of medical virology*, vol. 93, Issue No. 3, Mar. 2021, pp. 1449-1458, https://doi.org/10.1002/jmv.26424.

\* cited by examiner

C

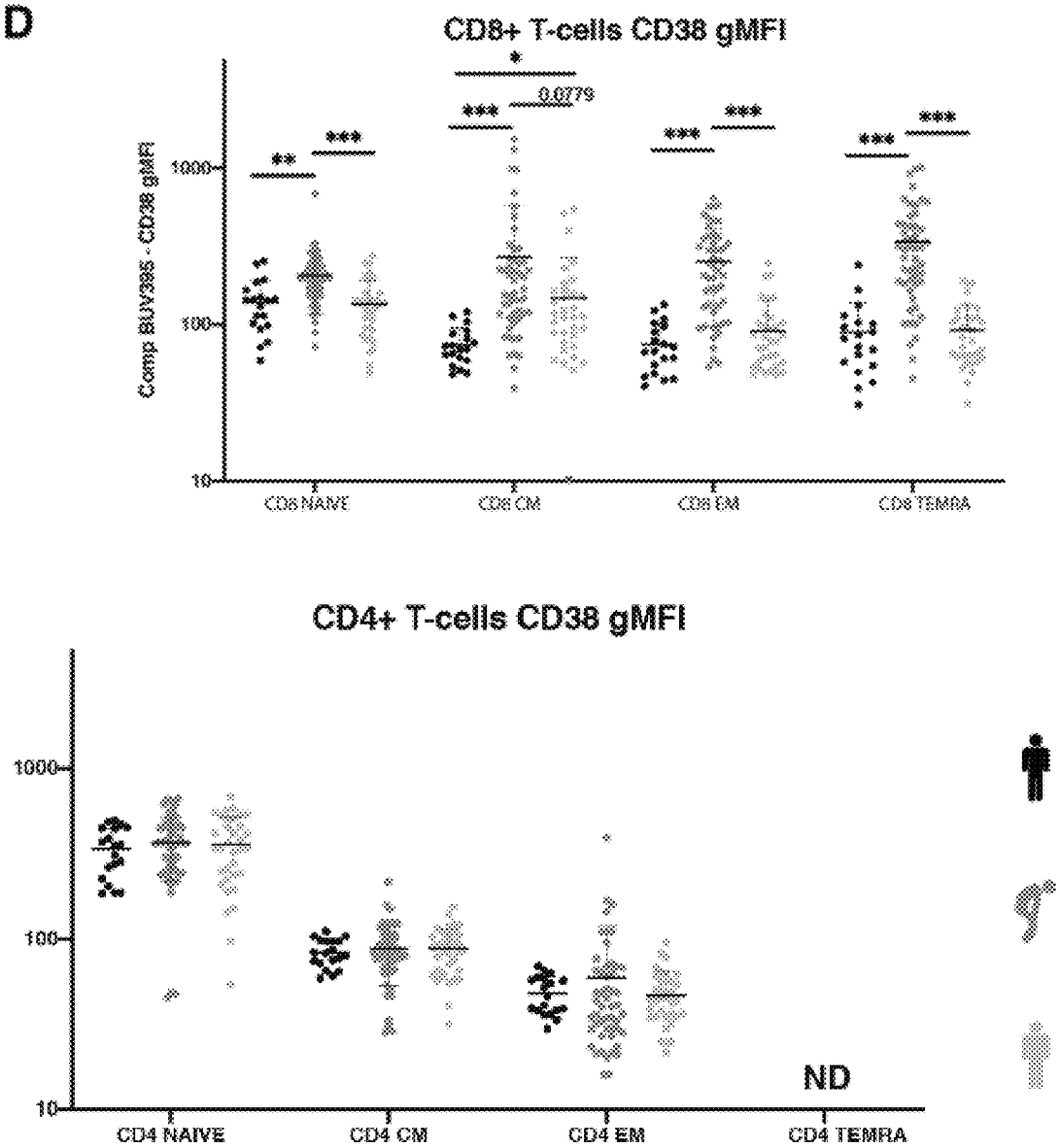
FIG. 2D1

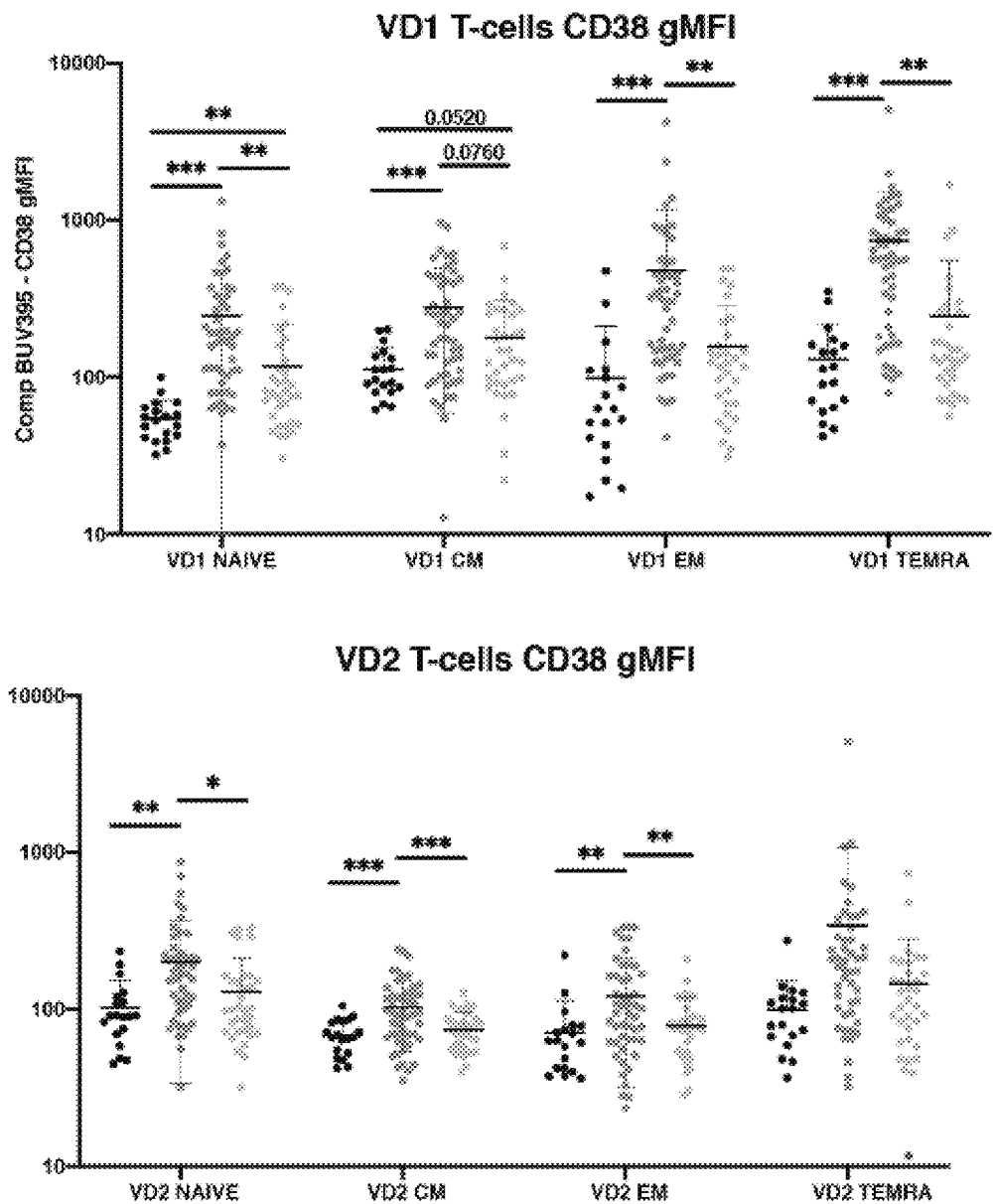
FIG. 2D2

A

C

| analyte_processed | pvalue | r | r2 |
|---|---|---|---|
| MCP-1 | 5.9475E-31 | 0.9952926 | 0.99060737 |
| PDGF-AA | 1.0262E-27 | 0.99211834 | 0.98429881 |
| IL-5 | 2.6522E-12 | 0.98948711 | 0.97908473 |
| RANTES | 1.6258E-16 | 0.96794197 | 0.93691166 |
| GRO | 5.7217E-16 | 0.95647902 | 0.91485211 |
| MDC | 6.139E-13 | 0.9147584 | 0.83678294 |
| TNFalpha | 7.2058E-13 | 0.91377281 | 0.83498075 |
| FGF-2 | 2.642E-08 | 0.90060808 | 0.81109492 |
| IP-10 | 2.2645E-08 | 0.87479092 | 0.76525915 |
| IFNgamma | 0.00010306 | 0.80326746 | 0.64523862 |
| GM-CSF | 0.00145789 | 0.78560667 | 0.61717785 |
| IL-17A | 0.00260713 | 0.71736501 | 0.51461255 |
| EGF | 0.01210713 | 0.56285886 | 0.3166101 |
| PDGF-AB/BB | 0.09238846 | 0.4668489 | 0.2179479 |
| MIP-1beta | 0.04705156 | 0.44898796 | 0.20159019 |
| sCD40L | 0.63529644 | 0.11298794 | 0.01276627 |

FIG. 12E

METHOD OF EVALUATING PROGRESSION OF AN INFECTIOUS DISEASE AND/OR INFLAMMATORY DISEASE

TECHNICAL FIELD

The present disclosure relates broadly to a method of immunotyping a subject having an infectious disease and/or inflammatory disease. In particular, the method evaluates the risk of progression of an infectious disease and/or inflammatory disease.

BACKGROUND

Severe Acute Respiratory Syndrome coronavirus 2 (SARS-CoV-2) first appeared in Wuhan, China in late 2019. It is a novel pathogen responsible for the coronavirus disease 2019 (COVID-19) pandemic. COVID-19 patients experience a wide spectrum of clinical manifestations that ranges from low-grade fever and mild respiratory symptoms, to more severe forms. This including acute respiratory distress syndrome (ARDS), which requires provision of supplemental oxygen, and in some cases intubation and mechanical ventilation. The standard of care differs depending on the patient symptoms and early indication of patients at risk of severe disease will improve their outcomes. The majority of critical cases of COVID-19 are associated with coagulopathy with a high prevalence of thromboembolic events in patients under mechanical ventilation which lead to inclusion of anticoagulation therapies in the standard of care of severe COVID-19 cases.

In addition, while the strong inflammatory response to COVID-19 has been proposed to be associated to COVID-19 associated coagulopathy, it remains unclear how SARS-CoV-2 infection affects the activation of immune cells and their contribution towards the severity of disease outcomes in patients.

The high circulation of this pandemic has put a heavy strain on healthcare system and an urgent unmet need for correct patient characterisation and management. Therefore, there is a need to provide a method of characterising and/or immunotyping subjects having SARS-COV2.

SUMMARY

In one aspect, there is provided a method of evaluating risk of severe outcome of an infectious disease and/or an inflammatory disease in a patient, the method comprising: determining/measuring the number of one or more immune cells selected from the group consisting of VD2 T cells, CD8 T cells, and immature neutrophils in a sample obtained from the patient, wherein the patient has an enhanced risk of severe infectious disease and/or inflammatory disease outcome when: (i) the ratio of immature neutrophils to VD2 T cell is at least 2:1, and/or (ii) the ratio of immature neutrophils to CD8 T cell is at least 0.5:1.

In some examples, the infectious disease is a coronavirus infection, optionally a SARS-COV-2 infection.

In some examples, the severe infectious disease outcome is pneumonia and/or hypoxia.

In some examples, the method further comprises measuring the number of one or more cells selected from the group consisting of CD4+ T cells, mucosal-associated invariant T cells (MAIT), VD1 T cells, plasmacytoid dendritic cells (pDCs), dendritic cells (DCs), classical and intermediate monocytes, optionally when a reduction in the number of one or more cells as compared to a control indicates an enhanced risk of severe infectious disease and/or inflammatory disease outcome. In some examples, the method further comprises measuring the expression of one or more myeloid activation markers on monocytes, optionally a reduction in the expression of one or more myeloid activation markers on monocytes as compared to a control indicates an enhanced risk of severe infectious disease and/or inflammatory disease outcome.

In some examples, the control is a healthy subject or a sample from the patient at an earlier time point.

In some examples, the number of one or more immune cells are determined by measuring the number of cells expressing one or more markers selected from the group consisting of CD45, CD66b, CD15, CD16, CD10, CD3, VD2, and CD8.

In some examples, the method further comprising performing flow cytometry and/or immunostaining to measure/determine the number of one or more immune cells.

In some examples, the number of immature neutrophils is determined by measuring the number of cells having the cell surface phenotype CD45+CD3−CD66b/CD15+CD16intermediate/−CD10−.

In some examples, the number of VD2 T cells is determined by measuring the number of cells having the cell surface phenotype CD45+CD3+VD2+.

In some examples, the number of CD8 T cells is determined by measuring the number of cells having the cell surface phenotype CD45+CD3+CD8+.

In some examples, the method further comprises determining the absolute number of immune cells measured in the sample.

In some examples, the sample is obtained from the patient between 1 to 10 days post-illness onset (pio) and/or between 1 to 40 days post-treatment.

In another aspect, there is provided method of treating a patient with a severe infectious disease and/or inflammatory disease, the method comprising: determining/measuring the number of one or more immune cells selected from the group consisting of VD2 T cells, CD8 T cells, and immature neutrophils in a sample obtained from the patient, wherein the patient has an enhanced risk of severe infectious disease and/or inflammatory disease outcome when: (i) the ratio of immature neutrophils to VD2 T cell is at least 2:1, and/or (ii) the ratio of immature neutrophils to CD8 T cell is at least 0.5:1, administering a care treatment for severe infectious disease and/or inflammatory disease to the patient.

In some examples, the infectious disease is a coronavirus infection, optionally a SARS-COV-2 infection.

In some examples, the care treatment one or more selected from the group consisting of cytokine storm inhibitors, COX inhibitors, anti-IL-17 and JAK2 inhibitor therapies.

In some examples, the method further comprises determining the number of one or more immune cells selected from the group consisting of VD2 T cells, CD8 T cells, and immature neutrophils at a time point later than (or after) the administration of the care treatment of the disease, wherein an increase ratio of immature neutrophils to VD2 T cells and/or an increase ratio of immature neutrophils to CD8 T cells indicates a worsening of the condition in the patient.

In yet another aspect, there is provided a kit comprising one or more reagent that determines and/or measures the number of VD2 T cells and immature neutrophils in a cell, optionally the kit further comprises one or more reagent that determines and/or measures the expression of CD8.

In some examples, the one or more reagent determines and/or measures the expression of CD45, CD66b or CD15, CD16, CD3, and VD2, optionally CD8 on a cell.

In some examples, the kit further comprises an agent that determines the expression of CD10, optionally the kit further comprises an agent that determines the absolute number of immune cells in a sample.

DETAILED DESCRIPTION OF EMBODIMENTS

Severe acute respiratory syndrome coronavirus 2 (SARS-CoV-2) is the etiological pathogen responsible for the ongoing coronavirus disease (COVID-19) pandemic. COVID-19 patients experience a wide spectrum of clinical manifestations that range from low-grade fever and mild respiratory symptoms, to more severe forms such as acute respiratory distress syndrome (ARDS), which requires provision of supplemental oxygen, and in some cases intubation and mechanical ventilation. The standard of care differs depending on the patient symptoms and early identification of patients at risk of severe disease will improve their outcomes. The high circulation of this pandemic has put a heavy strain on healthcare system and an urgent unmet need for correct patient management Previous clinical studies reported associations with clinical blood counts, while others have specifically assessed T-cell subsets for activation and exhaustion markers. Since strong evidence points to a cytokine storm as the culprit for disease severity, various groups have investigated cytokine-secreting pathogenic T-cells and inflammatory monocytes that could have triggered this phenomenon. In addition, flow cytometry analysis in COVID-19 patients has also shown a polarisation towards the Th17 subtype and a highly activated and exhausted CD8+ T-cell compartment. All these studies were carried out on peripheral blood mononuclear cells (PBMCs), thus excluding most granulocyte populations. However, to elucidate all the immune subsets that could potentially trigger severe COVID-19 pathology, it is imperative to perform comprehensive whole blood immunophenotyping of COVID-19 patients which includes granulocyte populations.

In the present disclosure, high dimensional flow cytometry was employed to analyse a wide spectrum of more than 50 subsets of the myeloid and lymphoid immune cell compartments. The study was carried out during the ongoing SARS-CoV-2 pandemic in Singapore with a cohort of 54 COVID-19 patients who presented with varied clinical manifestations ranging from mild to fatal outcomes. This comprehensive immunophenotyping allowed the identification of immature neutrophils, CD8 T-cells and gamma delta (VD) 2 T-cells as key immune cell populations that undergo substantial changes in the cell counts across the spectrum of clinical severity. Their numbers, in fact, represent an early and robust prognosis value as shown by 'receiver operating characteristics' (ROC) analysis. As such, disclosed is a method of evaluating progression risk of an infectious disease and/or an inflammatory disease in a patient.

In one aspect, there is provided a method of evaluating risk of severe outcome of an infectious disease and/or an inflammatory disease in a patient, the method comprising: determining/measuring the number of one or more immune cells selected from the group consisting of VD2 T cells, CD8 T cells, and immature neutrophils in a sample obtained from the patient, wherein the patient has an enhanced risk of severe infectious disease and/or inflammatory disease outcome when: (i) the ratio of immature neutrophils to VD2 T cell is at least 2:1, and/or (ii) the ratio of immature neutrophils to CD8 T cell is at least 0.5:1.

In some examples, the ratio of immature neutrophils to VD2 T cells and/or CD8 T cells may be as described herein. In some examples, the ratio of immature neutrophils to VD2 T cells may be as described in Table 5, and/or Table 6, and/or Table 7, and/or Table 8. In some examples, the ratio of immature neutrophils to CD8 T cells may be as described in Table 9 and/or Table 10, and/or Table 11, and/or Table 12. In some examples, the ratio of immature neutrophils to VD2 T cells and/or CD8 T cells may be as described in Table 5, and/or Table 6, and/or Table 7, and/or Table 8, and/or Table 9, and/or Table 10, and/or Table 11, and/or Table 12 as described in column "ratio" or "likelihood ratio". In some examples, the ratio of immature neutrophils to VD2 T cells ratio is 2 to 5000 (of immature neutrophils):1 (of VD2 T cells), or 2:1, or 3:1, or 4:1, or 5:1, or 6:1, or 7:1, or 8:1, or 9:1, or 10:1, or 11:1, or 12:1, or 13:1, or 14:1, or 15:1, or 16:1, or 17:1, or 18:1, or 19:1, or 20:1, or 100:1, or 1000:1, or 2000:1, or 3000:1, or 4000:1, or 5000:1. In some examples, the ratio of immature neutrophils to CD8 T cells ratio is 0.5 to 5000 (of immature neutrophils):1 (of CD8 T cells), or 0.5:1, or 1:1, or 2:1, or 3:1, or 4:1, or 5:1, or 6:1, or 7:1, or 8:1, or 9:1, or 10:1, or 11:1, or 12:1, or 13:1, or 14:1, or 15:1, or 16:1, or 17:1, or 18:1, or 19:1, or 20:1, or 100:1, or 1000:1, or 2000:1, or 3000:1, or 4000:1, or 5000:1.

Also disclosed is a method that may comprise determining/measuring the number immature neutrophils in a first sample, comparing the number of immature neutrophils to those of a second sample, wherein an increased number and/or proportion of immature neutrophils in the first sample is indicative of an enhanced risk of severe infectious disease and/or inflammatory disease.

Also disclosed is a method that may comprise determining/measuring the number of one or more immune cells selected from the group consisting of VD2 T cells, CD8 T cells, and immature neutrophils in a sample obtained from the patient and a control, determining the patient has an enhanced risk of severe infection outcome when: (i) the number of VD2 T cell is reduced relative to the control, and/or (ii) the number of immature neutrophils is enhanced relative to control, and/or (iii) the number of CD8 T cell is reduced relative to the control.

Also disclosed is a method of determining/evaluating progression of an infectious disease and/or an inflammatory disease in a patient, the method comprising: determining/measuring an activity, an amount and/or a proportion of one or more immune cells selected from the group consisting of VD2 T cells, CD8 T cells, and immature neutrophils in first sample from the subject; and comparing the activity, the amount and/or the proportion of one or more immune cells selected from the group consisting of VD2 T cells, CD8 T cells, and immature neutrophils to those of a second sample from the subject, the second sample being obtained from subject at a later timepoint than the first sample, wherein an increased ratio between immature neutrophils and VD2 T cells or CD8 T cells in the second sample as compared to the first sample is indicative of a worsening of the condition in the subject, and/or wherein a reduced ratio between immature neutrophils and VD2 T cells or CD8 T cells in the second sample as compared to the first sample is indicative of an improvement of the condition in the subject, and wherein a similar ratio between immature neutrophils and VD2 T cells or CD8 T cells in the first sample as compared to the second sample is indicative of a non-improvement and/or stabilisation of the condition in the subject.

In some examples, the infectious disease is a viral infection. In some examples, the infectious disease is a coronavirus infection, optionally a SARS-COV-2 infection. In some examples, wherein the severe infectious disease outcome is pneumonia and/or hypoxia.

In some examples, the method further comprises measuring the number of dysregulated monocytes and/or dendritic cells. In some examples, the monocytes and dendritic cells are detected in circulation (such as blood and/or lymphatic circulation).

In some examples, the method further comprises measuring the number of one or more immune cells such as but not limited to CD4+ T cells, mucosal-associated invariant T cells (MAIT), VD1 T cells, plasmacytoid dendritic cells (pDCs), dendritic cells (DCs), classical monocyte, intermediate monocytes, and the like. In some examples, a reduction in the number of one or more cells as compared to a control indicates an enhanced risk of severe infectious disease and/or inflammatory disease outcome.

In some examples, the method further comprises measuring the expression of one or more myeloid activation markers on monocytes, optionally a reduction in the expression of one or more myeloid activation markers on monocytes as compared to a control indicates an enhanced risk of severe infectious disease and/or inflammatory disease outcome. In some examples, the myeloid activation marker may include, but is not limited to, CD86, CD33, CD169, and the like.

In some examples, the control is a healthy subject or a sample or result (or value) from the patient at an earlier time point (such as prior measurement).

In some examples, the control is a healthy subject or a sample obtained from the patient at an earlier time point. As used herein, the term "healthy subject" may refer to a subject/person who has been determined not to have the infectious disease and/or inflammatory disease as described herein. In some examples, the term "healthy subject" may also include a subject/person who has been determined to be disease free.

In some examples, the second sample and/or control may be obtained from the same subject/person at an earlier time point than the first sample. In some examples, the second sample and/or control may be obtained from a different subject/person who has been determined not to have the infectious disease and/or inflammatory disease as described herein. In some examples, the second sample and/or control may be obtained from a subject different from the subject of the first sample. In some examples, the first sample may be obtained from a patient diagnosed to have an infectious disease and/or inflammatory disease and the second sample and/or control may be obtained from a subject determined to be free of the infectious disease and/or inflammatory disease in question.

In some examples, the number of one or more immune cells are determined by measuring the number of cells expressing one or more markers selected from the group consisting of CD45, CD66b, CD15, CD16, CD10, CD3, VD2, and CD8.

The methods of which the markers as described herein are detected would not be beyond the purview of the skill of a person skilled in the art. In some examples, wherein method further comprising performing flow cytometry and/or immunostaining to measure/determine the number of one or more immune cells.

In some examples, the methods as described herein may determine the number of one or more cells such as, but not limited to, granulocytes, CD16+ cells, CD45+ cells, CD3+ cells, VD2, CD66, CD15, CD16, CD10, and the like. In some examples, the method as described herein may identify and/or separate immune cells from the rest of the sample (such as blood products), optionally the separation and/or identification uses an agent and/or composition that recognizes and/or binds to CD45.

In some examples, the method as described herein may identify and/or separate granulocytes from the rest of the sample, optionally the separation and/or identification uses an agent and/or composition that recognizes and/or binds to CD66b and/or CD15.

In some examples, the method as described herein may identify and/or separate T cells (T lymphocytes) from the rest of the sample, optionally the separation and/or identification uses an agent and/or composition that recognizes and/or binds to CD3.

In some examples, the method as described herein may identify and/or separate mature neutrophils from immature neutrophils, optionally the separation and/or identification uses an agent and/or composition that recognizes and/or binds to CD10. Thus, in some examples, the method as described herein may identify and/or separate and/or distinguish mature neutrophils as CD16high CD10+ population and immature neutrophils as CD45+ CD3− CD66b/CD15+ CD16intermediate/−CD10− population. In some examples, the neutrophils are determined/distinguished/measured within the granulocyte population.

As exemplified in the Experimental section, number of immature neutrophils may be determined by measuring the number of cells having one or more cell surface phenotype including, but is not limited to, $CD45^+$, $CD3^-$, CD66b+, $CD15^+$, $CD16^{intermediate/-}$, $CD10^-$, and the like. In some examples, the neutrophils may not be mature neutrophils. In some examples, the number of immature neutrophils may be determined by measuring the number of cells having two or more, or three or more, or four or more, or five or more, or all six cell surface phenotypes CD45+, CD3−, CD66b+, CD15+, CD16intermediate/− and/or CD10−. In some examples, the neutrophils may not express $CD16^{high}$ and $CD10^+$. Thus, in some examples, the number of immature neutrophils is determined by measuring the number of cells having the cell surface phenotype CD45+ CD3− CD66b/CD15+CD16intermediate/−CD10−.

In some examples, the number of VD2 T cells is determined by measuring the number of cells having one or more cell surface phenotype including, but is not limited to, $CD45^+$, $CD3^+$, $VD2^+$, and the like. In some examples, the number of VD2 T cells may be determined by measuring two or more, or all three cell surface phenotypes CD45+, CD3+, and/or VD2+. In some examples, the number of VD2 T cells is determined by measuring the number of cells having the cell surface phenotype CD45+CD3+VD2+.

In some examples, the number of CD8 T cells may be determined by method well known in the art. In some examples, the number of CD8 T cells may be measured by the number of cells having one or more cell surface phenotype including, but is not limited to, CD45+, CD3+, CD8+, and the like. In some examples, the number of CD8 T cells may be determined by measuring two or more or all three cell surface phenotypes CD45+, CD3+, and/or CD8+. In some examples, the number of CD8 T cells is determined by measuring the number of cells having the cell surface phenotype CD45+CD3+CD8+.

In some examples, the methods as described herein may determine/measure the number and/or ratio of VD2 T cells and immature neutrophils. In some examples, the methods as described herein may determine/measure the number and/or ratio of CD8 T cells and immature neutrophils.

In some examples, the method may further comprise determining the absolute number of immune cells measured in the sample. In some examples, determining the absolute number of immune cells may be measured by an agent and/or composition capable of determining absolute number of cells detected. For example, the agent and/or composition may be a counting beads that can be added into the sample prior to analysis. Without wishing to be bound by theory, the counting beads count acquired by flow versus the number of beads originally in the mixed can be used to determinate the absolute number of immune cells as described herein in a given sample (for example to determine the absolute number of immature neutrophils, VD2 T cells, and optionally CD8 T cells in 100 µL of sample/patient blood).

In some examples, the first sample is obtained from the patient between 1 to 10 days post-illness onset (pio) and/or from first symptoms (such as any cold-like symptom). In some examples, the sample is obtained from the patient between 1 to 10 days post-illness onset (pio), or 1 to 7 days pio, or 1 day pio, or 2 days pio, or 3 days pio, or 4 days pio, or 5 days pio, or 6 days pio, or 7 days pio, or 8 days pio, or 9 days pio, or 10 days pio. In some examples, the second or more/later samples may be obtained from the patient at any later time point post-illness onset (pio) and/or post-care or treatment. In some examples, the second or later samples may be obtained from the patient at between 1 to 40 days post-illness onset (pio) and/or post-care or treatment.

In some examples, the sample is a biological sample. In some examples, the sample is a biological fluid. In some examples, the sample is a blood sample. In some examples, the sample is a peripheral blood sample.

In another aspect, there is provided a method of treating a patient with a severe infectious disease and/or inflammatory disease, the method comprising: determining/measuring the number of one or more immune cells selected from the group consisting of VD2 T cells, CD8 T cells, and immature neutrophils in a sample obtained from the patient, wherein the patient has an enhanced risk of severe infectious disease and/or inflammatory disease outcome when: (i) the ratio of immature neutrophils to VD2 T cell is as described herein, and/or (ii) the ratio of immature neutrophils to CD8 T cell is as described herein, and administering a care treatment for severe infectious disease and/or inflammatory disease to the patient.

In some examples, the infectious disease is a coronavirus infection, optionally a SARS-COV-2 infection. As such, wherein the care treatment may comprise standard antiviral treatment. It would be within the purview of the person skilled in the art (such as a medical professional) to determine the appropriate care treatment for the patient. For example, appropriate treatments will be earlier standard of care administration and/or earlier hospitalisation for monitoring. In some examples, the care treatment may include, but is not limited to, cytokine storm inhibitors, COX inhibitors, anti-IL-17, JAK2 inhibitor therapies, and the like.

In some examples, the method further comprises determining the number of one or more immune cells selected from the group consisting of VD2 T cells, CD8 T cells, and immature neutrophils at a time point later than (or after) the administration of the care treatment of the disease, wherein an increase ratio of immature neutrophils to VD2 T cells and/or an increase ratio of immature neutrophils to CD8 T cells indicates a worsening of the condition in the patient.

Also disclosed is a method of determining/evaluating the efficacy of a treatment regimen (e.g. efficacy of a drug) for a condition in a subject, the method comprising: determining/measuring an activity, an amount and/or a proportion of one or more immune cells selected from the group consisting of VD2 T cells, CD8 T cells, and immature neutrophils in first sample from the subject; and comparing the activity, the amount and/or the proportion of one or more immune cells selected from the group consisting of VD2 T cells, CD8 T cells, and immature neutrophils to those of a second sample from the subject, the second sample being obtained from subject at a later timepoint in the treatment regimen than the first sample, wherein the treatment regimen is considered effective when the second sample has a reduced ratio of immature neutrophils to VD2 T cells or CD8 T cells. In some examples, in cases where it is not possible and/or practical to retain a portion of the first sample for further analysis at the time of analysis of the second sample, the first sample may refer to the analytical result or analysis of the sample that was obtained at an earlier timepoint. That is, in some examples, the comparison of the ratio of immature neutrophils to VD2 T cells or to CD8 T cells are made based on the analysis of data obtained in the first sample (i.e. earlier timepoint) vs. the second sample (i.e. later timepoint, such as after a treatment).

The present disclosure also includes the possibility of providing an accompanying software for automated analysis of the measurements and/or determination and/or detection of the cells as described herein. Therefore, the present method as described herein may be implemented in an apparatus and/or device with software compatible to calculating the total number and/or ratio of the immune cells as described herein.

In yet another aspect, there is provided a kit comprising one or more reagent that determines and/or measures the number of VD2 T cells and immature neutrophils in a cell, optionally the kit further comprises one or more reagent that determines and/or measures the expression of CD8. In some examples, the kit comprises one or more reagent that determines and/or measures the expression of one or more CD45, CD66b or CD15, CD16, CD3, and VD2, optionally CD8 on a cell.

In some example, the kit further comprises an agent that determines the correct expression of CD10. In some examples, the one or more reagent may be premixed and/or lyophilized. In some examples, the kit may comprise one, or two, or three, or four, or five, or six, or seven reagents that determines and/or measures the expression of one, or two, or three, or four, or five, or six, or all of CD45, CD66b or CD15, CD16, CD3, VD2, and CD8. In some examples, the seven reagents for measuring the seven markers may be provided in a premix that optionally is lyophilized. In some examples, the kit may comprise one, or two, or three, or four, or five, or six, or seven, or all eight reagents that determines and/or measures the expression of one, or two, or three, or four, or five, or six, or seven, or all of CD45, CD66b or CD15, CD16, CD3, VD2, CD8, and CD10. In some examples, the seven reagents for measuring the seven markers may be provided in a premix that optionally is lyophilized.

In some examples, the kit further comprises an agent and/or composition that determines the absolute number of cells detected. In some examples, the kit further comprises an agent that determines the absolute number of immune cells in a sample. For example, the agent and/or composition may be a counting beads that can be added into the sample prior to analysis. Without wishing to be bound by theory, the counting beads count acquired by flow versus the number of beads originally in the mixed can be used to determinate the absolute number of immune cells as described herein in a given sample (for example to determine the absolute number of immature neutrophils, VD2 T cells, and optionally CD8 T cells in 100 µL of sample/patient blood).

In some examples, the kit further comprises an agent and/or composition that measures the number of dysregulated monocytes and/or dendritic cells. In some examples, the kit further comprises an agent and/or composition that measures the number of monocytes and/or dendritic cells in circulation.

In some examples, the kit further comprises an agent and/or composition that measures the number of one or more cells such as, but is not limited to, CD4+ T cells, mucosal-associated invariant T cells (MAIT), VD1 T cells, plasmacytoid dendritic cells (pDCs), dendritic cells (DCs), classical and intermediate monocytes. In some examples, the kit further comprises an agent and/or composition that measures the expression of one or more myeloid activation markers on monocytes. The term "associated with", used herein when referring to two elements refers to a broad relationship between the two elements. The relationship includes, but is not limited to a physical, a chemical or a biological relationship. For example, when element A is associated with element B, elements A and B may be directly or indirectly attached to each other or element A may contain element B or vice versa.

The term "adjacent" used herein when referring to two elements refers to one element being in close proximity to another element and may be but is not limited to the elements contacting each other or may further include the elements being separated by one or more further elements disposed therebetween.

The term "and/or", e.g., "X and/or Y" is understood to mean either "X and Y" or "X or Y" and should be taken to provide explicit support for both meanings or for either meaning.

Further, in the description herein, the word "substantially" whenever used is understood to include, but not restricted to, "entirely" or "completely" and the like. In addition, terms such as "comprising", "comprise", and the like whenever used, are intended to be non-restricting descriptive language in that they broadly include elements/components recited after such terms, in addition to other components not explicitly recited. For example, when "comprising" is used, reference to a "one" feature is also intended to be a reference to "at least one" of that feature. Terms such as "consisting", "consist", and the like, may in the appropriate context, be considered as a subset of terms such as "comprising", "comprise", and the like. Therefore, in embodiments disclosed herein using the terms such as "comprising", "comprise", and the like, it will be appreciated that these embodiments provide teaching for corresponding embodiments using terms such as "consisting", "consist", and the like. Further, terms such as "about", "approximately" and the like whenever used, typically means a reasonable variation, for example a variation of +/−5% of the disclosed value, or a variance of 4% of the disclosed value, or a variance of 3% of the disclosed value, a variance of 2% of the disclosed value or a variance of 1% of the disclosed value.

Furthermore, in the description herein, certain values may be disclosed in a range. The values showing the end points of a range are intended to illustrate a preferred range. Whenever a range has been described, it is intended that the range covers and teaches all possible sub-ranges as well as individual numerical values within that range. That is, the end points of a range should not be interpreted as inflexible limitations. For example, a description of a range of 1% to 5% is intended to have specifically disclosed sub-ranges 1% to 2%, 1% to 3%, 1% to 4%, 2% to 3% etc., as well as individually, values within that range such as 1%, 2%, 3%, 4% and 5%. It is to be appreciated that the individual numerical values within the range also include integers, fractions and decimals. Furthermore, whenever a range has been described, it is also intended that the range covers and teaches values of up to 2 additional decimal places or significant figures (where appropriate) from the shown numerical end points. For example, a description of a range of 1% to 5% is intended to have specifically disclosed the ranges 1.00% to 5.00% and also 1.0% to 5.0% and all their intermediate values (such as 1.01%, 1.02% . . . 4.98%, 4.99%, 5.00% and 1.1%, 1.2% . . . 4.8%, 4.9%, 5.0% etc.,) spanning the ranges. The intention of the above specific disclosure is applicable to any depth/breadth of a range.

Additionally, when describing some embodiments, the disclosure may have disclosed a method and/or process as a particular sequence of steps. However, unless otherwise required, it will be appreciated that the method or process should not be limited to the particular sequence of steps disclosed. Other sequences of steps may be possible. The particular order of the steps disclosed herein should not be construed as undue limitations. Unless otherwise required, a method and/or process disclosed herein should not be limited to the steps being carried out in the order written. The sequence of steps may be varied and still remain within the scope of the disclosure.

Furthermore, it will be appreciated that while the present disclosure provides embodiments having one or more of the features/characteristics discussed herein, one or more of these features/characteristics may also be disclaimed in other alternative embodiments and the present disclosure provides support for such disclaimers and these associated alternative embodiments.

DETAILED DESCRIPTION OF FIGURES

Example embodiments of the disclosure will be better understood and readily apparent to one of ordinary skill in the art from the following discussions and if applicable, in conjunction with the figures. It should be appreciated that other modifications may be made without deviating from the scope of the invention. Example embodiments are not necessarily mutually exclusive as some may be combined with one or more embodiments to form new exemplary embodiments. The example embodiments should not be construed as limiting the scope of the disclosure.

FIGS. 1A-1H SARS-CoV-2 infection induces a decrease in immune cells in peripheral blood. FIG. 1A Schematic representation of flow cytometry workflow.

Figure 1B:
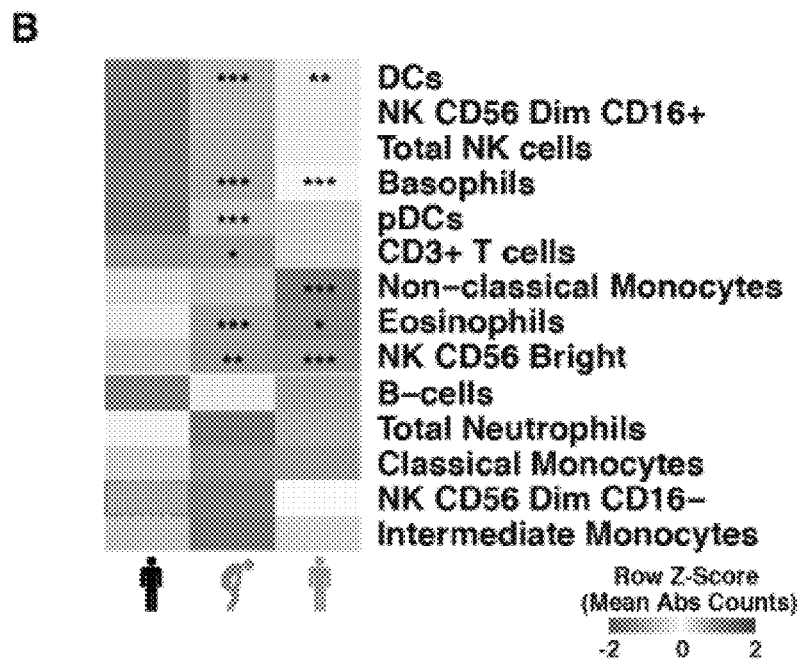
Figure 6A:
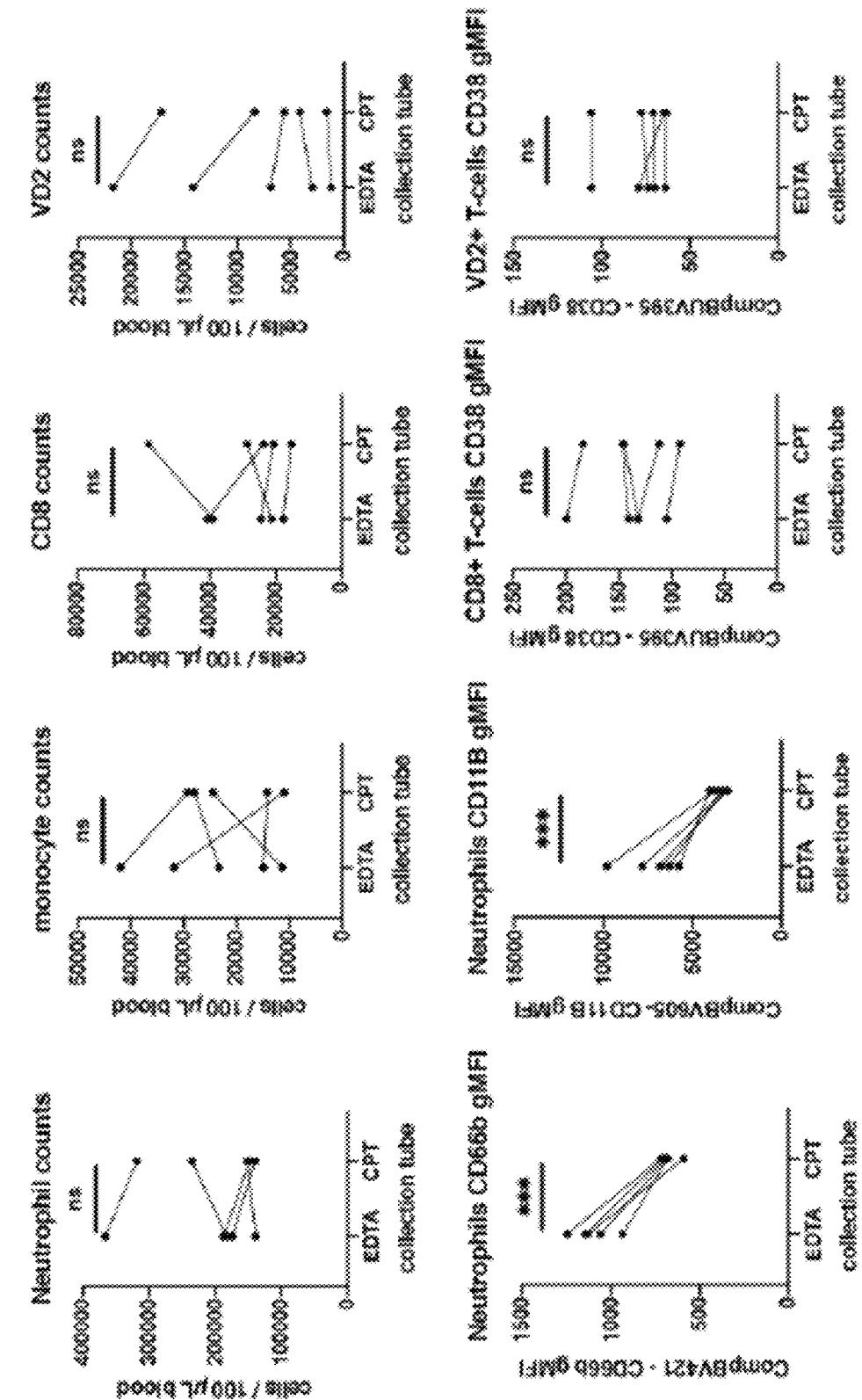

FIG. 1B Heatmap representation of row z-score of mean absolute cell counts across the groups. Individual plots are shown in FIG. 6A.

Figure 1C:
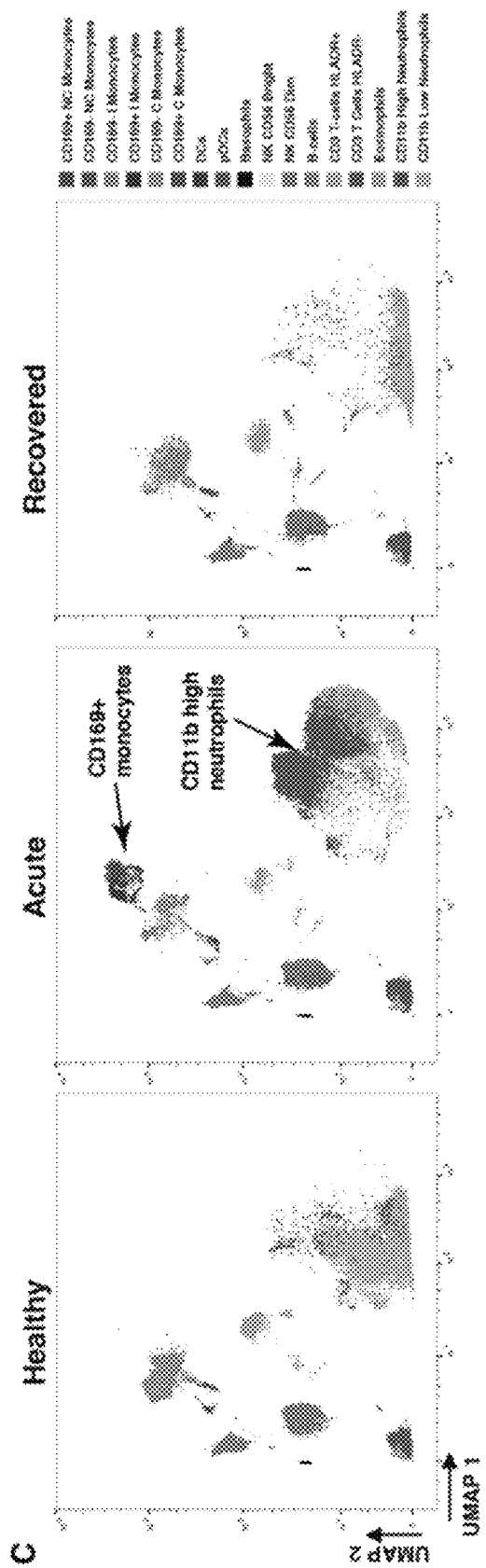

FIG. 1C UMAP clustering of CD45+ immune cells.

Figure 1D:
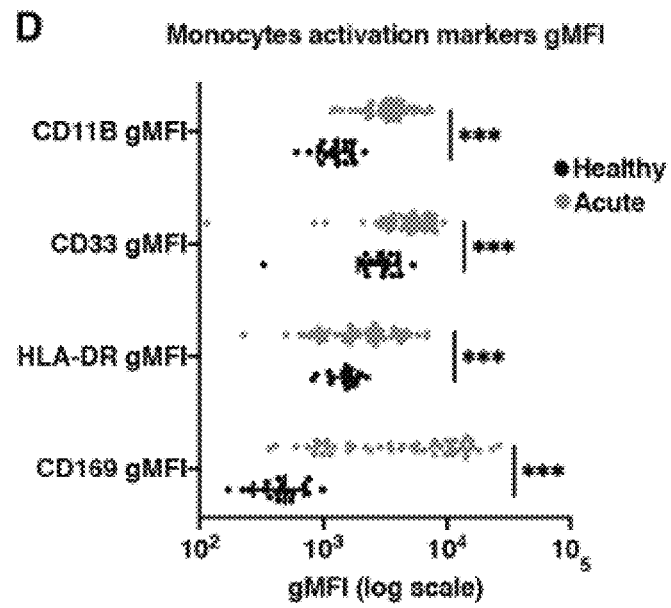

FIG. 1D Monocyte activation markers mean geometric MFI (gMFI) represented as interleaved min to max box plot with all data points shown.

Figure 1E:
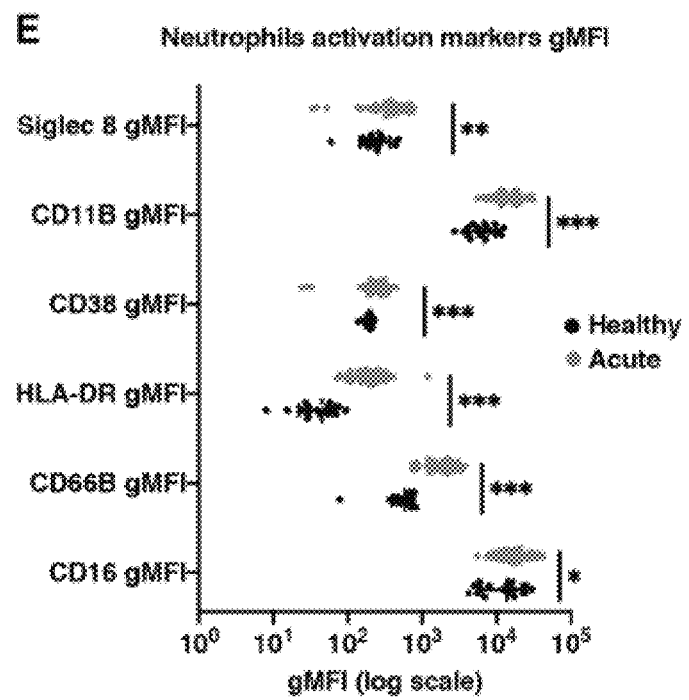

FIG. 1E Neutrophil activation markers mean geometric MFI (gMFI) represented as interleaved min to max box plot with all data points shown.

Figure 1F:
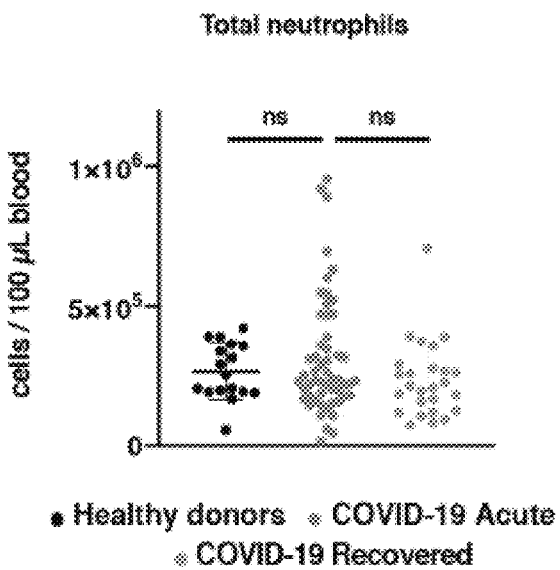

FIG. 1F Absolute neutrophil counts.

Figure 1G:
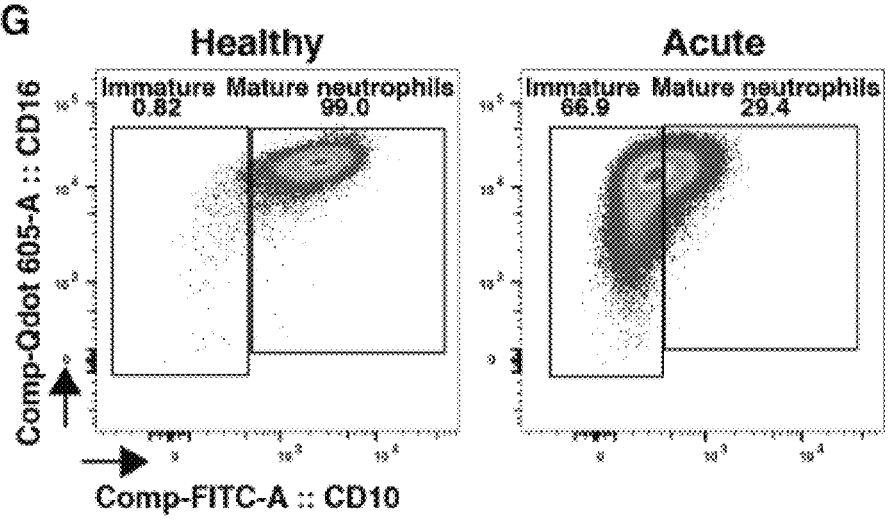

FIG. 1G Representative plot of mature and immature neutrophil gating strategy in healthy control or acute COVID-19 patient.

Figure 1H:
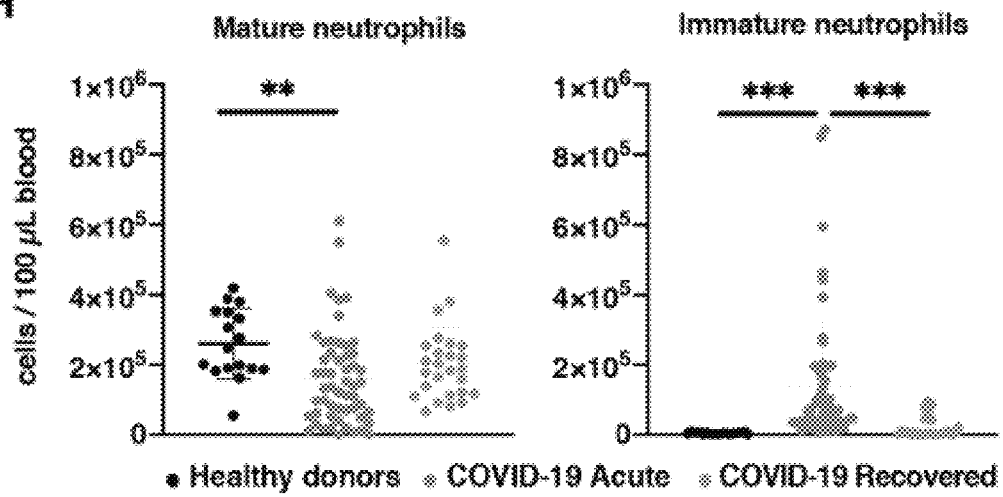

FIG. 1H Mature (CD10+) and Immature (CD10−) Neutrophil Abs counts. Scatter dot plots are presented with mean±SD. Absolute counts were analysed by Kruskal-Wallis using Dunn correction for multiple comparison, gMFI was analysed by Brown-Forsythe and Welch ANOVA without multiple comparison. For heatmap, stars shown in acute column represent healthy vs acute comparison. Stars shown in recovered column represent acute vs recovered comparison. ns non-significant. *p<0.05, p<0.01, *p<0.001. Data available in source data file.

Figure 2A:
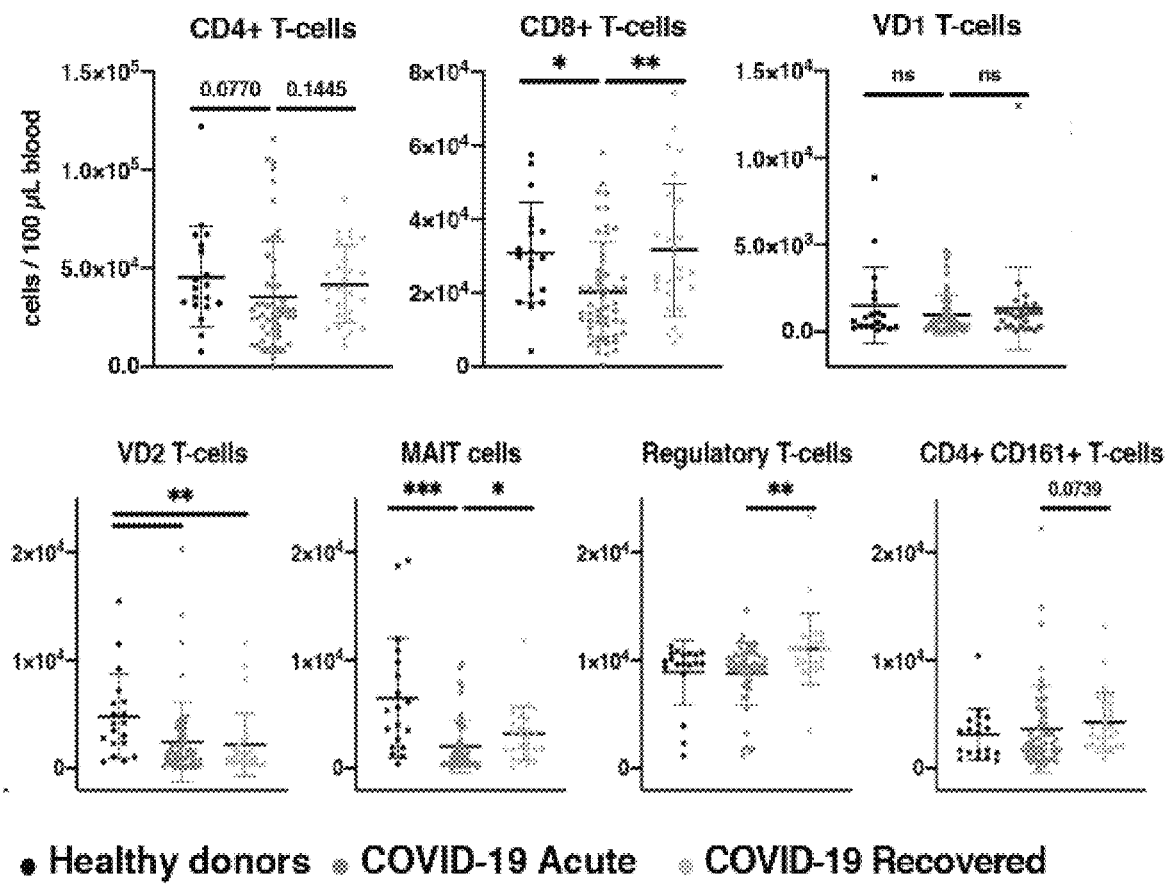

FIGS. 2A-2D2 SARS-CoV-2 infection induces general lymphopenia and CD8, VD1 and VD2 activation. FIG. 2A Absolute counts of T-cell compartments in healthy donors, acute and recovered COVID-19 patient.

Figure 2B:
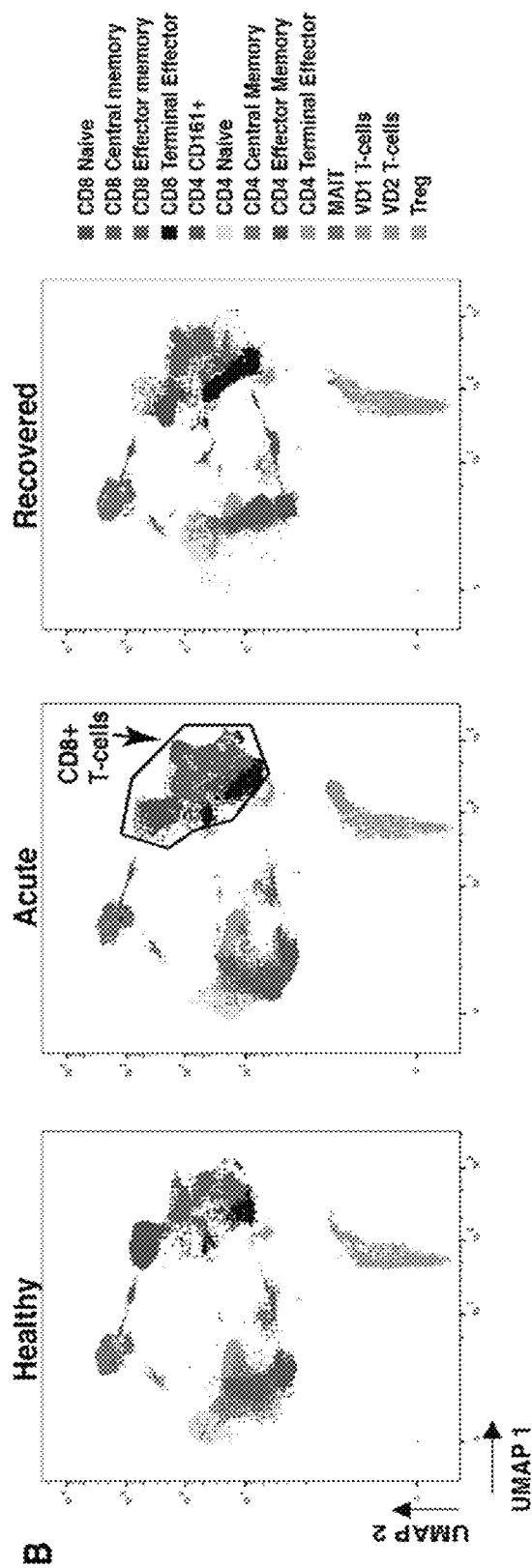

FIG. 2B UMAP clustering of CD3+ cells.

Figure 2C:
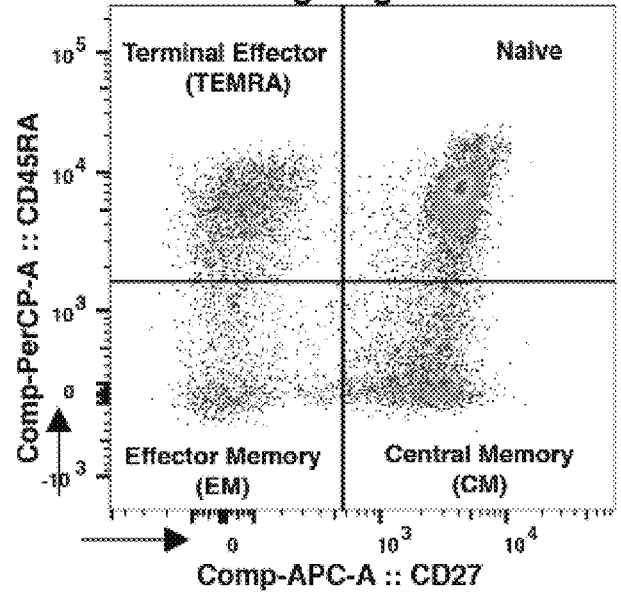
Figure 2C:
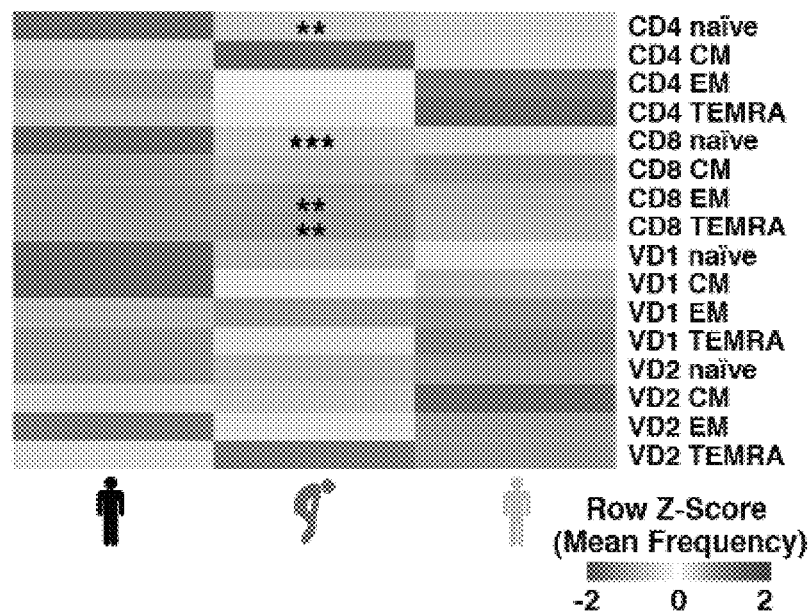

FIG. 2C left panel: CD45RA and CD27 gating strategy example on CD8+ T-cells; right panel: heatmap representation of mean frequencies of T-cell differentiation across the groups, individual plots given in FIG. 7A-B.

FIGS. 2D1-2D2 Changes in CD38 gMFI in naïve, CM, EM and TEMRA f 814 or CD8, CD4, VD1 and VD2 T-cells. ND indicates not determined since frequency of these compartment was too low for accurate gMFI measurement. Absolute counts were analysed by Kruskal-Wallis using Dunn correction for multiple comparison, gMFI was analysed by Brown-Forsythe and Welch ANOVA using Dunnett T3 correction for multiple comparison. Scatter dot plots are presented with mean±SD. For heatmaps, stars shown in acute column represent healthy vs acute comparison. Stars shown in recovered column represent acute vs recovered comparison. *p<0.05, p<0.01, *p<0.001. Data available in source data file.

Figure 3A:
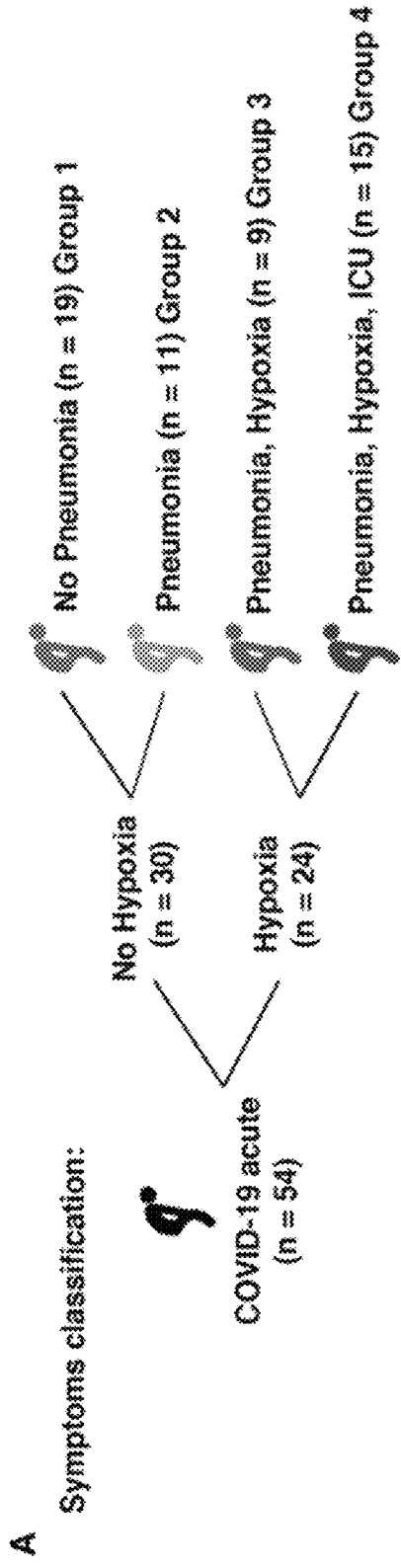

FIGS. 3A-3E Patient symptoms are reflected in immune cell variations. FIG. 3A Schematic representation of clinical symptoms in the patient cohort.

Figure 3B:
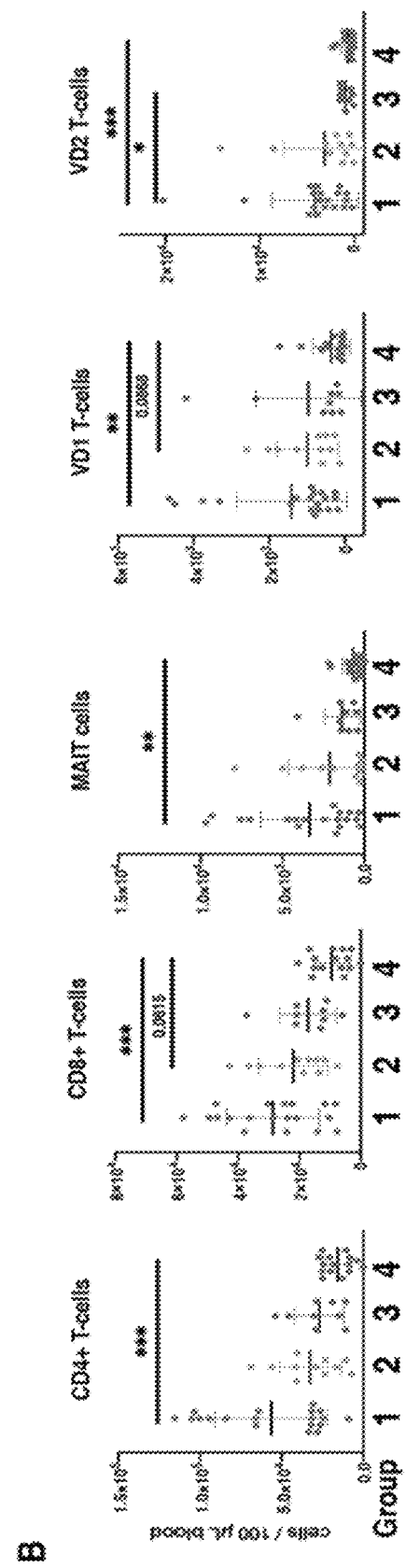

FIG. 3B Absolute counts of T-cells across the severity

Figure 3C:
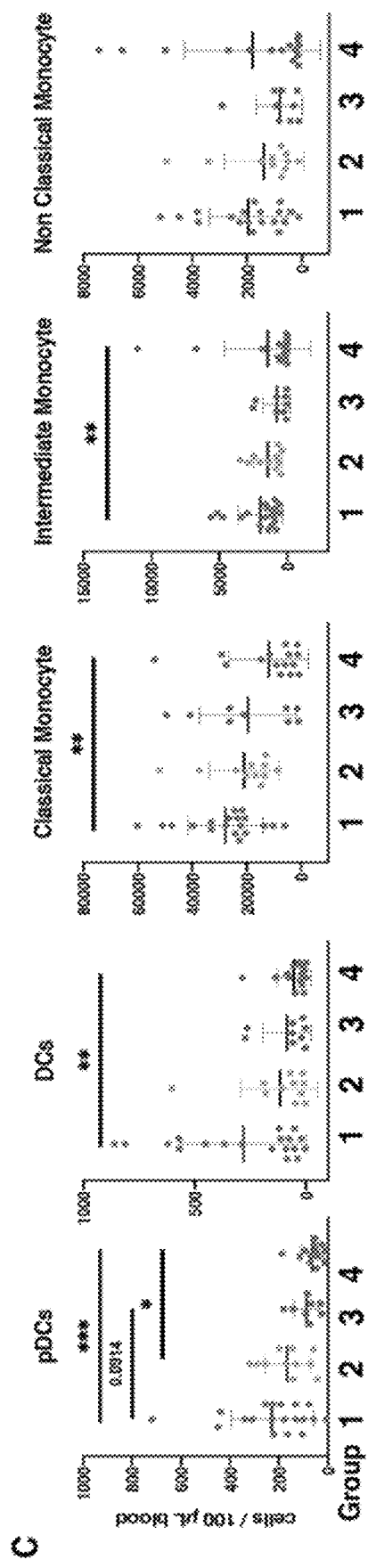

FIG. 3C Absolute counts of antigen presenting cells across the severity.

Figure 3D:
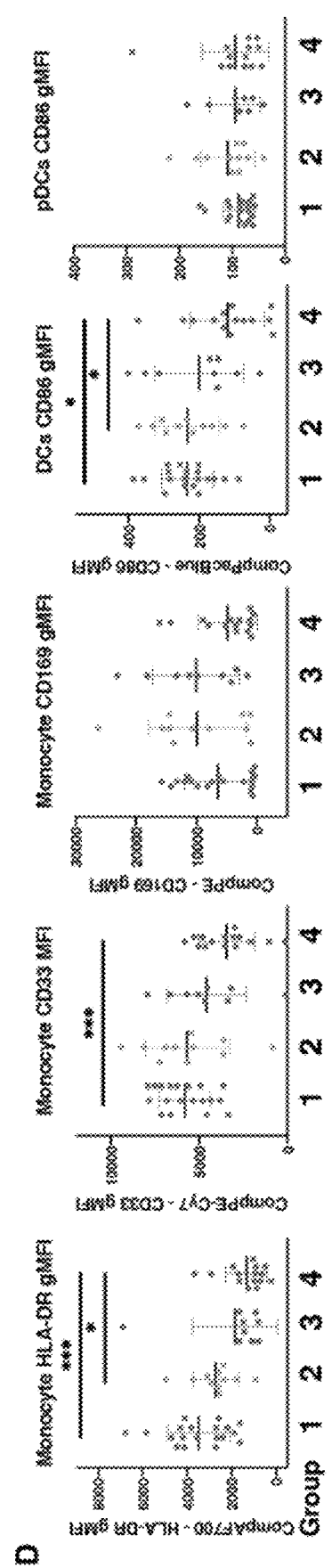

FIG. 3D gMFI of activation markers on antigen presenting cells.

Figure 3E:
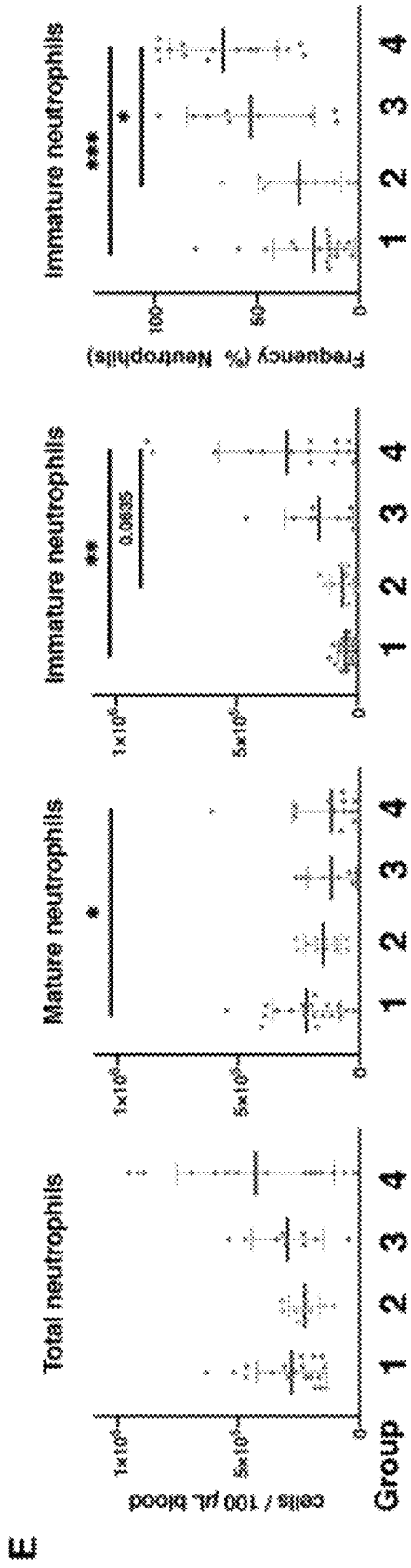

FIG. 3E Absolute counts and frequency in neutrophil compartments. Scatter dot plots are presented with mean±SD. Absolute counts were analysed by Kruskal-Wallis with Dunn multiple testing correction, gMFI was analysed by Brown-Forsythe and Welch ANOVA with Dunnett T3 multiple testing correction. *p<0.05, p<0.01, *p<0.001. Data available in source data file.

Figure 4A:
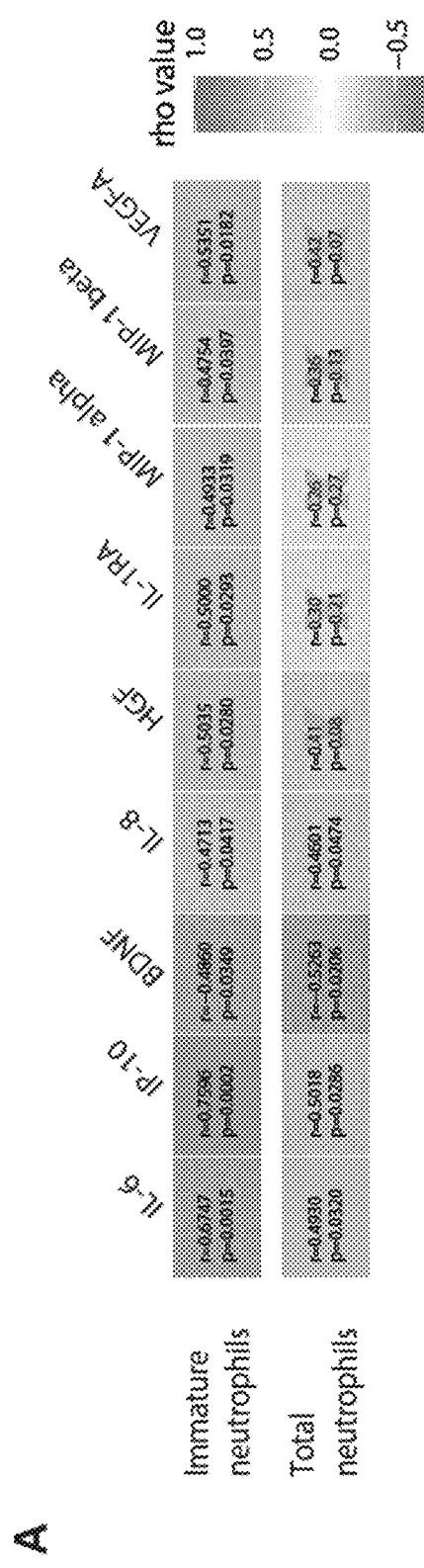
Figure 4B:
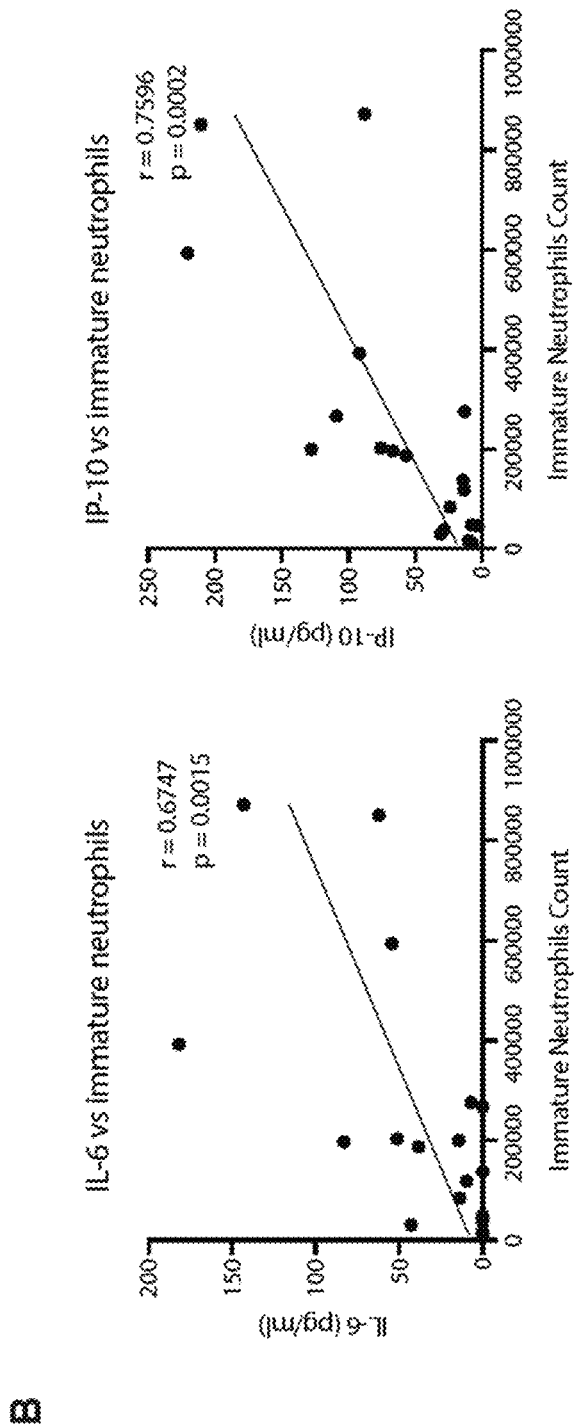

FIGS. 4A-4B Immature neutrophils correlate with several analytes in paired patient plasma. FIG. 4A Spearman correlations between total neutrophils or immature neutrophils and plasma analytes. Red cross represents non-significant correlations.

FIG. 4B Individual plots of Spearman correlations between immature neutrophil counts and IL-6 and IP-10. Line was drawn using simple linear regression. Data available in source data file.

Figure 5A:
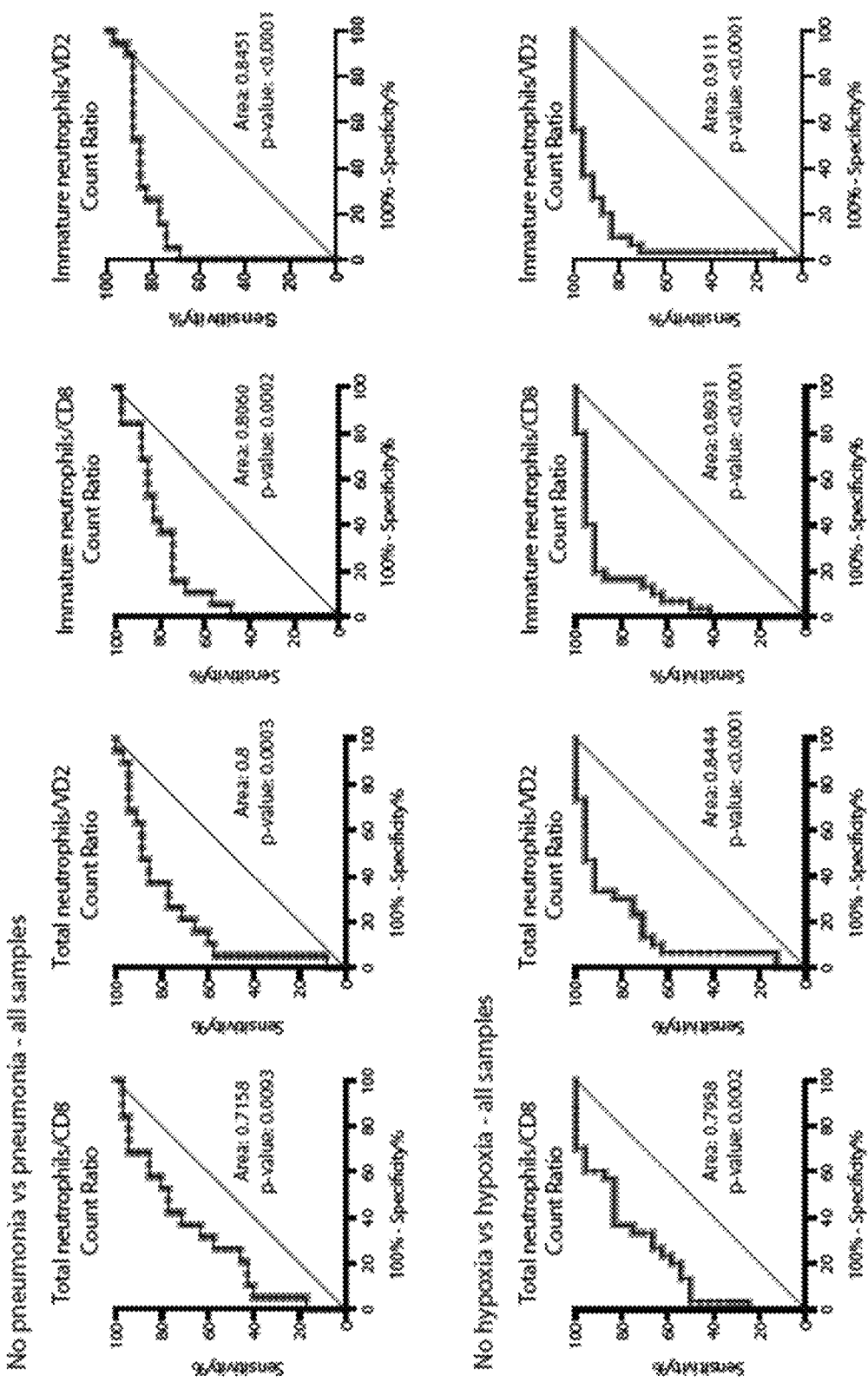
Figure 5B:
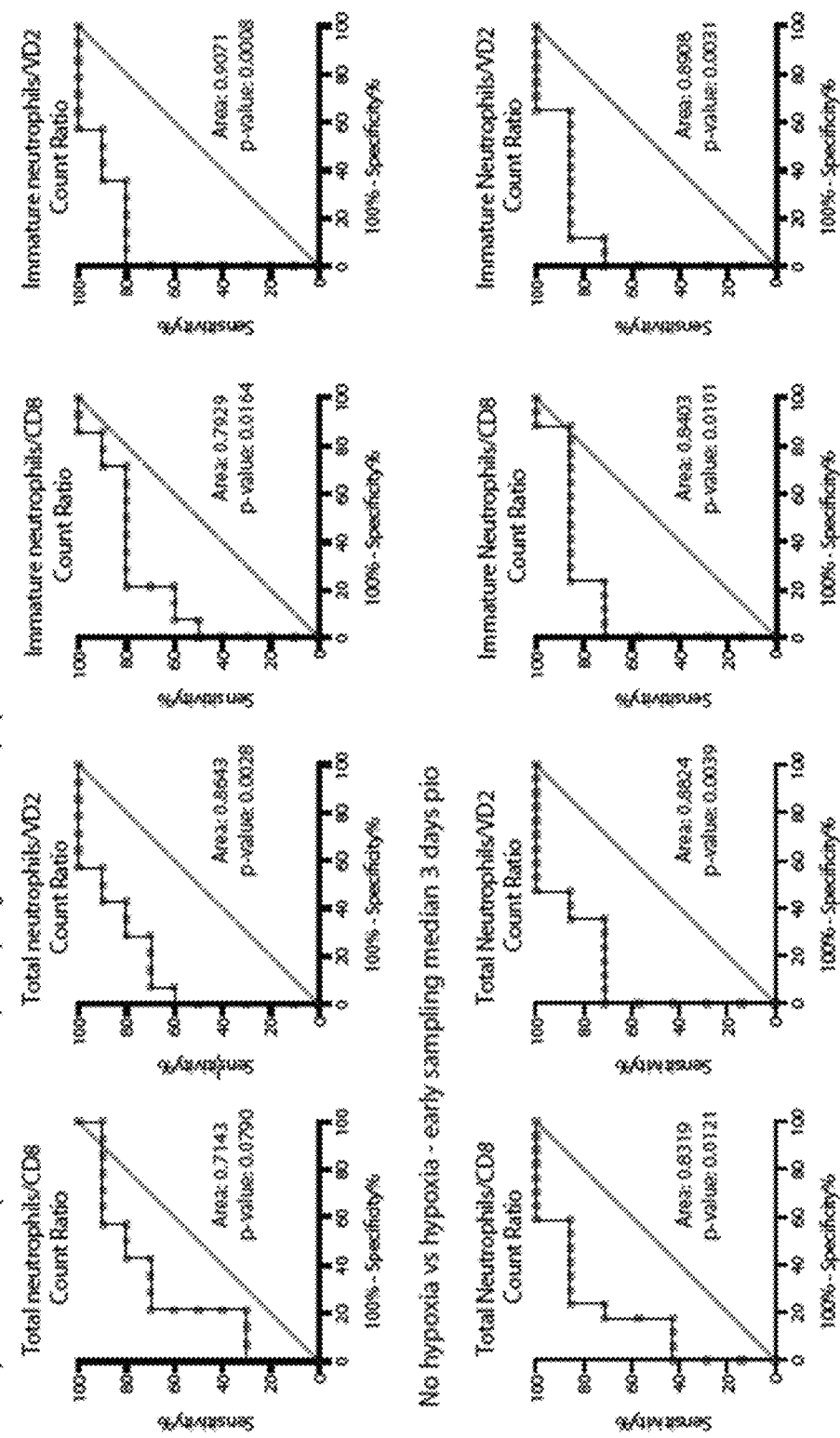

FIGS. 5A-5B Immature neutrophil to VD2 T-cell ratio is an early prognosis marker for pneumonia and hypoxia symptoms. FIG. 5A ROC curve analysis comparison was performed for pneumonia and hypoxia symptoms between absolute counts of total neutrophils to CD8 T-cell ratio, total neutrophils to VD2 T-cell, immature neutrophils to CD8 T-cell ratio, and immature neutrophils to VD2 T-cell ratio.

FIG. 5B Similar analysis was performed on a subset of early samples from the 54 acute patients (24 patients, 1 to 7 days pio with a median of 3 days pio). ROC curve was analysed using Wilson/Brown method. 95% confidence interval and standard error for panel B are given in Table 1. Data available in source data file.

FIG. 6A blood collection in CPT tubes affects phenotypic markers but not cell counts (n=5 healthy donors). Paired analysis was performed either with Wilcoxon non-parametric test for cell counts or ratio of paired t-test for gMFI.

Figure 6B:
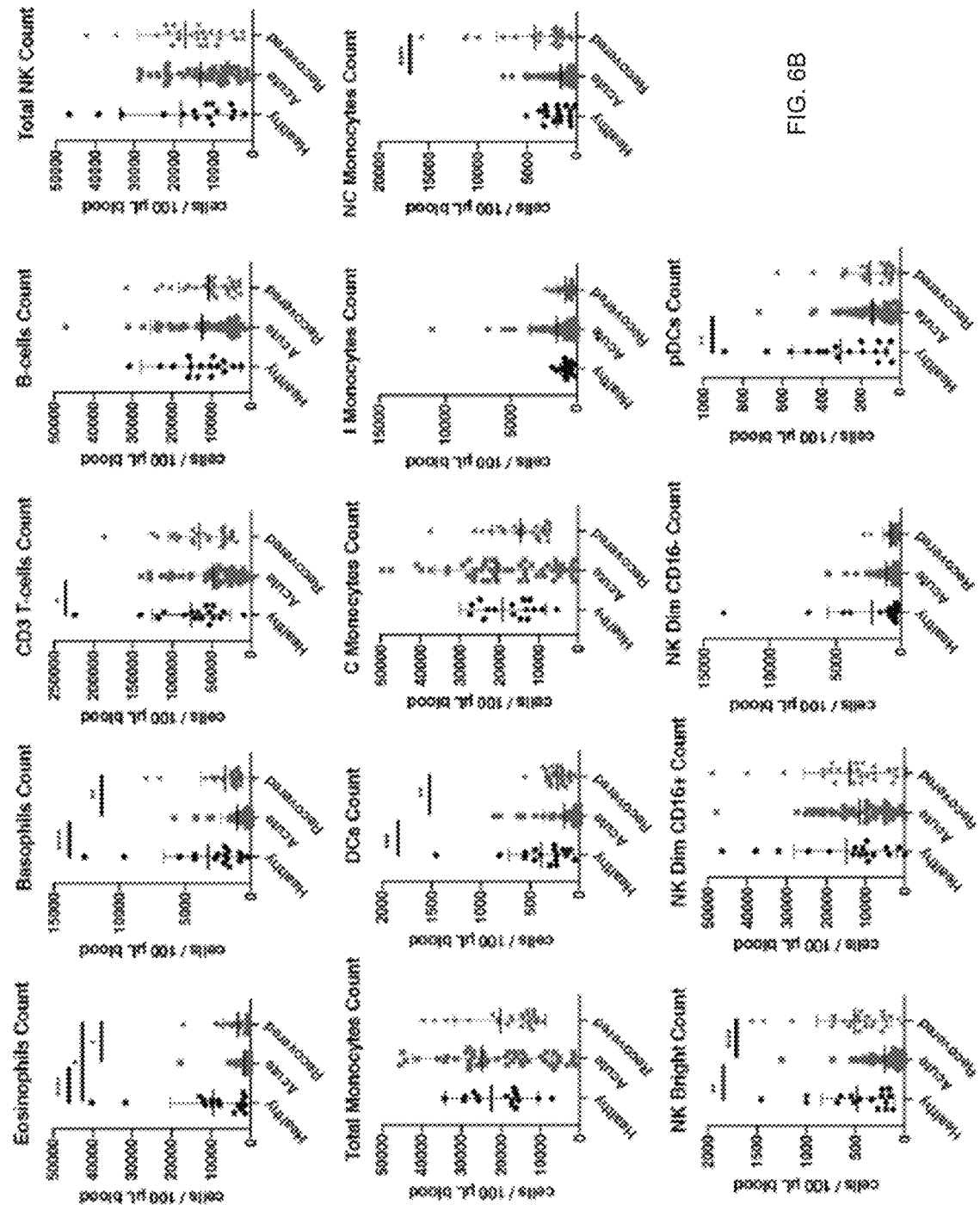

FIG. 6B Individual plot for heatmap of cell counts presented in FIG. 1B. Scatter dot plots are presented with mean±SD. Absolute counts were analysed by Kruskal-Wallis using Dunn correction for multiple comparison, gMFI was analysed by Brown-Forsythe and Welch anova without correction for multiple comparison. *p<0.05, p<0.01, *p<0.001.

Figure 7A:
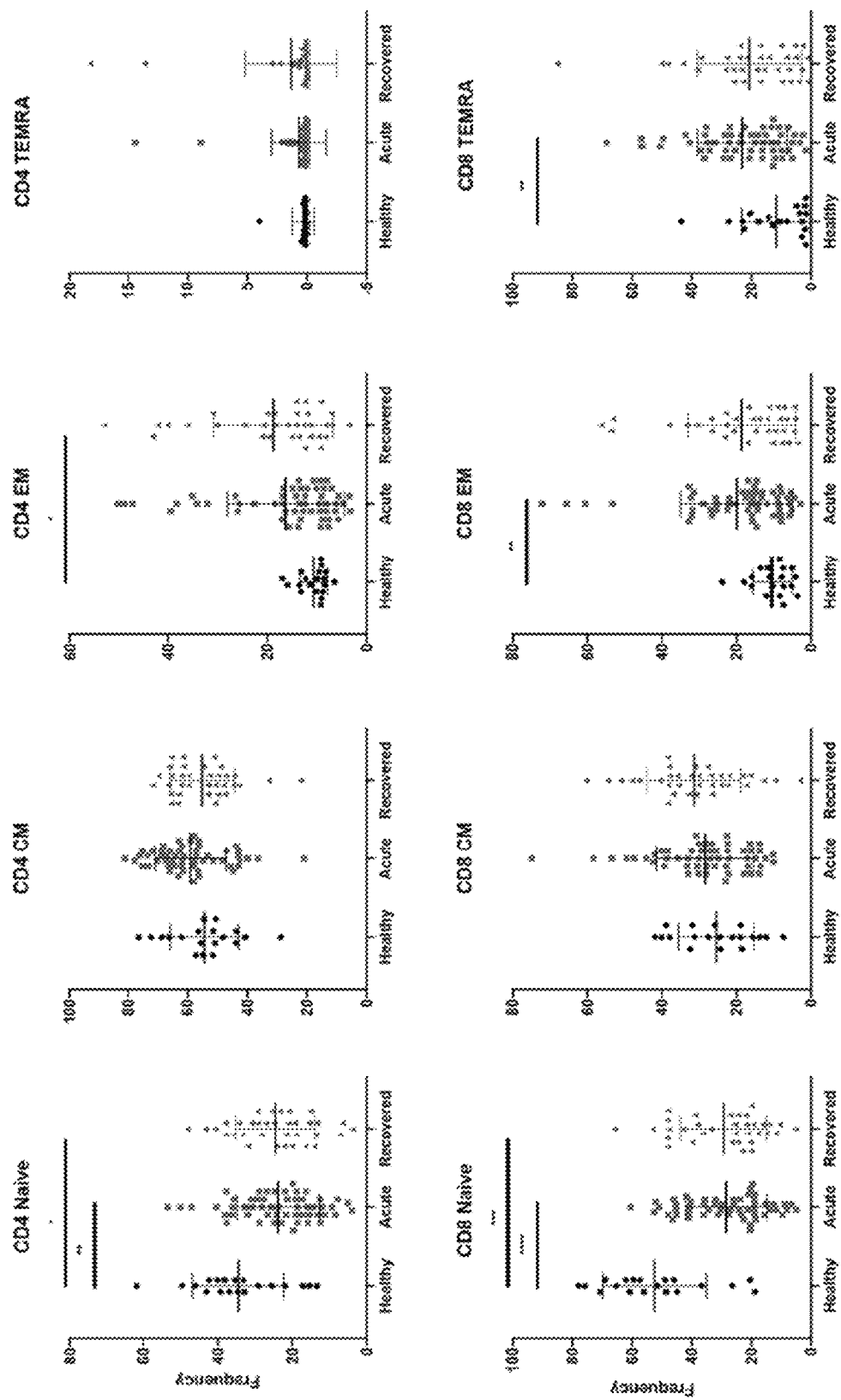
Figure 7B:
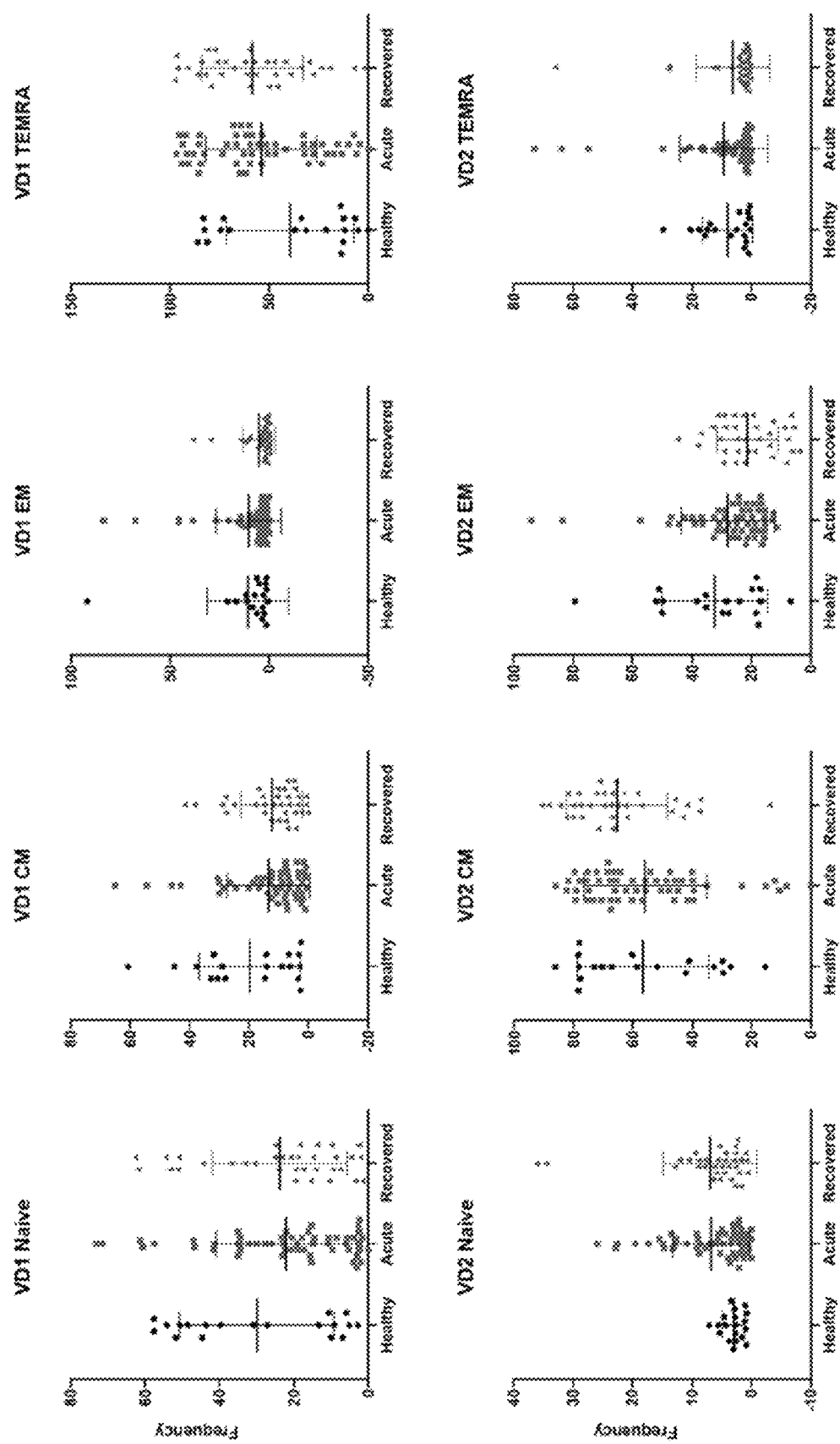

FIGS. 7A-B Individual plots for heatmap of FIGS. 2D1-2D2. Individual frequencies of CD45RA vs CD27 differentiation stage of CD8, CD4, VD1 and VD2 T-cells. Scatter dot plots are presented with mean±SD. Frequencies were analysed by Kruskal-Wallis using Dunn correction for multiple comparison. *p<0.05, p<0.01, *p<0.001

Figure 8A:
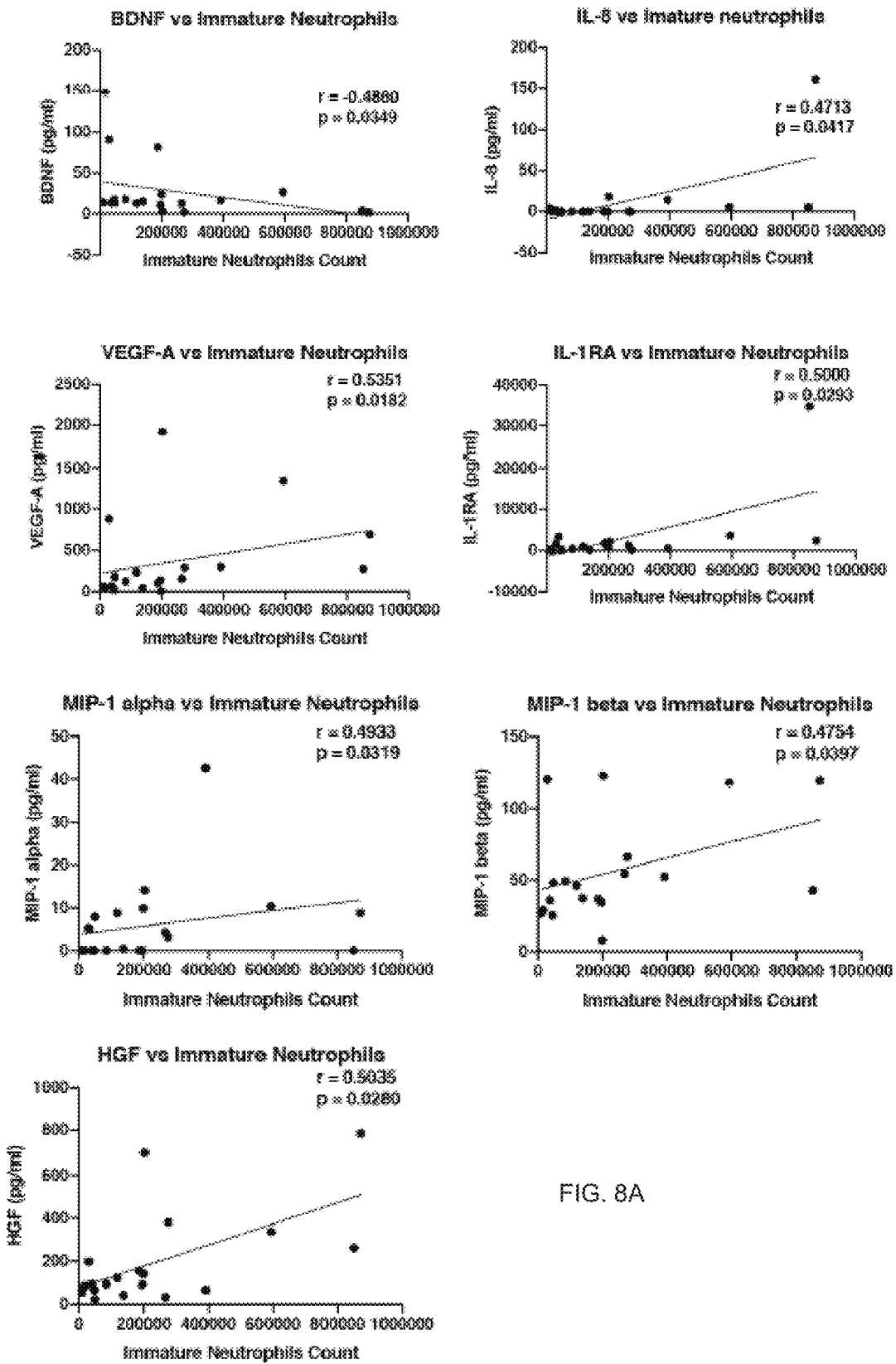
Figure 8B:
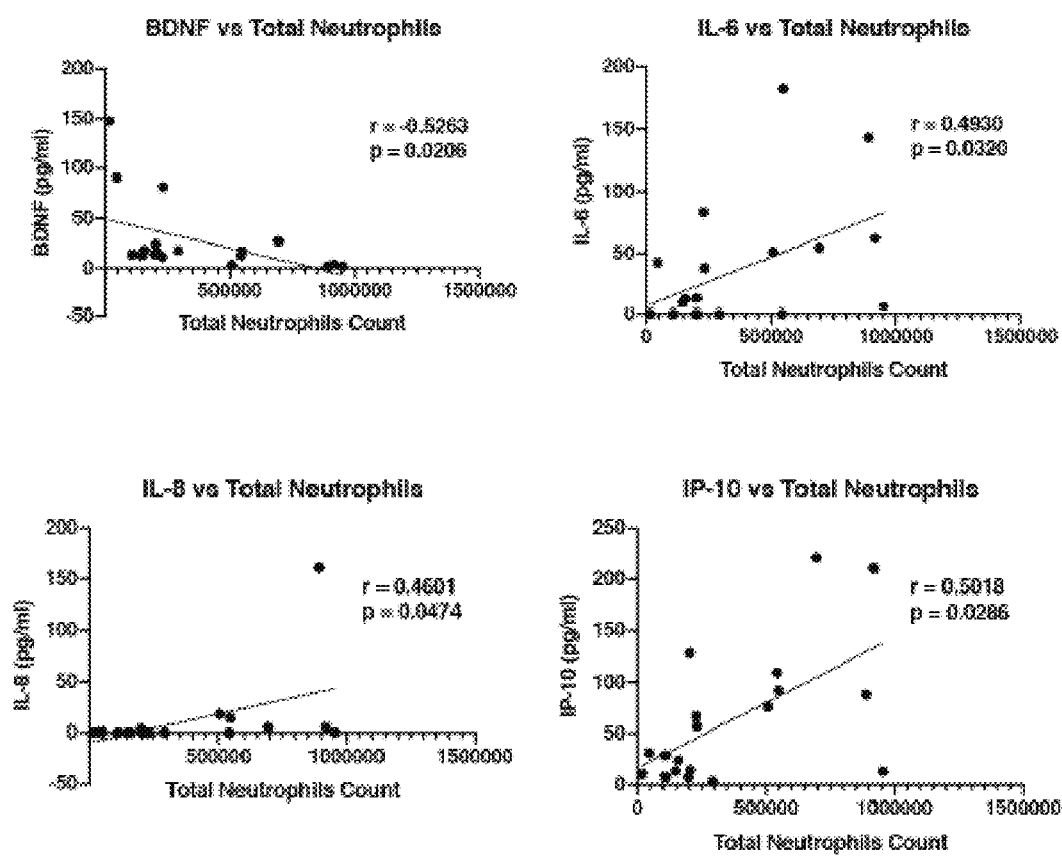
Figure 8C:
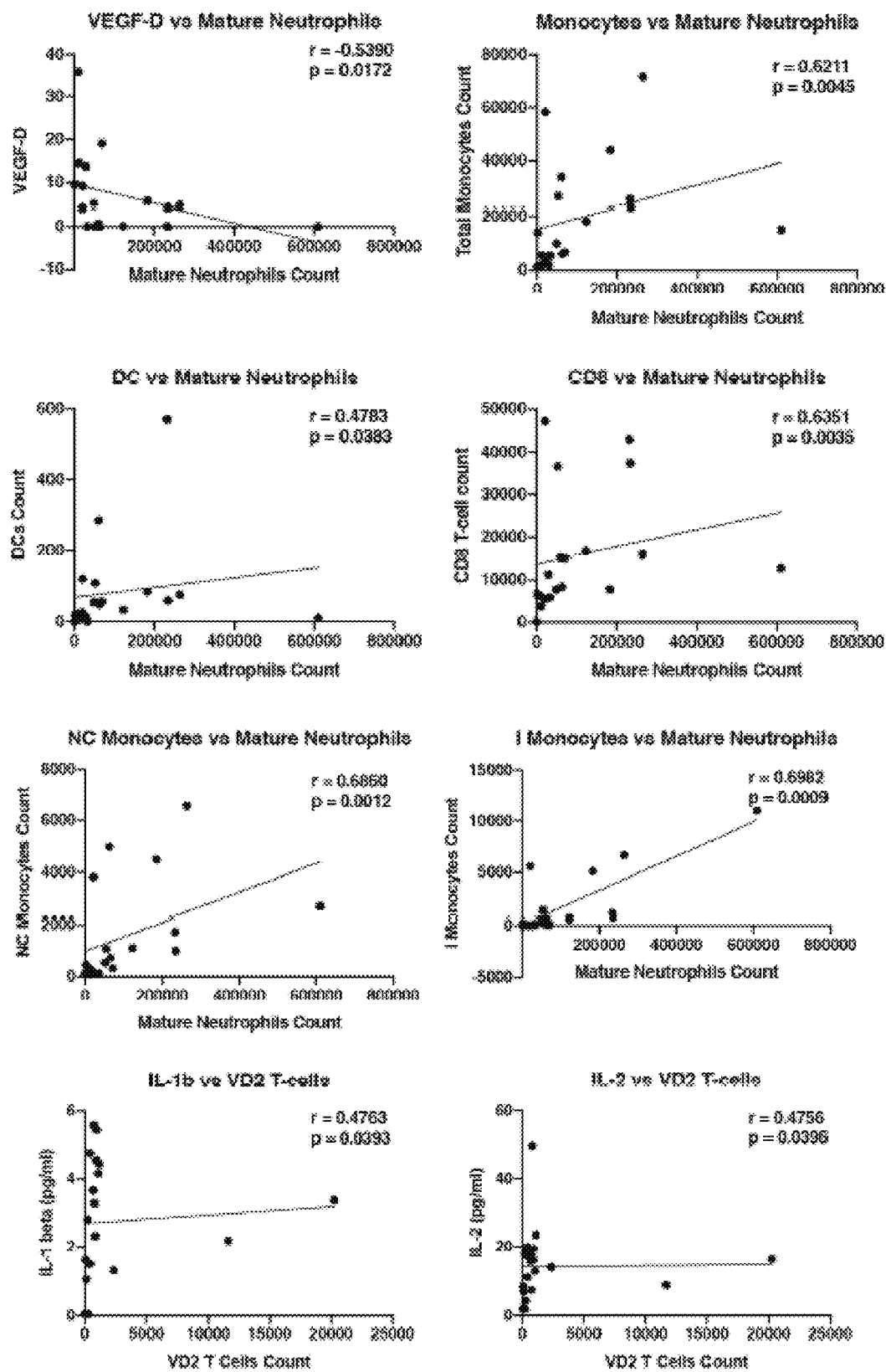

FIGS. 8A-8C Individual correlation plots for FIGS. 4A-B. Non-parametric Spearman test were performed for the parameters indicated in the plots for 19 patients that had paired Luminex plasma readings. FIG. 8A Individual plots of immature neutrophil counts with cytokines not presented in main FIG. 4B.

FIG. 8B Individual plots of immature neutrophil counts with cytokines.

Figure 8D:
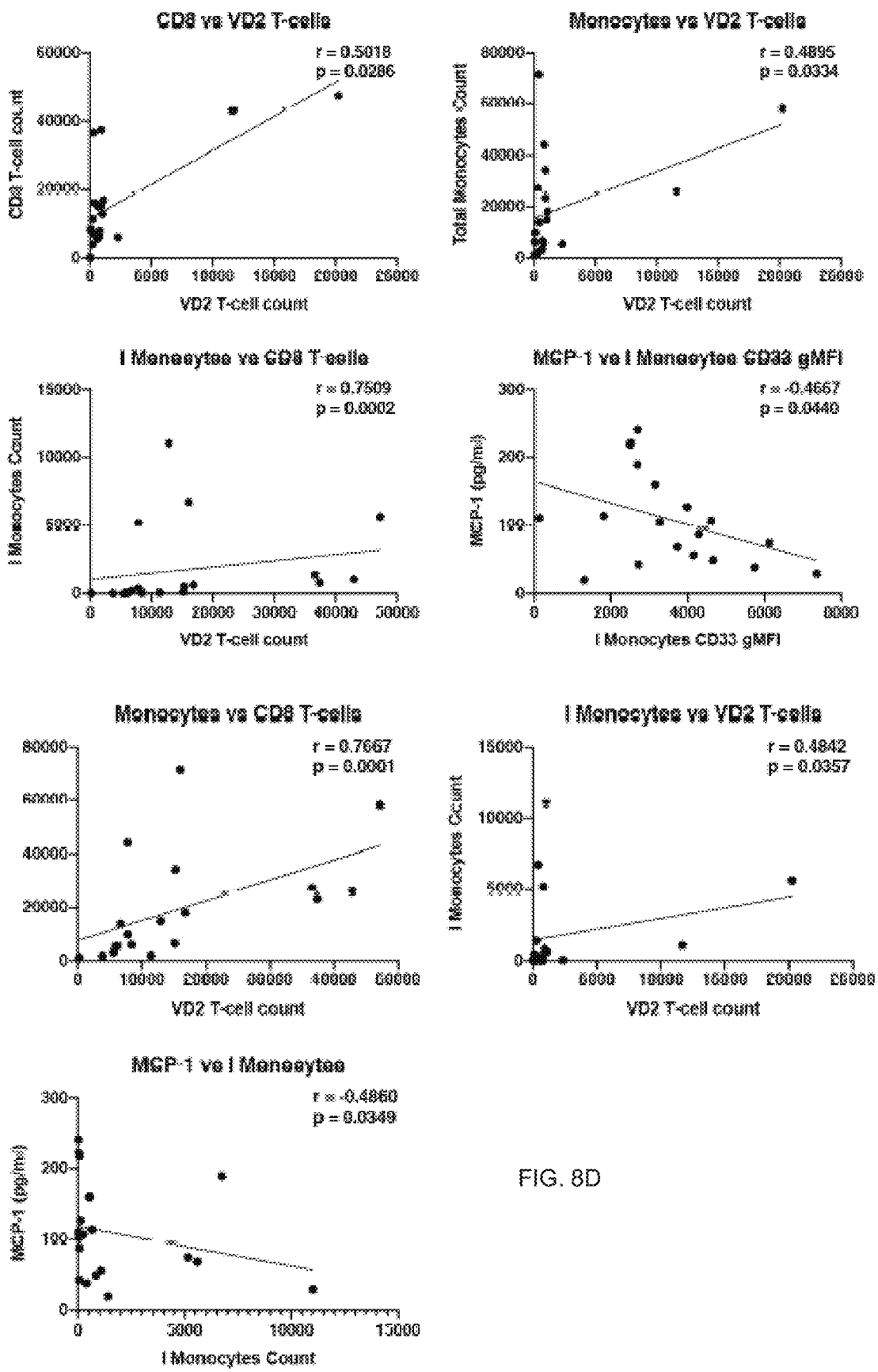

FIGS. 8C-8D correlations between other immune cells and cytokines. rho and p values of the correlations are indicated on the individual plots.

Figure 9A:
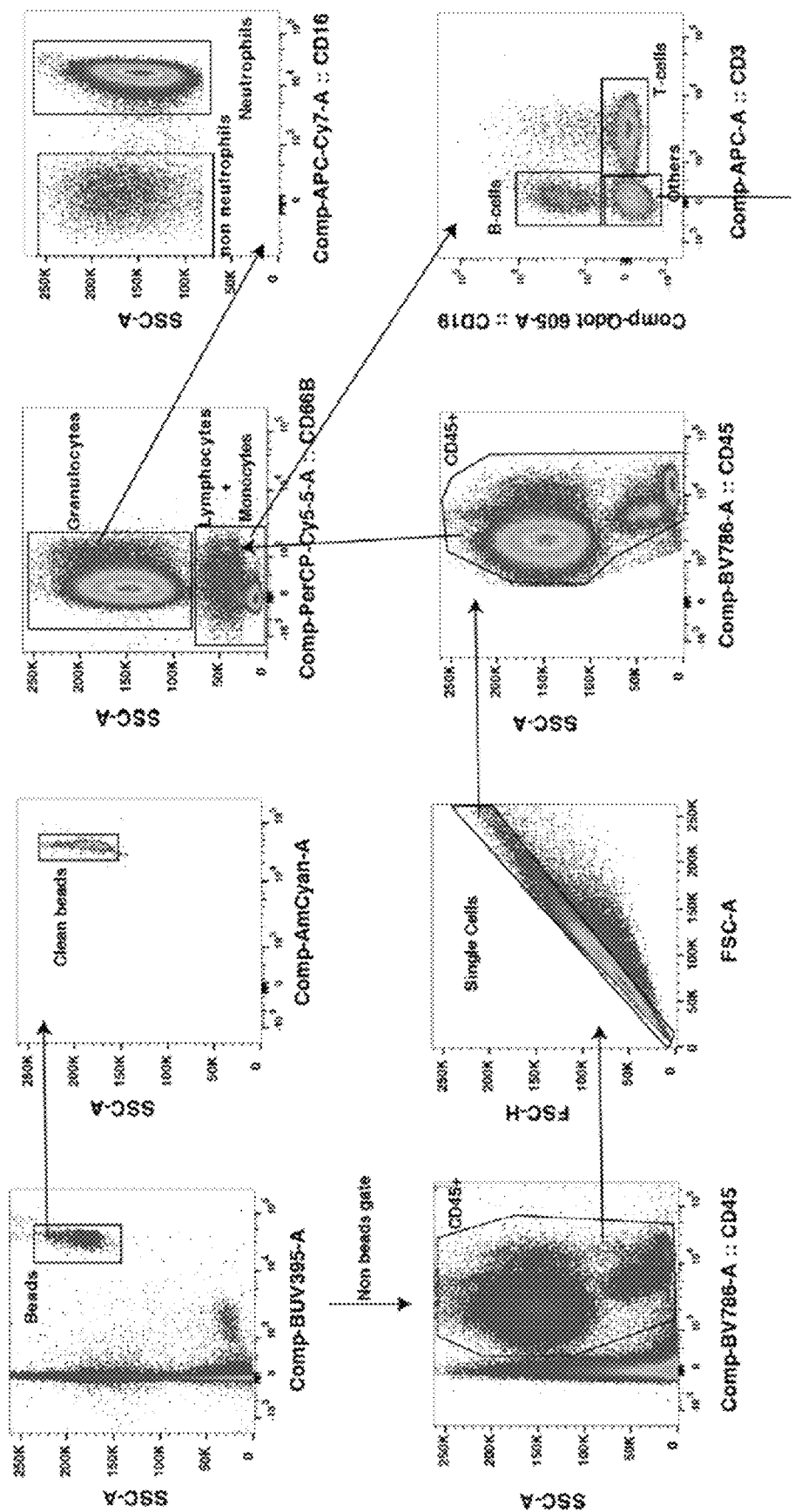
Figure 9:
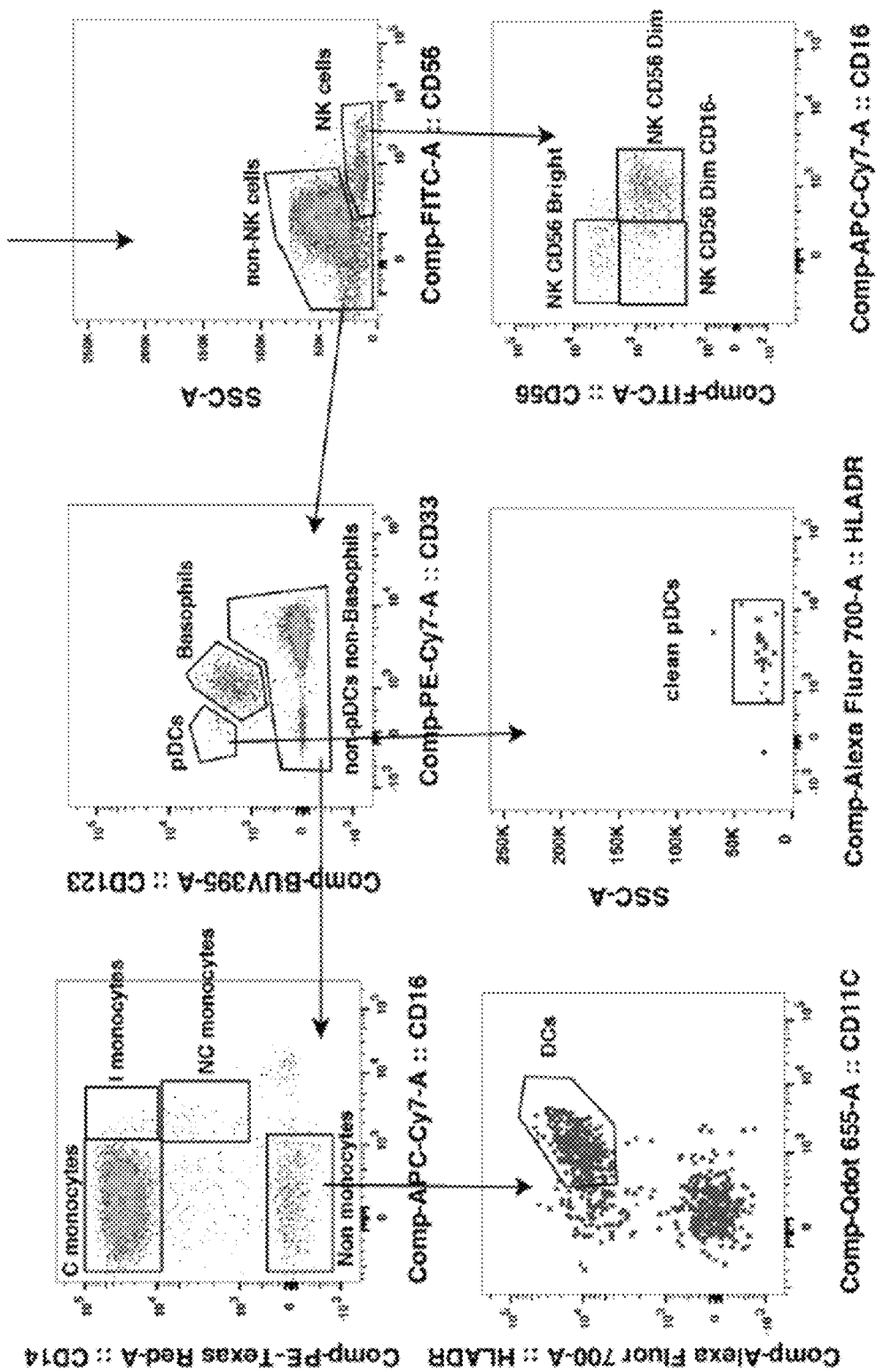

FIGS. 9A-B Gating strategy for flow cytometry panel A. 100 μL of blood was stained with the antibodies of panel A described in Table 4. Gating was performed after compensation adjustment in flowjo as presented in this figure.

Figure 10A:
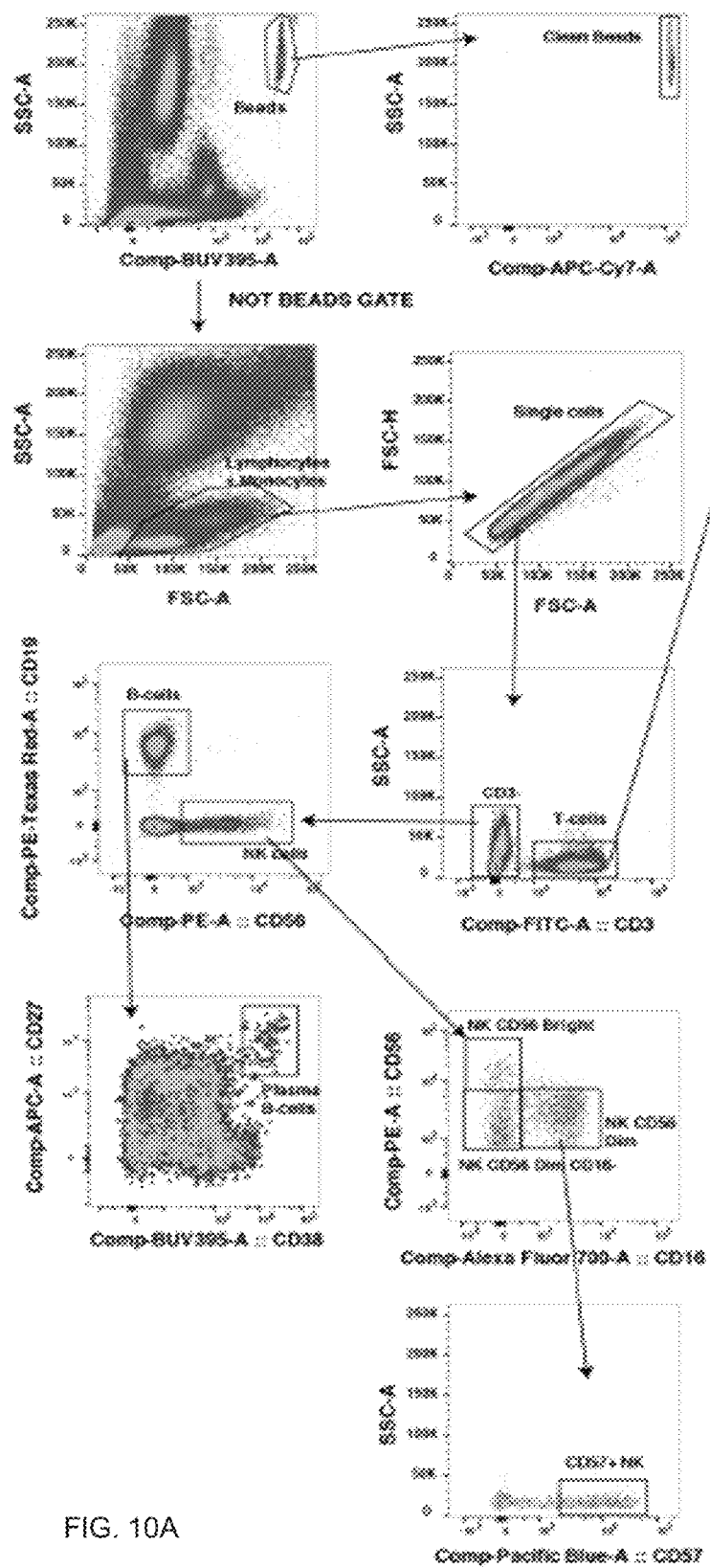
Figure 10B:
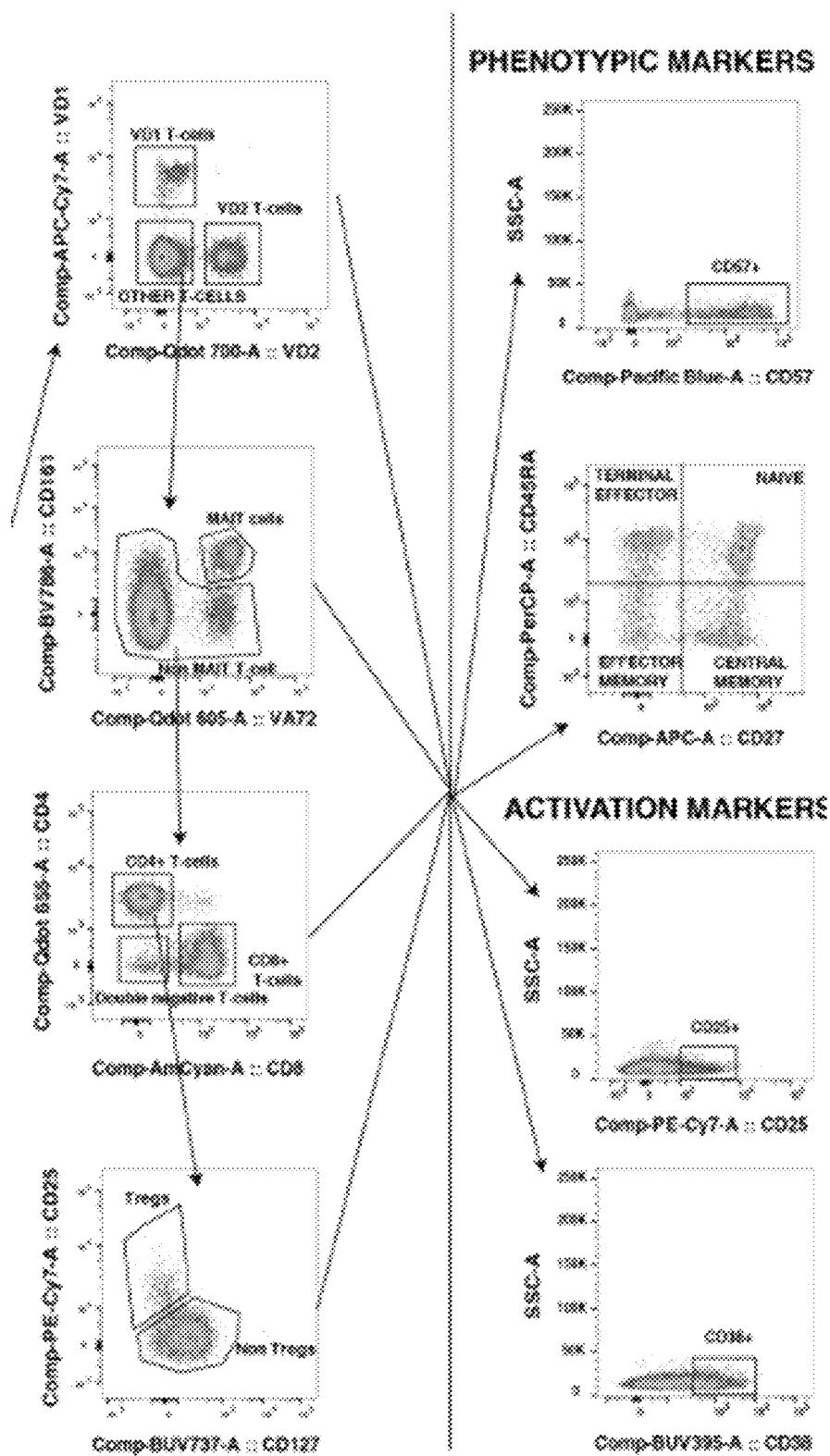

FIGS. 10A-B Gating strategy for flow cytometry panel B. 100 μL of blood was stained with the antibodies of panel B described in Table 4. Gating was performed after compensation adjustment in flowjo as presented in this figure.

Figure 11A:
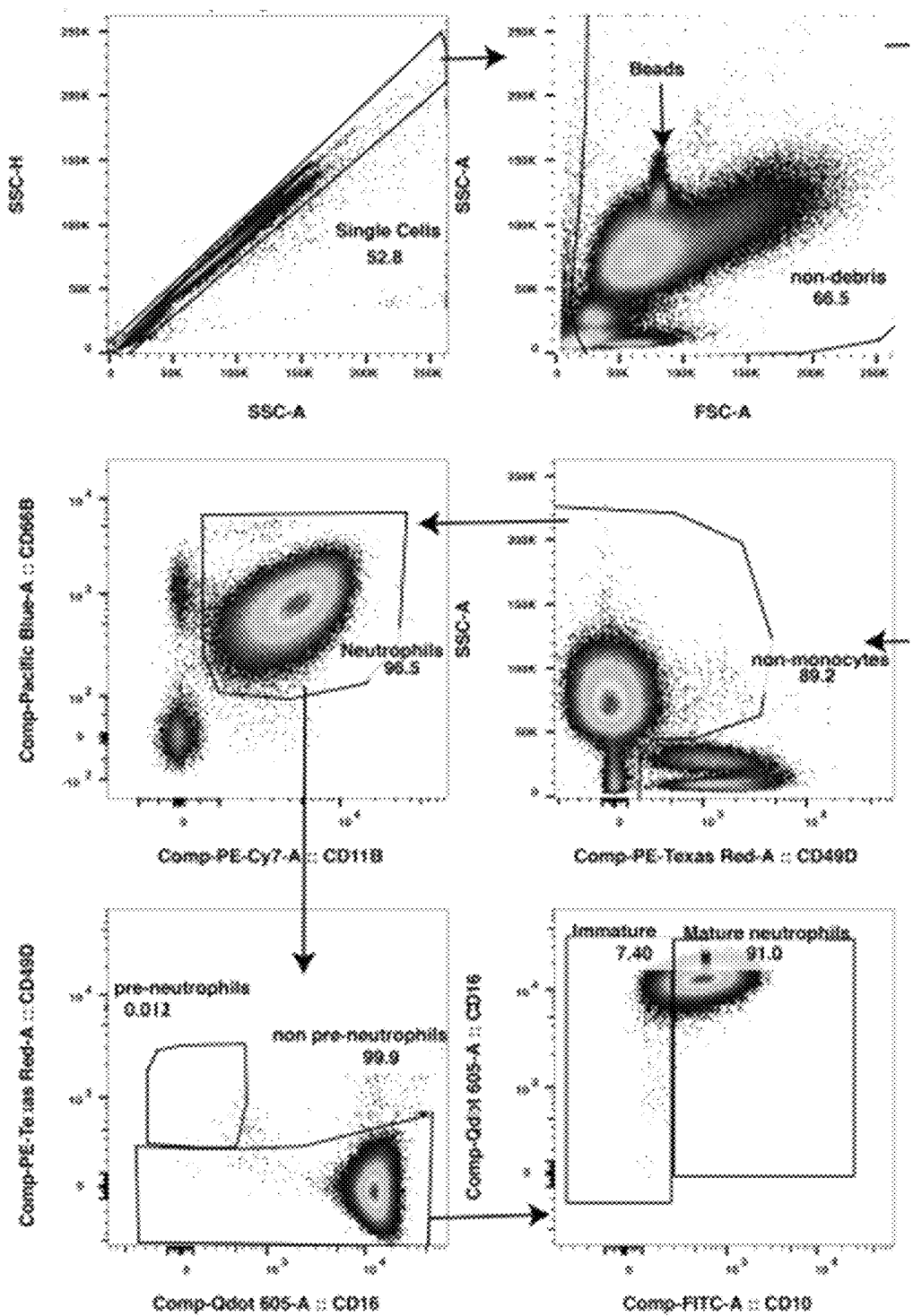
Figure 11B:
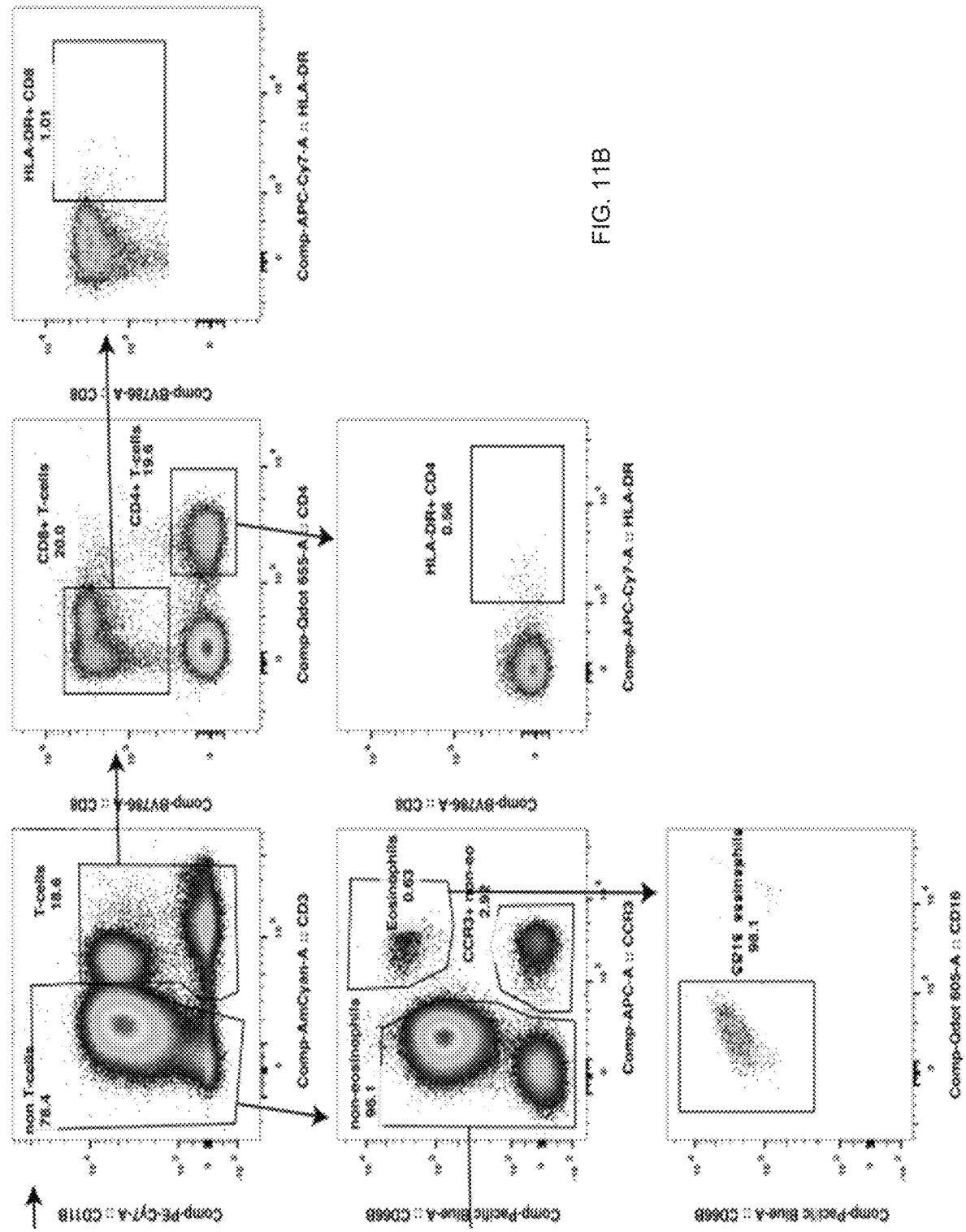
Figure 12A:
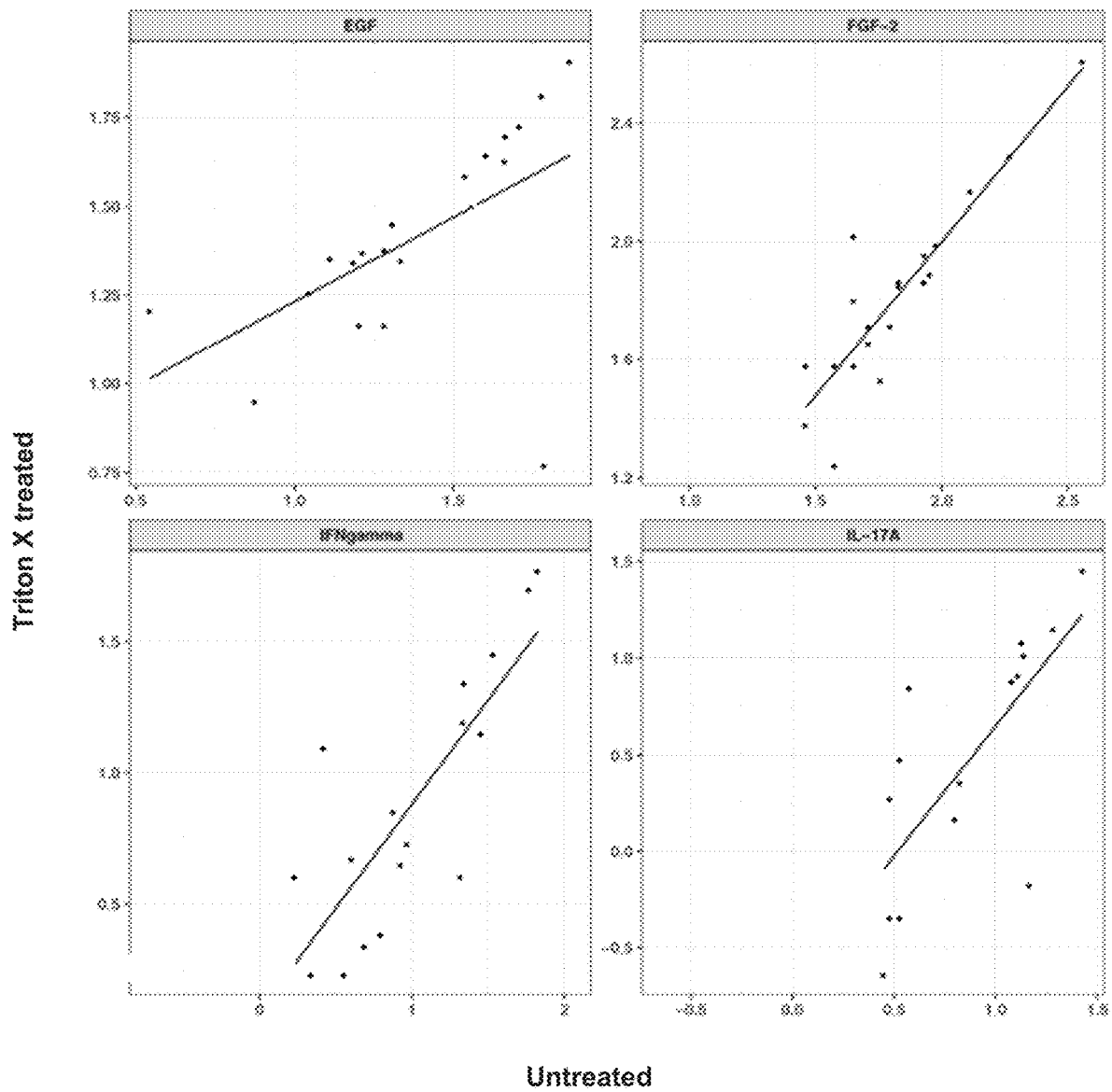
Figure 12B:
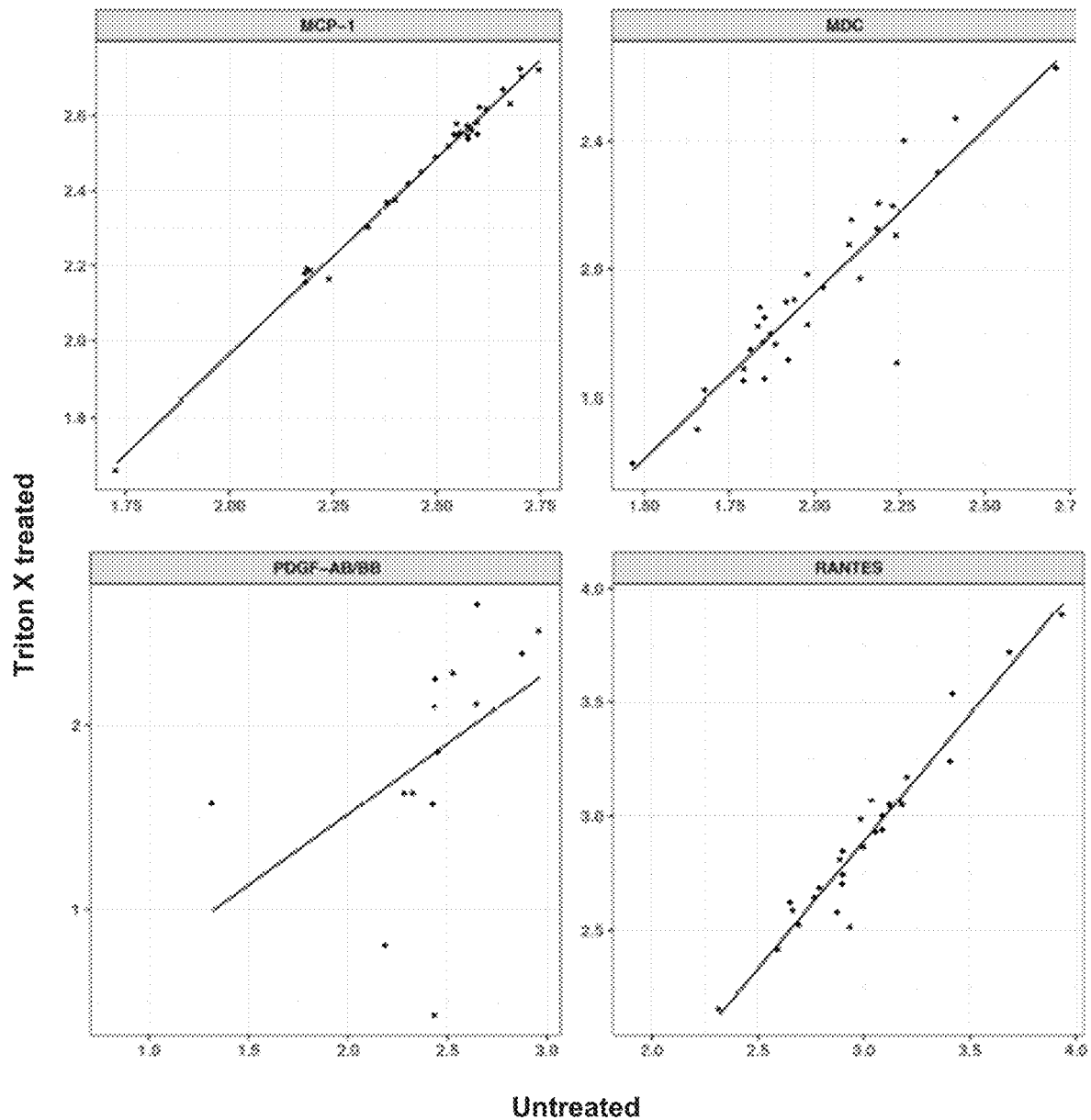
Figure 12C:
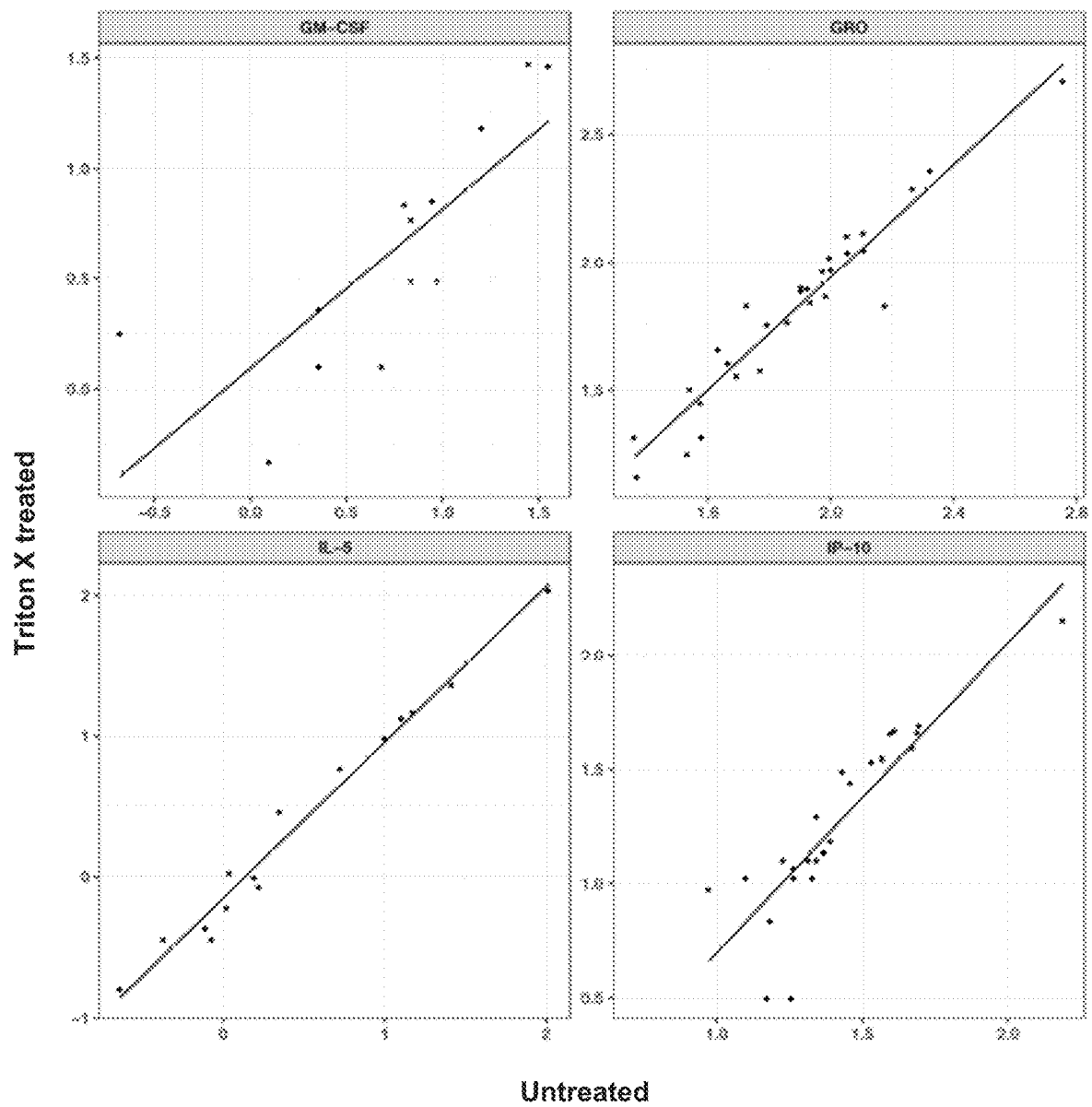
Figure 12D:
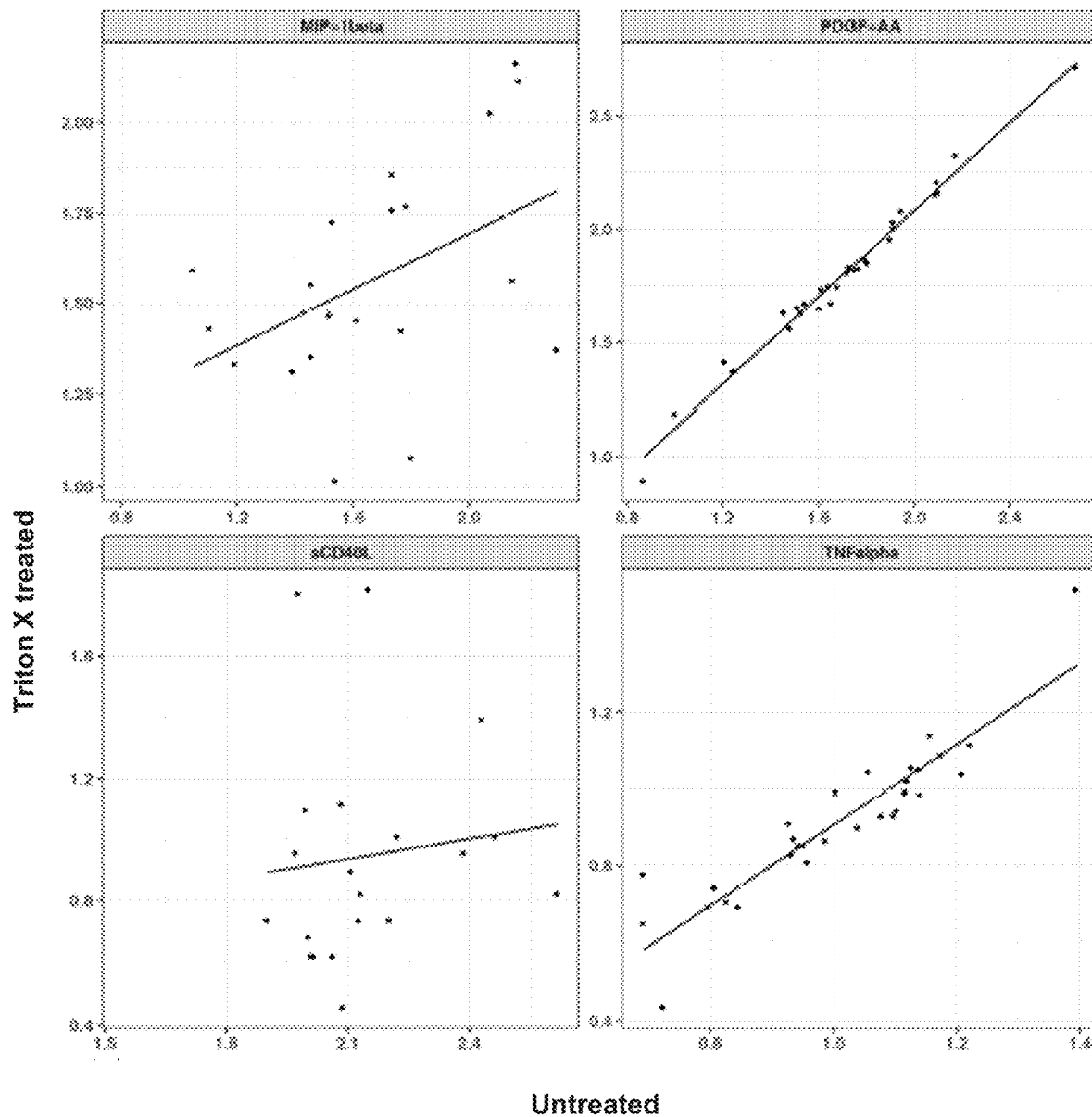

FIGS. 11A-B Gating strategy for flow cytometry panel C. 100 μL of blood was stained with the antibodies of panel C described in Table 3. Gating was performed after compensation adjustment in flowjo as presented in this figure.

FIGS. 12A-D Correlation of analytes detected by Luminex with or without Triton-X treatment in healthy donors. Pearson correlation plots.

FIG. 12E Pearson correlation p, r and $r^2$ values for the analytes with readings above the detection limit.

EXPERIMENTAL SECTION

Example 1

Material and Methods

Study Design

This was an observational cohort study of patients with PCR-confirmed COVID-19 who were admitted to the National Centre for Infectious Diseases, Singapore. All patients with COVID-19 in Singapore, regardless of the severity of infection, are admitted to isolation facilities until clinical recovery and viral clearance. Supportive therapy including supplemental oxygen and symptomatic treatment were administered as required. Pneumonia was diagnosed radiologically by interpretation of CXR or CT thorax images. Hypoxia is defined as requirement for supplemental oxygen, which was started if peripheral $O_2$ saturations ($SpO_2$) were <94%. Admission to ICU was reserved for those patients requiring [$FiO_2$]≥40% or with haemodynamic instability and included invasive mechanical ventilation when necessary. Incidence of thrombo-embolic and cardiac events are indicated in Table 2.

TABLE 2

Demographics and clinical outcomes of COVID-19 patients

| | Acute samples | | | | Recovered samples | | | |
|---|---|---|---|---|---|---|---|---|
| Variable | All patients (n = 54) | No pneumonia (n = 19) | Pneumonia without hypoxia (n = 11) | Pneumonia with hypoxia (n = 24) | All patients (n = 28) | No pneumonia (n = 7) | Pneumonia without hypoxia (n = 8) | Pneumonia with hypoxia (n = 13) |
| Demographics | | | | | | | | |
| Mean age, years | 51 (15) | 39 (8) | 53 (10) | 59 (16) | 49 (13) | 38 (14) | 51 (8) | 54 (12) |
| Sex, male (%) | 50 (98.0) | 18 (94.7) | 11 (100.0) | 21 (87.5) | 19 (67.9) | 4 (57.1) | 6 (75.0) | 9 (69.2) |
| Ethnicity (Chinese) | 21 (38.9) | 6 (31.6) | 4 (36.4) | 11 (45.8) | 21 (75.0) | 5 (71.4) | 7 (87.5) | 9 (69.2) |
| Any comorbidity (%) | 24 (44.4) | 5 (26.3) | 2 (18.2) | 15 (62.5) | 17 (60.7) | 3 (42.9) | 2 (25.0) | 12 (92.3) |
| Diabetes | 9 (16.7) | 1 (5.3) | 1 (9.1) | 6 (25.0) | 8 (28.6) | 0 (0.0) | 1 (12.5) | 7 (53.9) |
| Hypertension | 14 (25.9) | 3 (15.8) | 0 (0.0) | 11 (45.8) | 10 (35.7) | 0 (0.0) | 2 (25.0) | 8 (61.5) |
| Clinical outcome | | | | | | | | |
| Pneumonia with abnormal chest X ray (%) | 35 (64.8) | 0 (0.0) | 11 (100.0) | 24 (100.0) | 21 (75.0) | 0 (0.0) | 8 (100.0) | 13 (100.0) |
| Required supplemental oxygen (%) | 24 (44.4) | 0 (0.0) | 0 (0.0) | 24 (100.0) | 13 (46.4) | 0 (0.0) | 0 (0.0) | 13 (100.0) |
| ICU care (%) | 15 (27.8) | 0 (0.0) | 0 (0.0) | 15 (62.5) | 9 (32.1) | 0 (0.0) | 0 (0.0) | 9 (69.2) |

The values shown are based on available data. Categorical variables are shown as frequency (%). Continuous variables are shown mean (SD). ICU: intensive care unit.

Sample Size: No power analysis was done. Sample size was based on sample availability. Randomization: No randomization was done. Blinding: Clinical parameters were made available after data analysis.

Ethics Statement

Written informed consent was obtained from participants in accordance with the tenets of the Declaration of Helsinki. For COVID-19 blood/plasma collection, "A Multi-centred Prospective Study to Detect Novel Pathogens and Characterize Emerging Infections (The PROTECT study group)", a domain specific review board (DSRB) evaluated the study design and protocol, which was approved under study number 2012/00917. Healthy volunteers' samples were obtained under the following IRB "Study of blood cell subsets and their products in models of infection, inflammation and immune regulation" under the CIRB number 2017/2806 from SingHealth (Singapore).

Donor Information

Patients who tested PCR-positive for SARS-CoV-2 in a respiratory sample from February to April 2020 were recruited into the study[73]. Demographic data, days post disease onset date (unavailable for 5 asymptomatic patients), clinical score and SARS-CoV-2 RT-PCR results during the hospitalisation period were retrieved from patient clinical records. Relevant information is given in Table 2. Patients were classified in different clinical severity groups depending on the presence of pneumonia, hypoxia, and the need for ICU hospitalisation. For healthy volunteers, demographic data are provided in Table 3. Blood was collected in VACUETTE EDTA tubes (Greiner Bio, #455036) for healthy donors and acute patients, or Cell Preparation Tubes (CPT) (BD, #362761) for recovered patients. 100 μL of whole blood was extracted for each FACS staining panel (Table 4).

TABLE 3

Demographics of healthy controls

| Variable | Healthy Controls (n = 19) |
|---|---|
| Demographics | |
| Mean age, years | 36 (10) |
| Sex, male (%) | 10 (52.6) |
| Ethnicity (Chinese) | 12 (63.2) |

The values shown are based on available data. Categorical variables are shown as frequency (%). Continuous variables are shown mean (SD).

TABLE 4

Flow cytometry antibodies per panels

| No. | Marker | Colour | Volume (μL) | Clone | Cat. No. | Lot number | Vendor |
|---|---|---|---|---|---|---|---|
| Panel A (100 ul whole blood): | | | | | | | |
| 1 | CD45 | BV786 | 2.5 | HI30 | 304048 | B284678 | BioLegend |
| 2 | CD14 | PE-CF594 | 1.5 | MOP9 | 562335 | 9276099 | BD Biosciences |
| 3 | CD16 | APC Cy7 | 1.5 | 3G8 | 302018 | B288665 | BioLegend |

TABLE 4-continued

Flow cytometry antibodies per panels

| No. | Marker | Colour | Volume (µL) | Clone | Cat. No. | Lot number | Vendor |
|---|---|---|---|---|---|---|---|
| 4 | CD19 | SB600 | 2.5 | SJ25C1 | 63-0198-42 | 2179717 | eBioscience |
| 5 | CD11b | BV510 | 1.5 | ICRF44 | 563098 | 9346006 | BD Biosciences |
| 6 | CD33 | PE-Cy7 | 1 | WM-53 | 25-0338-42 | E10580-1456 | eBioscience |
| 7 | CD169 | PE | 1.5 | 7-239 | 346004 | B272223 | Biolegend |
| 8 | HLA-DR | AF700 | 1.5 | L243 | 307626 | B306020 | Biolegend |
| 9 | CD3 | APC | 1.5 | UCHT1 | 300439 | B205424 | Biolegend |
| 10 | CD56 | FITC | 5 | MEM-188 | 304604 | B291455 | Biolegend |
| 11 | CD11c | BV650 | 2.5 | B-ly6 | 563404 | 8187674 | BD Biosciences |
| 12 | CD86 | BV421 | 2 | 2331 | 562432 | 8337991 | BD Horizon |
| 13 | CD123 | BUV395 | 2 | 7G3 | 564195 | 9337379 | BD Horizon |
| 14 | CD66b | PerCP cy5.5 | 2 | G10F5 | 305108 | B204076 | Biolegend |
| Panel B (100 ul whole blood): | | | | | | | |
| 1 | CD3 | FITC | 1 | UCHT1 | 11-0038-42 | 2007254 | eBioscience |
| 2 | CD4 | BV650 | 2 | SK3 | 563875 | 9107661 | BD Horizon |
| 3 | CD8 | V500 | 2 | RPA-18 | 560774 | 4052849 | BD Biosciences |
| 4 | CD45RA | PerCP-Cy5.5 | 2 | HI100 | 304122 | B284187 | Biolegend |
| 5 | CD27 | APC | 2 | O323 | 17-0279-42 | 2168714 | eBioscience |
| 6 | CD25 | PE-Cy7 | 2 | M-A251 | 557741 | 9301660 | BD Biosciences |
| 7 | CD127 | BUV737 | 2 | HL-7R-M21 | 564300 | 9289985 | BD Biosciences |
| 8 | CD38 | BUV395 | 2 | HB7 | 563811 | 9155743 | BD Biosciences |
| 9 | CD56 | PE | 2 | AF12-7H3 | 130-098-755 | 5160830148 | Miltenyi Biotec |
| 10 | CD16 | AF700 | 2 | 3G8 | 302036 | B266048 | Biolegend |
| 11 | Vδ1 TCR | APC-Vio770 | 1 | REA173 | 130-120-438 | 5200304105 | Miltenyi Biotec |
| 12 | Vδ62 TCR | BV711 | 2 | B6 | 331412 | B285901 | Biolegend |
| 13 | VA7.2 TCR | BV605 | 2 | 3C10 | 351720 | B275819 | Biolegend |
| 14 | CD161 | BV786 | 2 | HP-3G10 | 339930 | B258781 | Biolegend |
| 15 | CD19 | PE-CF594 | 2 | HIB19 | 562321 | B277541 | BD Biosciences |
| 16 | CD57 | PB | 0.5 | HCD57 | 322316 | B270598 | Biolegend |
| Panel C (100 ul whole blood): | | | | | | | |
| 1 | CD45RA | PerCP Cy5.5 | 1 | HI100 | 304122 | B284187 | Biolegend |
| 2 | CD10 | FITC | 1 | HI10a | 312208 | B270343 | Biolegend |
| 3 | CD11b | PE-Cy7 | 1 | ICRF44 | 25-0118-42 | 1983204 | eBioscience |
| 4 | CD49d | PE-CF594 | 1 | 9F10 | 563645 | 9261644 | BD Biosciences |
| 5 | Siglec8 | PE | 1 | 7C9 | 347104 | B274554 | Biolegend |
| 6 | CD8 | BV786 | 0.5 | RPA-T8 | 563823 | 9344069 | BD Biosciences |
| 7 | CD4 | BV650 | 1 | RPA-T4 | 300536 | B292888 | Biolegend |
| 8 | CD16 | BV605 | 1 | 3G8 | 563172 | 9179026 | BD Horizon |
| 9 | CD3 | V500 | 5 | UCHT1 | 561416 | 9191445 | BD Biosciences |
| 10 | CD66b | BV421 | 1 | G10F5 | 562940 | 9308264 | BD Biosciences |
| 11 | HLA-DR | APC-H7 | 0.5 | G46-6 | 561358 | 9078946 | BD Biosciences |
| 12 | CCR3 | AF647 | 2 | 5E8 | 310710 | B220159 | Biolegend |
| 13 | CD38 | BUV395 | 3 | HB7 | 563811 | 9155743 | BD Biosciences |
| 14 | CD27 | BUV737 | 2 | L128 | 564301 | 9109918 | BD Biosciences |

Multiplex Microbead-Based Immunoassay

When available, plasma fraction was harvested after 20 minutes centrifugation at 1700×g of blood collected in BD Vacutainer CPT tubes (BD, #362761). Plasma samples were treated by solvent/detergent treatment with a final concentration of 1% Triton X-100 (Thermo Fisher Scientific, #28314) for virus inactivation at RT for 2 hours in the dark under stringent Biosafety laboratory 2+ conditions (approved by Singapore Ministry of Health)[74]. Cytokines detection in Triton-X treatment was compared with untreated samples for healthy donor and was found to be highly correlative for detected cytokines except for sCD40 (FIG. 12A-E). Immune mediator levels in COVID-19 patient plasma samples across acute samples were measured with by Luminex using the Cytokine/Chemokine/Growth Factor 45-plex Human ProcartaPlex™ Panel 1 (ThermoFisher Scientific, #EPX450-12171-901). Data acquisition was performed on FLEXMAP® 3D (Luminex) using xPONENT® 4.0 (Luminex) software. Data analysis was done on Bio-Plex Manager™ 6.1.1 (Bio-Rad). Standard curves were generated with a 5-PL (5-parameter logistic) algorithm, reporting values for both mean florescence intensity (MFI) and concentration data. Luminex data was generated from four different runs with each run having a number of samples which are common to the first run. For each subsequent run beyond the first, the mean of the common samples on each of the plates for each analyte was compared to the mean of the same samples in the first run to obtain a correction factor expressed in the following formula:

$$\text{correction\_factor} = \text{mean}(\text{common\_sample\_concentration\_in\_run1}) - \text{mean}(\text{common\_sample\_concentration\_in\_subsequent\_run}).$$

This correction factor was computed for each plate and analyte combination in the subsequent runs and added to the observed concentration to get the final normalised concentration. In the event that none of the common samples had concentration within the standard curve, no correction was done. Analyte concentrations were logarithmically transformed to ensure normality. Analytes that were not detectable in-patient samples were assigned the value of logarithmic transformation of Limit of Quantification (LOQ).

Flow Cytometry

Whole blood was stained with antibodies as stated in Table 4 (100 µL of whole blood per flow cytometry panel) for 20 minutes in the dark at RT. Samples were then supplemented with 0.5 mL of 1.2×BD FACS lysing solution (BD 349202). Final FACS lysing solution concentration taking into account volume in tube before addition is 1×. Samples were vortexed and incubated for 10 min at RT. 500 µL of PBS (Gibco, #10010-031) was added to wash the samples and centrifugated at 300×g for 5 min. Washing step of samples were repeated with 1 mL of PBS. Samples were then transferred to polystyrene FACS tubes containing 10 µL (10800 beads) of CountBright Absolute Counting Beads (Invitrogen, #36950). Samples were then acquired without delay, with vortexing before and every 3 min during acquisition to minimize fixed cell adherence to the tubes, using BD LSRII 5 laser configuration using automatic compensations and running BD FACS Diva Software version 8.0.1 (build 2014 07 03 11 47), Firmware version 1.14 (BDLSR II), CST version 3.0.1, PLA version 2.0. Analysis of flow cytometric data was performed with FlowJo version 10.6.1. Gating strategies for panels A, B and C are presented in FIGS. 9A-B, 10A-B and 11A-B respectively.

Statistical Analysis

Statistical analysis was performed using Prism 8 (Graph Pad Software, Inc). For comparisons of absolute cell counts or frequency, Kruskal-Wallis Test corrected with Dunn's method was performed. For comparisons of geometric Mean Fluorescence Intensity (gMFI) between three or more independent groups, Brown-Forsythe and Welch ANOVA using Dunnett T3 correction for multiple comparison was performed. For correlation analysis, spearman rank correlation was performed. p-values <0.05 for correlations, while adjusted p-values<0.05 for all the other comparisons were considered significant.

Data Analysis and UMAP Visualisation

UMAP: Gated cells were manually exported using FlowJo (Tree Star Inc.). Samples were then used for UMAP analysis using cytofkit2 R Packages with RStudio v3.5.2[75]. Five healthy, six acute and four recovered patients were each concatenated to its respective groups and 100000 cells were analysed using the ceil method. Custom R scripts were used to generate Z-score and correlation heatmaps.

Results

Circulating Myeloid Populations are Reduced in COVID-19 Patients

A total of 54 patients with laboratory-confirmed SARS-CoV-2 infection were recruited at the National Centre for Infectious Diseases (NCID), Singapore from end March to mid-May 2020 (Table 2). Blood was collected from 54 patients upon enrollment at a median 7 days post-illness onset (pio) (Table 2), from patients who had recovered from COVID-19 disease (median 30 days pio) (Table 2) and 19 healthy donors (Table 3). Unfortunately, only 11 patients had paired acquisition between acute and recovered which prevented meaningful paired analysis (Table 2). Immunophenotyping of whole blood samples was carried out with three distinct flow cytometry panels to analyse myeloid, granulocyte and lymphoid subsets. (FIG. 1A, Table 4). Each panel was supplemented with counting beads to allow accurate assessment of cell counts. 19 of the 54 acute patients had paired plasma samples that permitted quantification of immune mediators by Luminex multiplex microbead-based immunoassay. The cohort was strongly biased towards males, of which three patients experienced a thromboembolism event (5.6%) and two patients had fatal outcomes (3.7%).

First, the present study assessed using healthy donor samples, if the different blood collection method for recovered samples affected cell counts or activation markers. The inventors of the present disclosure observed that, while the cell count was not affected, expression of activation markers was affected on most cells but not CD38+ on T-cells (FIG. 6A), allowing direct comparison of activation markers only between healthy and acute samples. The FACS analysis revealed a declined cell count for eosinophils, basophils, total T-cells, dendritic cells (DCs), natural killer (NK) CD56 Bright, and plasmacitoid DCs (pDCs) in patients with acute COVID-19 infection (FIG. 1B, FIG. 6A). No significant changes were observed for B-cells, total monocytes, and total NK cells (FIG. 1B, FIG. 6A). Unbiased analysis by Uniform Manifold Approximation and Projection (UMAP) and graph based clustering however identified with CD169+ monocytes and CD11b$^{high}$ neutrophils, two additional clusters with high variation in acute patients (FIG. 1C). Further analysis showed that the monocytes presented with an increased expression of CD169 (strong type I interferon signature marker[17]), increased expression of CD11 b and HLA-DR, as well as CD33, a constitutive PI3K signaling inhibitor[18,19] (FIG. 1D, FIG. 6B) as compared to healthy donors.

Similar to the monocytes, neutrophils showed a significant upregulation of CD11b, CD66b, Siglec 8, CD38 and HLA-DR, suggesting that they were activated in response to SARS-CoV-2 infection (FIG. 1E,). Interestingly, despite this activation phenotype, an increase in the overall number of circulating neutrophils during acute SARS-CoV-2 infection based on conventional phenotypic markers (CD66b, CD11 b and CD16) was observed only in a small subset of our cohort (FIG. 1F). However, in-depth analysis of neutrophil subsets allows discrimination between immature (CD16$^{low/hihh}$ CD10$^-$) and mature (CD16$^{high}$CD10$^+$) subsets (FIG. 1G)[20-22]. Overall, a significant increase of immature neutrophil numbers was observed in acute patients as compared to healthy donors or recovered patients, while the number of mature neutrophils decreased (FIG. 1H).

CD8 and γδ T-Cell Populations are the Most Affected Lymphocyte Subsets

To better characterise COVID-19-induced lymphopenia, levels of CD8, CD4, γδ (i.e. VD1 and VD2), and mucosal-associated invariant T-cells (MAIT, CD3$^+$VA7.2$^+$CD161$^+$) were assessed during acute 146 infection. Results showed a decrease in circulating MAIT, CD8$^+$ and VD2 T-cells (FIG. 2A). However, circulating VD1 T-cells did not vary in numbers, and CD4$^+$ T-cells did not show a significant decrease during acute infection (FIG. 2A). Interestingly, levels of regulatory T-cells (Treg) and CD4$^+$CD161$^+$ T-cells increased in recovered patients as compared to acute patients (FIG. 2A).

Next, UMAP analysis was done on CD3$^+$ cells to visualise changes in differentiation states within the T-cell compartments (FIG. 2B). UMAP visualisation suggests that phenotypic modulation in the CD8$^+$ cluster was the most pronounced during SARS-CoV-2 infection (FIG. 2B). In order to validate this observation, CD45RA and CD27 markers were used to analyse the frequency of naïve (CD45RA$^+$CD27$^+$), central memory (CM, CD45RA$^-$CD27$^+$), effector memory (EM, CD45RA⁻CD27⁻) and terminal effector (TEMRA, CD45RA⁺CD27⁻) amongst the T-cell populations (FIG. 2C, FIG. 7A-B). In agreement with the UMAP analysis, CD8⁺ T-cells showed a change in differentiation profile from naïve in favour of EM and TEMRA (FIG. 2C). Noticeably, the frequency of naïve CD4⁺ T-cells decreased but was not reflected in a significant increase of a specific differentiated population (FIG. 2C).

In addition, UMAP analysis also suggested changes in VD1 and VD2 populations that were not reflected in terms of differentiation (FIG. 2B-C). Therefore, we investigated the expression of general activation marker CD38. In this context, we observed that all differentiation stages of CD8⁺ T-cells, VD1 and VD2, had higher expression of CD38 except VD2 TEMRA (FIG. 2D1-2D2). On the other hand, CD4⁺ T-cells did not show difference in the CD38 activation marker expression (FIG. 2D1-2D2). Together, our data suggest that while circulating cell counts were generally decreased for T-cells, SARS-CoV-2 differentially impacts the different T cell subsets in terms cell counts, differentiation and expression of CD38.

Granularity of Clinical Severity is Reflected by Immune Cell Counts

In order to associate the data with the clinical severity we separated the patients into four different groups: no pneumonia, pneumonia only, pneumonia and hypoxia, and pneumonia and hypoxia requiring ICU admission (FIG. 3A)[23,24]. This allowed estimation of cell counts in those groups and identification of markers that potentially depict disease severity. Consistent with previous studies on CD4 and CD8 lymphopenia[9,25,26] CD8⁺, CD4⁺, MAIT, VD1 and VD2 T-cells showed a gradual reduction in the peripheral blood with increasing disease severity (FIG. 3B). The effect was more pronounced for CD8⁺ and VD2 T-cells (FIG. 3B), suggesting a strong activation and infiltration of these cells in the lungs.

Cell counts in various myeloid subsets showed a similar decreasing profile with severity for pDCs, DCs, classical and intermediate monocytes (FIG. 3C). In contrast to cell counts, myeloid activation markers showed differential trends with severity (FIG. 3D). CD86 expression on DCs, HLA-DR and CD33 expression on monocytes followed a gradual decrease with increasing severity (FIG. 3D). Expression of CD169 on monocytes was decreased in ICU patients, while CD86 expression on pDCs was consistent across severity groups (FIG. 3D). Together, these results suggest that the remaining circulating monocytes and DCs in severe cases have a dysregulated phenotype.

While total circulating neutrophils showed no significant change with disease severity, neutrophilia was only observed in some patients with severe clinical complications (FIG. 3E). Particularly, there was a change in the composition of neutrophil subsets in accordance to disease severity, where an increase in the immature neutrophil cell count and frequency was accompanied with a decrease of mature neutrophils (FIG. 3E). These results suggest that immature neutrophils could reflect disease severity much more accurately than total neutrophil counts.

Immature Neutrophil Absolute Count Correlates with Cytokines

Neutrophil-to-Lymphocyte Ratio (NLR) or Neutrophil-to-CD8 T-cell Ratio (N8R) were proposed to be good diagnostic and prognostic markers for severe COVID-19 respiratory disease[26,27]. However, these studies observed increased neutrophils in severe cases which was not consistent with our observations and in another study[28] (FIG. 1F and FIG. 3E). To validate that the identified populations would be good markers of disease severity, a correlation analysis between analyte levels in available paired plasma samples (from CPT sodium citrate tubes) was performed with the cell counts obtained in FACS (from EDTA vacuette tubes)(FIG. 4A, FIG. 8A-C). Interestingly, strong correlation scores were observed between analytes and immature neutrophil counts (FIG. 4A, FIG. 8A), rather than with total neutrophil counts (FIG. 4A, FIG. 8B). The strongest correlations were observed between immature neutrophil counts and IL-6 (rho=0.6747, p=0.0015), and IP-10 (rho=0.7596, p=0.0002) (FIG. 9B).

In addition, strong correlations were also observed between mature neutrophils, monocytes and intermediate monocytes, as well as CD8 and VD2 T-cell counts (FIG. 8C). These results suggest that immature neutrophils counts can potentially be used as sensitive and reliable indicators of disease severity.

Immature Neutrophil to VD2 T-Cell Ratio as an Improved Prognostic Marker

The present study next assessed if an immature neutrophil-to-CD8 T-cells ratio (iN8R) or VD2 T cell counts ratio (iNVD2R) could be a better prognostic marker of disease severity as compared to the current proposed NLR and N8R[26,27]. To differentiate patients with and without pneumonia, iNVD2R performed better than N8R or iN8R with an area under receiver operating characteristic (AUROC) curve of 0.8451 (95% confidence interval CI: 0.7379-0.9523) vs 0.806 (95% CI: 0.6911-0.9210) and 0.7158 (95% CI: 0.5754-0.8562) respectively (FIG. 5A). In addition, to differentiate patients with and without hypoxia, an AUROC of 0.9111 (95% CI: 0.8306-0.9916) was obtained for iNVD2R as compared to 0.8931 (95% CI: 0.8044-0.9817) for iN8R and 0.7958 (95% CI: 0.6781-0.9136) for N8R. These results indicate that iNVD2R and iN8R could be good markers for severe respiratory disease.

To assess if this analysis could have predictive prognostic value in hospitalisation settings to improve patient management, we repeated the same analysis with only samples that were acquired at or before 7 days pio amongst the 54 acute patients (24 patients, median pio=3 days, range 1 to 7 days pio). AUROC for iNVD2R showed strong prognostic value for pneumonia onset (0.9071) as well as for onset of hypoxia (0.8908) (FIG. 5B, Table 1). The present data show that immature neutrophil counts are better in predicting disease severity as compared to total neutrophil counts. Importantly, they can be used in a ratio with CD8 or VD2 lymphocyte counts to improve the current N8R predictive ratio.

TABLE 1

ROC curve analysis for neutrophils to T-cell ratios in patients with pneumonia or hypoxia compared to those without as presented in FIG. 5B.

| Variable | Pneumonia | | | Hypoxia | | |
| --- | --- | --- | --- | --- | --- | --- |
| | AUC (95% CI) | Std. Error | p-value | AUC (95% CI) | Std. Error | p-value |
| Total neutrophils/CD8 T-cells | 0.7143 (0.4909-0.9377) | 0.1140 | 0.0790 | 0.8319 (0.6526-1) | 0.09149 | 0.0121 |
| Total neutrophils/VD2 T-cells | 0.8643 (0.7135-1) | 0.07694 | 0.0028 | 0.8824 (0.7239-1) | 0.08083 | 0.0039 |
| Immature neutrophils/CD8 T-cells | 0.7929 (0.5884-0.9973) | 0.1043 | 0.0164 | 0.8403 (0.6079-1) | 0.1186 | 0.0101 |
| Immature neutrophils/VD2 T-cells | 0.9071 (0.7754-1) | 0.06723 | 0.0008 | 0.8908 (0.7160-1) | 0.08915 | 0.0031 |

ROC analysis was performed on COVID-19 patients between 2 to 7 days pio (24 patients, median 3 days pio). ROC curve was built by plotting true positive rate (sensitivity) against false positive rate (100%-sensitivity) and AUC was calculated from the plot using the Wilson/Brown method. ROC, receiver operating characteristic; AUC, area under curve; CI, confidence interval; Std. Error, standard error.

Identification of Specific Immune Cells Modulated During Disease Severity

Three comprehensive flow cytometry panels were used on a cohort of 54 COVID-19 patients from the epidemic in Singapore. These panels allowed the identification of immature neutrophils (using CD66B or CD15 and SSC-A to gate neutrophils, followed by gating on CD16 and CD10) and VD2 T-cells (gated using CD3+VD2+) as the key immune cell populations showing changes in absolute cells count strongly associated with clinical severity such as pneumonia and hypoxia (FIG. 1A-H).

Identification of Immature Neutrophils to VD2 Ratio as an Improved Prognostic Marker The present study next compared the ratio of immature neutrophil counts to VD2 T-cell counts to the main known method of severity prognosis proposed in the literature (total neutrophils to CD8 ratio) and observed that the proposed immature neutrophil to VD2 ratio is more specific and sensitive as a potential prognostic marker for clinical severity (FIG. 5A). The time frame at which this marker would be important for prognosis was assessed. In a subgroup of patients that were sampled at a median of 3 days post illness onset (pio; range 1-7 days pio), the inventors of the present disclosure observed that the immature neutrophil to VD2 ratio is still a more accurate prognostic marker of symptoms progression (FIG. 5B).

The technology consists of a 6-colour flow cytometry panel for whole blood staining, containing anti-human CD45 (to separate immune cells from the rest of the blood products), anti-human CD3 (to identify T-cells), anti-human VD2 (to identify VD2 T-cells as the CD45$^+$ CD3$^+$ VD2$^+$ population), anti-human CD66b or CD15 (to identify granulocytes), anti-human CD16 and anti-human CD10 to distinguish mature neutrophils (CD16$^{high}$ CD10$^+$) from immature neutrophils (CD45$^+$CD3$^-$ CD66b/CD15$^+$ CD16$^{intermediate/-}$ CD10$^-$ population) in the granulocyte population. All these antibodies are coupled to standard fluorophores that are compatible with each other and with standard flow cytometers.

The antibody mix is prepared as a full stain version containing the 6 antibodies and counting beads (to allow accurate absolute counts), as well as a full stain minus one (FMO) containing all the antibodies except anti-human CD10) and no counting beads. These antibodies and counting beads can be supplied either individually or premixed either as a solution or lyophilized.

The use of the FMO mix allows for correct quantification of the CD10 marker in the full stain acquisition. It can be performed for each patient or once before each acquisition batch. The full stain mix allows for accurate counting of immature neutrophils defined as the CD45$^+$ CD3$^-$ CD66b/CD15$^+$ SSC-A$^{high}$ CD16$^{intermediate/-}$ and CD10$^-$ population, as well as the VD2 T-cell count defined as the CD45$^+$ CD3$^+$ SSC-A$^{low}$ VD2$^+$ population.

An extended version of the antibody mixes can be offered for use with 7 colour flow cytometry by also including anti-human CD8 antibody. This will allow quantification of CD8 T-cell counts of the patient (gated as CD45$^+$ CD3$^+$ CD8$^+$), which would allow the additional calculation of the prognostic ratio total neutrophils to CD8, as well as the immature neutrophil to CD8 ratio. The inventors identified this immature neutrophils to CD8 ratio as a better prognostic marker than the total neutrophils to CD8 ratio but less specific or sensitive when compared to the immature neutrophil to VD2 ratio since CD8 T-cells do not vary with age (see Application).

Example 2 i. Prognostic Kit would Contain the Following Lyophilized Mixes:

Mix 1 (full stain): counting beads and the following fluorophore tagged antibodies: antibody anti-human CD45, antibody anti-human CD66b or CD15, anti-human CD16, anti-human CD10, anti-human CD3, anti-human VD2, and the optional anti-human CD8.

Mix 2 (full stain minus one): the following fluorophore tagged antibodies: antibody anti-human CD45, antibody anti-human CD66b or CD15, anti-human CD16, anti-human CD3, anti-human VD2, and the optional anti-human CD8.

ii. Workflow Steps:
1. Patient blood is collected in EDTA (or other anticoagulant) containing tube.
2. 100 μL of blood is pipetted into Mix 1 and 100 μL of blood is pipetted into Mix 2, and incubation is performed for 20 min at room temperature in the dark.
3. 500 μL of a fixation agent and red blood cell agent is added to the tube and incubated 10 min for inactivation.

4. Samples can then be acquired on a flow cytometer.
5. Flow cytometry analysis is performed to gate the counting beads, the true immature neutrophils (using the Mix 1 and Mix 2 difference on CD10 color to gate true CD10 signal), the VD2 T-cells and optionally the CD8 T-cells. Counting beads count acquired by flow versus the number of beads originally in the mix is used to determinate the absolute number of immature neutrophils, VD2 T-cells and optionally CD8 T-cells in 100 µL of patient blood.
6. Clinicians (or automatic analysis software) can calculate the ratio of Immature neutrophils to VD2 ratio for the patient, and optionally the immature neutrophils to CD8 ratio.
7. Clinician can refer to the patient ratio in context of the ROC data (attached—please refer to section iii & iv) to evaluate the patient risk of developing pneumonia and/or hypoxia from the coronavirus infection.
8. Hospitalization and/or pre-emptive treatment for the patient will be determined by the clinician.

iii. ROC Data for Immature Neutrophils to VD2 Ratio:

TABLE 5

Immature neutrophils to VD2 ratio early time point. No hypoxia vs hypoxia

| Ratio | Sensitivity % | 95% CI | Specificity % | 95% CI | Likelihood ratio |
|---|---|---|---|---|---|
| >4.875 | 100 | 64.57% to 100.0% | 5.882 | 0.3017% to 26.98% | 1.063 |
| >6.394 | 100 | 64.57% to 100.0% | 11.76 | 2.090% to 34.34% | 1.133 |
| >9.408 | 100 | 64.57% to 100.0% | 17.65 | 6.191% to 41.03% | 1.214 |
| >11.94 | 100 | 64.57% to 100.0% | 23.53 | 9.555% to 47.26% | 1.308 |
| >12.42 | 100 | 64.57% to 100.0% | 29.41 | 13.28% to 53.13% | 1.417 |
| >12.85 | 100 | 64.57% to 100.0% | 35.29 | 17.31% to 58.70% | 1.545 |
| >13.00 | 85.71 | 48.69% to 99.27% | 35.29 | 17.31% to 58.70% | 1.325 |
| >13.35 | 85.71 | 48.69% to 99.27% | 41.18 | 21.61% to 63.99% | 1.457 |
| >16.95 | 85.71 | 48.69% to 99.27% | 47.06 | 26.17% to 69.04% | 1.619 |
| >21.40 | 85.71 | 48.69% to 99.27% | 52.94 | 30.96% to 73.83% | 1.821 |
| >23.33 | 85.71 | 48.69% to 99.27% | 58.82 | 36.01% to 78.39% | 2.082 |
| >26.02 | 85.71 | 48.69% to 99.27% | 64.71 | 41.30% to 82.69% | 2.429 |
| >29.87 | 85.71 | 48.69% to 99.27% | 70.59 | 46.87% to 86.72% | 2.914 |
| >37.64 | 85.71 | 48.69% to 99.27% | 76.47 | 52.74% to 90.44% | 3.643 |
| >43.83 | 85.71 | 48.69% to 99.27% | 82.35 | 58.97% to 93.81% | 4.857 |
| >79.36 | 85.71 | 48.69% to 99.27% | 88.24 | 65.66% to 97.91% | 7.286 |
| >117.4 | 71.43 | 35.89% to 94.92% | 88.24 | 65.66% to 97.91% | 6.071 |
| >138.7 | 71.43 | 35.89% to 94.92% | 94.12 | 73.02% to 99.70% | 12.14 |
| >179.3 | 71.43 | 35.89% to 94.92% | 100 | 81.57% to 100.0% | |
| >409.5 | 57.14 | 25.05% to 84.18% | 100 | 81.57% to 100.0% | |
| >723.3 | 42.86 | 15.82% to 74.95% | 100 | 81.57% to 100.0% | |
| >829.2 | 28.57 | 5.077% to 64.11% | 100 | 81.57% to 100.0% | |
| >2198 | 14.29 | 0.7328% to 51.31% | 100 | 81.57% to 100.0% | |

TABLE 5-continued

Immature neutrophils to VD2 ratio early time point. No hypoxia vs hypoxia

| Ratio | Sensitivity % | 95% CI | Specificity % | 95% CI | Likelihood ratio |
|---|---|---|---|---|---|

TABLE 6

Immature neutrophils to VD2 ratio early time point. No pneumonia vs pneumonia

| Ratio | Sensitivity % | 95% CI | Specificity % | 95% CI | Likelihood ratio |
|---|---|---|---|---|---|
| >4.875 | 100 | 72.25% to 100.0% | 7.143 | 0.3664% to 31.47% | 1.077 |
| >6.394 | 100 | 72.25% to 100.0% | 14.29 | 2.538% to 39.94% | 1.167 |
| >9.408 | 100 | 72.25% to 100.0% | 21.43 | 7.571% to 47.59% | 1.273 |
| >11.94 | 100 | 72.25% to 100.0% | 28.57 | 11.72% to 54.65% | 1.4 |
| >12.42 | 100 | 72.25% to 100.0% | 35.71 | 16.34% to 61.24% | 1.556 |
| >12.85 | 100 | 72.25% to 100.0% | 42.86 | 21.38% to 67.41% | 1.75 |
| >13.00 | 90 | 59.58% to 99.49% | 42.86 | 21.38% to 67.41% | 1.575 |
| >13.35 | 90 | 59.58% to 99.49% | 50 | 26.80% to 73.20% | 1.8 |
| >16.95 | 90 | 59.58% to 99.49% | 57.14 | 32.59% to 78.62% | 2.1 |
| >21.40 | 90 | 59.58% to 99.49% | 64.29 | 38.76% to 83.66% | 2.52 |
| >23.33 | 80 | 49.02% to 96.45% | 64.29 | 38.76% to 83.66% | 2.24 |
| >26.02 | 80 | 49.02% to 96.45% | 71.43 | 45.35% to 88.28% | 2.8 |
| >29.87 | 80 | 49.02% to 96.45% | 78.57 | 52.41% to 92.43% | 3.733 |
| >37.64 | 80 | 49.02% to 96.45% | 85.71 | 60.06% to 97.46% | 5.6 |
| >43.83 | 80 | 49.02% to 96.45% | 92.86 | 68.53% to 99.63% | 11.2 |
| >79.36 | 80 | 49.02% to 96.45% | 100 | 78.47% to 100.0% | |
| >117.4 | 70 | 39.68% to 89.22% | 100 | 78.47% to 100.0% | |
| >138.7 | 60 | 31.27% to 83.18% | 100 | 78.47% to 100.0% | |
| >179.3 | 50 | 23.66% to 76.34% | 100 | 78.47% to 100.0% | |
| >409.5 | 40 | 16.82% to 68.73% | 100 | 78.47% to 100.0% | |
| >723.3 | 30 | 10.78% to 60.32% | 100 | 78.47% to 100.0% | |
| >829.2 | 20 | 3.554% to 50.98% | 100 | 78.47% to 100.0% | |
| >2198 | 10 | 0.5129% to 40.42% | 100 | 78.47% to 100.0% | |

TABLE 7

Immature neutrophils to VD2 ratio all time points. No hypoxia vs hypoxia

| Ratio | Sensitivity % | 95% CI | Specificity % | 95% CI | Likelihood ratio |
|---|---|---|---|---|---|
| >3.869 | 100 | 86.20% to 100.0% | 3.333 | 0.1710% to 16.67% | 1.034 |
| >4.155 | 100 | 86.20% to 100.0% | 6.667 | 1.185% to 21.32% | 1.071 |

TABLE 7-continued

Immature neutrophils to VD2 ratio all time points. No hypoxia vs hypoxia

| Ratio | Sensitivity % | 95% CI | Specificity % | 95% CI | Likelihood ratio |
|---|---|---|---|---|---|
| >4.445 | 100 | 86.20% to 100.0% | 10 | 3.460% to 25.62% | 1.111 |
| >5.164 | 100 | 86.20% to 100.0% | 13.33 | 5.310% to 29.68% | 1.154 |
| >6.120 | 100 | 86.20% to 100.0% | 16.67 | 7.337% to 33.56% | 1.2 |
| >6.609 | 100 | 86.20% to 100.0% | 20 | 9.505% to 37.31% | 1.25 |
| >6.883 | 100 | 86.20% to 100.0% | 23.33 | 11.79% to 40.93% | 1.304 |
| >7.879 | 100 | 86.20% to 100.0% | 26.67 | 14.18% to 44.45% | 1.364 |
| >10.33 | 100 | 86.20% to 100.0% | 30 | 16.66% to 47.88% | 1.429 |
| >11.94 | 100 | 86.20% to 100.0% | 33.33 | 19.23% to 51.22% | 1.5 |
| >12.09 | 100 | 86.20% to 100.0% | 36.67 | 21.87% to 54.49% | 1.579 |
| >12.48 | 100 | 86.20% to 100.0% | 40 | 24.59% to 57.68% | 1.667 |
| >12.85 | 100 | 86.20% to 100.0% | 43.33 | 27.38% to 60.80% | 1.765 |
| >13.00 | 95.83 | 79.76% to 99.79% | 43.33 | 27.38% to 60.80% | 1.691 |
| >13.35 | 95.83 | 79.76% to 99.79% | 46.67 | 30.23% to 63.86% | 1.797 |
| >15.04 | 95.83 | 79.76% to 99.79% | 50 | 33.15% to 66.85% | 1.917 |
| >18.39 | 95.83 | 79.76% to 99.79% | 53.33 | 36.14% to 69.77% | 2.054 |
| >21.40 | 95.83 | 79.76% to 99.79% | 56.67 | 39.20% to 72.62% | 2.212 |
| >23.33 | 95.83 | 79.76% to 99.79% | 60 | 42.32% to 75.41% | 2.396 |
| >25.22 | 95.83 | 79.76% to 99.79% | 63.33 | 45.51% to 78.13% | 2.614 |
| >26.80 | 91.67 | 74.15% to 98.52% | 63.33 | 45.51% to 78.13% | 2.5 |
| >27.60 | 91.67 | 74.15% to 98.52% | 66.67 | 48.78% to 80.77% | 2.75 |
| >29.87 | 91.67 | 74.15% to 98.52% | 70 | 52.12% to 83.34% | 3.056 |
| >35.46 | 91.67 | 74.15% to 98.52% | 73.33 | 55.55% to 85.82% | 3.438 |
| >41.24 | 87.5 | 69.00% to 95.66% | 73.33 | 55.55% to 85.82% | 3.281 |
| >43.83 | 87.5 | 69.00% to 95.66% | 76.67 | 59.07% to 88.21% | 3.75 |
| >48.30 | 87.5 | 69.00% to 95.66% | 80 | 62.69% to 90.49% | 4.375 |
| >56.33 | 83.33 | 64.15% to 93.32% | 80 | 62.69% to 90.49% | 4.167 |
| >61.17 | 83.33 | 64.15% to 93.32% | 83.33 | 66.44% to 92.66% | 5 |
| >62.88 | 83.33 | 64.15% to 93.32% | 86.67 | 70.32% to 94.69% | 6.25 |
| >77.21 | 83.33 | 64.15% to 93.32% | 90 | 74.38% to 96.54% | 8.333 |
| >102.6 | 79.17 | 59.53% to 90.76% | 90 | 74.38% to 96.54% | 7.917 |
| >117.4 | 75 | 55.10% to 88.00% | 90 | 74.38% to 96.54% | 7.5 |
| >122.9 | 75 | 55.10% to 88.00% | 93.33 | 78.68% to 98.82% | 11.25 |
| >141.3 | 70.83 | 50.83% to 85.09% | 93.33 | 78.68% to 98.82% | 10.63 |
| >179.3 | 70.83 | 50.83% to 85.09% | 96.67 | 83.33% to 99.83% | 21.25 |
| >232.3 | 66.67 | 46.71% to 82.03% | 96.67 | 83.33% to 99.83% | 20 |
| >273.1 | 62.5 | 42.71% to 78.84% | 96.67 | 83.33% to 99.83% | 18.75 |
| >292.8 | 58.33 | 38.83% to 75.53% | 96.67 | 83.33% to 99.83% | 17.5 |
| >304.0 | 54.17 | 35.07% to 72.11% | 96.67 | 83.33% to 99.83% | 16.25 |
| >329.6 | 50 | 31.43% to 68.57% | 96.67 | 83.33% to 99.83% | 15 |
| >359.6 | 45.83 | 27.89% to 64.93% | 96.67 | 83.33% to 99.83% | 13.75 |
| >384.4 | 41.67 | 24.47% to 61.17% | 96.67 | 83.33% to 99.83% | 12.5 |
| >443.6 | 37.5 | 21.16% to 57.29% | 96.67 | 83.33% to 99.83% | 11.25 |
| >492.5 | 33.33 | 17.97% to 53.29% | 96.67 | 83.33% to 99.83% | 10 |
| >539.0 | 29.17 | 14.91% to 49.17% | 96.67 | 83.33% to 99.83% | 8.75 |
| >597.1 | 25 | 12.00% to 44.90% | 96.67 | 83.33% to 99.83% | 7.5 |
| >723.3 | 20.83 | 9.245% to 40.47% | 96.67 | 83.33% to 99.83% | 6.25 |
| >829.2 | 16.67 | 6.679% to 35.85% | 96.67 | 83.33% to 99.83% | 5 |
| >972.0 | 12.5 | 4.344% to 31.00% | 96.67 | 83.33% to 99.83% | 3.75 |
| >1778 | 12.5 | 4.344% to 31.00% | 100 | 88.65% to 100.0% | |
| >3004 | 8.333 | 1.481% to 25.85% | 100 | 88.65% to 100.0% | |
| >4229 | 4.167 | 0.2137% to 20.24% | 100 | 88.65% to 100.0% | |

TABLE 8

Immature neutrophils to VD2 ratio all time points. No pneumonia vs pneumonia

| Ratio | Sensitivity % | 95% CI | Specificity % | 95% CI | Likelihood ratio |
|---|---|---|---|---|---|
| >3.869 | 97.14 | 85.47% to 99.85% | 0 | 0.000% to 16.82% | 0.9714 |
| >4.155 | 97.14 | 85.47% to 99.85% | 5.263 | 0.2700% to 24.64% | 1.025 |
| >4.445 | 94.29 | 81.39% to 98.98% | 5.263 | 0.2700% to 24.64% | 0.9952 |
| >5.164 | 91.43 | 77.62% to 97.04% | 5.263 | 0.2700% to 24.64% | 0.9651 |
| >6.120 | 91.43 | 77.62% to 97.04% | 10.53 | 1.870% to 31.39% | 1.022 |
| >6.609 | 88.57 | 74.05% to 95.46% | 10.53 | 1.870% to 31.39% | 0.9899 |
| >6.883 | 88.57 | 74.05% to 95.46% | 15.79 | 5.520% to 37.57% | 1.052 |
| >7.879 | 88.57 | 74.05% to 95.46% | 21.05 | 8.508% to 43.33% | 1.122 |
| >10.33 | 88.57 | 74.05% to 95.46% | 26.32 | 11.81% to 48.79% | 1.202 |
| >11.94 | 88.57 | 74.05% to 95.46% | 31.58 | 15.36% to 53.99% | 1.295 |
| >12.09 | 88.57 | 74.05% to 95.46% | 36.84 | 19.15% to 58.96% | 1.402 |
| >12.48 | 88.57 | 74.05% to 95.46% | 42.11 | 23.14% to 63.72% | 1.53 |
| >12.85 | 88.57 | 74.05% to 95.46% | 47.37 | 27.33% to 68.29% | 1.683 |
| >13.00 | 85.71 | 70.62% to 93.74% | 47.37 | 27.33% to 68.29% | 1.629 |
| >13.35 | 85.71 | 70.62% to 93.74% | 52.63 | 31.71% to 72.67% | 1.81 |
| >15.04 | 85.71 | 70.62% to 93.74% | 57.89 | 36.28% to 76.86% | 2.036 |
| >18.39 | 85.71 | 70.62% to 93.74% | 63.16 | 41.04% to 80.85% | 2.327 |

TABLE 8-continued

Immature neutrophils to VD2 ratio all time points. No pneumonia vs pneumonia

| Ratio | Sensitivity % | 95% CI | Specificity % | 95% CI | Likelihood ratio |
|---|---|---|---|---|---|
| >21.40 | 85.71 | 70.62% to 93.74% | 68.42 | 46.01% to 84.64% | 2.714 |
| >23.33 | 82.86 | 67.32% to 91.90% | 68.42 | 46.01% to 84.64% | 2.624 |
| >25.22 | 82.86 | 67.32% to 91.90% | 73.68 | 51.21% to 88.19% | 3.149 |
| >26.80 | 80 | 64.11% to 89.96% | 73.68 | 51.21% to 88.19% | 3.04 |
| >27.60 | 77.14 | 60.98% to 87.93% | 73.68 | 51.21% to 88.19% | 2.931 |
| >29.87 | 77.14 | 60.98% to 87.93% | 78.95 | 56.67% to 91.49% | 3.664 |
| >35.46 | 77.14 | 60.98% to 87.93% | 84.21 | 62.43% to 94.48% | 4.886 |
| >41.24 | 74.29 | 57.93% to 85.84% | 84.21 | 62.43% to 94.48% | 4.705 |
| >43.83 | 74.29 | 57.93% to 85.84% | 89.47 | 68.61% to 98.13% | 7.057 |
| >48.30 | 74.29 | 57.93% to 85.84% | 94.74 | 75.36% to 99.73% | 14.11 |
| >56.33 | 71.43 | 54.95% to 83.67% | 94.74 | 75.36% to 99.73% | 13.57 |
| >61.17 | 68.57 | 52.02% to 81.45% | 94.74 | 75.36% to 99.73% | 13.03 |
| >62.88 | 68.57 | 52.02% to 81.45% | 100 | 83.18% to 100.0% | |
| >77.21 | 65.71 | 49.15% to 79.17% | 100 | 83.18% to 100.0% | |
| >102.6 | 62.86 | 46.34% to 76.83% | 100 | 83.18% to 100.0% | |
| >117.4 | 60 | 43.57% to 74.45% | 100 | 83.18% to 100.0% | |
| >122.9 | 57.14 | 40.86% to 72.02% | 100 | 83.18% to 100.0% | |
| >141.3 | 54.29 | 38.19% to 69.53% | 100 | 83.18% to 100.0% | |
| >179.3 | 51.43 | 35.57% to 67.01% | 100 | 83.18% to 100.0% | |
| >232.3 | 48.57 | 32.99% to 64.43% | 100 | 83.18% to 100.0% | |
| >273.1 | 45.71 | 30.47% to 61.81% | 100 | 83.18% to 100.0% | |
| >292.8 | 42.86 | 27.98% to 59.14% | 100 | 83.18% to 100.0% | |
| >304.0 | 40 | 25.55% to 56.43% | 100 | 83.18% to 100.0% | |
| >329.6 | 37.14 | 23.17% to 53.66% | 100 | 83.18% to 100.0% | |
| >359.6 | 34.29 | 20.83% to 50.85% | 100 | 83.18% to 100.0% | |
| >384.4 | 31.43 | 18.55% to 47.98% | 100 | 83.18% to 100.0% | |
| >443.6 | 28.57 | 16.33% to 45.05% | 100 | 83.18% to 100.0% | |
| >492.5 | 25.71 | 14.16% to 42.07% | 100 | 83.18% to 100.0% | |
| >539.0 | 22.86 | 12.07% to 39.02% | 100 | 83.18% to 100.0% | |
| >597.1 | 20 | 10.04% to 35.89% | 100 | 83.18% to 100.0% | |
| >723.3 | 17.14 | 8.103% to 32.68% | 100 | 83.18% to 100.0% | |
| >829.2 | 14.29 | 6.260% to 29.38% | 100 | 83.18% to 100.0% | |
| >972.0 | 11.43 | 4.535% to 25.95% | 100 | 83.18% to 100.0% | |
| >1778 | 8.571 | 2.958% to 22.38% | 100 | 83.18% to 100.0% | |
| >3004 | 5.714 | 1.015% to 18.61% | 100 | 83.18% to 100.0% | |
| >4229 | 2.857 | 0.1466% to 14.53% | 100 | 83.18% to 100.0% | | i. ROC Data for Immature Neutrophils to CD8 Ratio:

TABLE 9

Immature neutrophils to CD8 ratio early time point. No hypoxia vs hypoxia

| Ratio | Sensitivity % | 95% CI | Specificity % | 95% CI | Likelihood ratio |
|---|---|---|---|---|---|
| >0.5804 | 100 | 64.57% to 100.0% | 5.882 | 0.3017% to 26.98% | 1.063 |
| >0.8100 | 100 | 64.57% to 100.0% | 11.76 | 2.090% to 34.34% | 1.133 |
| >0.9954 | 85.71 | 48.69% to 99.27% | 11.76 | 2.090% to 34.34% | 0.9714 |
| >1.089 | 85.71 | 48.69% to 99.27% | 17.65 | 6.191% to 41.03% | 1.041 |
| >1.212 | 85.71 | 48.69% to 99.27% | 23.53 | 9.555% to 47.26% | 1.121 |
| >1.327 | 85.71 | 48.69% to 99.27% | 29.41 | 13.28% to 53.13% | 1.214 |
| >1.372 | 85.71 | 48.69% to 99.27% | 35.29 | 17.31% to 58.70% | 1.325 |
| >1.410 | 85.71 | 48.69% to 99.27% | 41.18 | 21.61% to 63.99% | 1.457 |
| >1.530 | 85.71 | 48.69% to 99.27% | 47.06 | 26.17% to 69.04% | 1.619 |
| >1.961 | 85.71 | 48.69% to 99.27% | 52.94 | 30.96% to 73.83% | 1.821 |
| >2.389 | 85.71 | 48.69% to 99.27% | 58.82 | 36.01% to 78.39% | 2.082 |
| >2.532 | 85.71 | 48.69% to 99.27% | 64.71 | 41.30% to 82.69% | 2.429 |
| >3.112 | 85.71 | 48.69% to 99.27% | 70.59 | 46.87% to 86.72% | 2.914 |
| >3.767 | 85.71 | 48.69% to 99.27% | 76.47 | 52.74% to 90.44% | 3.643 |
| >4.054 | 71.43 | 35.89% to 94.92% | 76.47 | 52.74% to 90.44% | 3.036 |
| >5.339 | 71.43 | 35.89% to 94.92% | 82.35 | 58.97% to 93.81% | 4.048 |
| >7.045 | 71.43 | 35.89% to 94.92% | 88.24 | 65.66% to 97.91% | 6.071 |
| >8.288 | 71.43 | 35.89% to 94.92% | 94.12 | 73.02% to 99.70% | 12.14 |
| >10.97 | 71.43 | 35.89% to 94.92% | 100 | 81.57% to 100.0% | |
| >14.75 | 57.14 | 25.05% to 84.18% | 100 | 81.57% to 100.0% | |
| >27.86 | 42.86 | 15.82% to 74.95% | 100 | 81.57% to 100.0% | |
| >62.64 | 28.57 | 5.077% to 64.11% | 100 | 81.57% to 100.0% | |
| >157.9 | 14.29 | 0.7328% to 51.31% | 100 | 81.57% to 100.0% | |

TABLE 10

Immature neutrophils to CD8 ratio early time point. No pneumonia vs pneumonia

| Ratio | Sensitivity % | 95% CI | Specificity % | 95% CI | Likelihood ratio |
|---|---|---|---|---|---|
| >0.5804 | 100 | 72.25% to 100.0% | 7.143 | 0.3664% to 31.47% | 1.077 |
| >0.8100 | 100 | 72.25% to 100.0% | 14.29 | 2.538% to 39.94% | 1.167 |
| >0.9954 | 90 | 59.58% to 99.49% | 14.29 | 2.538% to 39.94% | 1.05 |
| >1.089 | 90 | 59.58% to 99.49% | 21.43 | 7.571% to 47.59% | 1.145 |
| >1.212 | 90 | 59.58% to 99.49% | 28.57 | 11.72% to 54.65% | 1.26 |
| >1.327 | 80 | 49.02% to 96.45% | 28.57 | 11.72% to 54.65% | 1.12 |
| >1.372 | 80 | 49.02% to 96.45% | 35.71 | 16.34% to 61.24% | 1.244 |

TABLE 10-continued

Immature neutrophils to CD8 ratio early time point. No pneumonia vs pneumonia

| Ratio | Sensitivity % | 95% CI | Specificity % | 95% CI | Likelihood ratio |
|---|---|---|---|---|---|
| >1.410 | 80 | 49.02% to 96.45% | 42.86 | 21.38% to 67.41% | 1.4 |
| >1.530 | 80 | 49.02% to 96.45% | 50 | 26.80% to 73.20% | 1.6 |
| >1.961 | 80 | 49.02% to 96.45% | 57.14 | 32.59% to 78.62% | 1.867 |
| >2.389 | 80 | 49.02% to 96.45% | 64.29 | 38.76% to 83.66% | 2.24 |
| >2.532 | 80 | 49.02% to 96.45% | 71.43 | 45.35% to 88.28% | 2.8 |
| >3.112 | 80 | 49.02% to 96.45% | 78.57 | 52.41% to 92.43% | 3.733 |
| >3.767 | 70 | 39.68% to 89.22% | 78.57 | 52.41% to 92.43% | 3.267 |
| >4.054 | 60 | 31.27% to 83.18% | 78.57 | 52.41% to 92.43% | 2.8 |
| >5.339 | 60 | 31.27% to 83.18% | 85.71 | 60.06% to 97.46% | 4.2 |
| >7.045 | 60 | 31.27% to 83.18% | 92.86 | 68.53% to 99.63% | 8.4 |
| >8.288 | 50 | 23.66% to 76.34% | 92.86 | 68.53% to 99.63% | 7 |
| >10.97 | 50 | 23.66% to 76.34% | 100 | 78.47% to 100.0% |  |
| >14.75 | 40 | 16.82% to 68.73% | 100 | 78.47% to 100.0% |  |
| >27.86 | 30 | 10.78% to 60.32% | 100 | 78.47% to 100.0% |  |
| >62.64 | 20 | 3.554% to 50.98% | 100 | 78.47% to 100.0% |  |
| >157.9 | 10 | 0.5129% to 40.42% | 100 | 78.47% to 100.0% |  |

TABLE 11

Immature neutrophils to CD8 ratio all time points. No hypoxia vs hypoxia

| Ratio | Sensitivity % | 95% CI | Specificity % | 95% CI | Likelihood ratio |
|---|---|---|---|---|---|
| >0.3641 | 100 | 86.20% to 100.0% | 3.333 | 0.1710% to 16.67% | 1.034 |
| >0.4641 | 100 | 86.20% to 100.0% | 6.667 | 1.185% to 21.32% | 1.071 |
| >0.5804 | 100 | 86.20% to 100.0% | 10 | 3.460% to 25.62% | 1.111 |
| >0.7651 | 100 | 86.20% to 100.0% | 13.33 | 5.310% to 29.68% | 1.154 |
| >0.8693 | 100 | 86.20% to 100.0% | 16.67 | 7.337% to 33.56% | 1.2 |
| >0.9141 | 100 | 86.20% to 100.0% | 20 | 9.505% to 37.31% | 1.25 |
| >0.9954 | 95.83 | 79.76% to 99.79% | 20 | 9.505% to 37.31% | 1.198 |
| >1.089 | 95.83 | 79.76% to 99.79% | 23.33 | 11.79% to 40.93% | 1.25 |
| >1.133 | 95.83 | 79.76% to 99.79% | 26.67 | 14.18% to 44.45% | 1.307 |
| >1.231 | 95.83 | 79.76% to 99.79% | 30 | 16.66% to 47.88% | 1.369 |
| >1.327 | 95.83 | 79.76% to 99.79% | 33.33 | 19.23% to 51.22% | 1.438 |
| >1.372 | 95.83 | 79.76% to 99.79% | 36.67 | 21.87% to 54.49% | 1.513 |
| >1.410 | 95.83 | 79.76% to 99.79% | 40 | 24.59% to 57.68% | 1.597 |
| >1.446 | 95.83 | 79.76% to 99.79% | 43.33 | 27.38% to 60.80% | 1.691 |
| >1.517 | 95.83 | 79.76% to 99.79% | 46.67 | 30.23% to 63.86% | 1.797 |
| >1.564 | 95.83 | 79.76% to 99.79% | 50 | 33.15% to 66.85% | 1.917 |
| >1.604 | 95.83 | 79.76% to 99.79% | 53.33 | 36.14% to 69.77% | 2.054 |
| >1.640 | 95.83 | 79.76% to 99.79% | 56.67 | 39.20% to 72.62% | 2.212 |
| >1.707 | 95.83 | 79.76% to 99.79% | 60 | 42.32% to 75.41% | 2.396 |
| >1.926 | 91.67 | 74.15% to 98.52% | 60 | 42.32% to 75.41% | 2.292 |
| >2.181 | 91.67 | 74.15% to 98.52% | 63.33 | 45.51% to 78.13% | 2.5 |
| >2.389 | 91.67 | 74.15% to 98.52% | 66.67 | 48.78% to 80.77% | 2.75 |
| >2.532 | 91.67 | 74.15% to 98.52% | 70 | 52.12% to 83.34% | 3.056 |
| >2.627 | 91.67 | 74.15% to 98.52% | 73.33 | 55.55% to 85.82% | 3.438 |
| >3.173 | 91.67 | 74.15% to 98.52% | 76.67 | 59.07% to 88.21% | 3.929 |
| >3.767 | 91.67 | 74.15% to 98.52% | 80 | 62.69% to 90.49% | 4.583 |
| >4.054 | 87.5 | 69.00% to 95.66% | 80 | 62.69% to 90.49% | 4.375 |
| >4.277 | 87.5 | 69.00% to 95.66% | 83.33 | 66.44% to 92.66% | 5.25 |
| >4.424 | 83.33 | 64.15% to 93.32% | 83.33 | 66.44% to 92.66% | 5 |
| >4.676 | 79.17 | 59.53% to 90.76% | 83.33 | 66.44% to 92.66% | 4.75 |
| >5.164 | 75 | 55.10% to 88.00% | 83.33 | 66.44% to 92.66% | 4.5 |
| >5.974 | 70.83 | 50.83% to 85.09% | 83.33 | 66.44% to 92.66% | 4.25 |
| >6.783 | 70.83 | 50.83% to 85.09% | 86.67 | 70.32% to 94.69% | 5.313 |
| >7.381 | 66.67 | 46.71% to 82.03% | 86.67 | 70.32% to 94.69% | 5 |
| >7.926 | 66.67 | 46.71% to 82.03% | 90 | 74.38% to 96.54% | 6.667 |
| >8.571 | 62.5 | 42.71% to 78.84% | 90 | 74.38% to 96.54% | 6.25 |
| >10.14 | 62.5 | 42.71% to 78.84% | 93.33 | 78.68% to 98.82% | 9.375 |
| >11.99 | 58.33 | 38.83% to 75.53% | 93.33 | 78.68% to 98.82% | 8.75 |
| >12.82 | 54.17 | 35.07% to 72.11% | 93.33 | 78.68% to 98.82% | 8.125 |
| >13.06 | 50 | 31.43% to 68.57% | 93.33 | 78.68% to 98.82% | 7.5 |
| >14.36 | 50 | 31.43% to 68.57% | 96.67 | 83.33% to 99.83% | 15 |
| >16.05 | 45.83 | 27.89% to 64.93% | 96.67 | 83.33% to 99.83% | 13.75 |
| >17.01 | 41.67 | 24.47% to 61.17% | 96.67 | 83.33% to 99.83% | 12.5 |
| >19.46 | 41.67 | 24.47% to 61.17% | 100 | 88.65% to 100.0% |  |
| >22.37 | 37.5 | 21.16% to 57.29% | 100 | 88.65% to 100.0% |  |
| >26.62 | 33.33 | 17.97% to 53.29% | 100 | 88.65% to 100.0% |  |
| >32.73 | 29.17 | 14.91% to 49.17% | 100 | 88.65% to 100.0% |  |
| >36.67 | 25 | 12.00% to 44.90% | 100 | 88.65% to 100.0% |  |
| >38.51 | 20.83 | 9.245% to 40.47% | 100 | 88.65% to 100.0% |  |
| >62.64 | 16.67 | 6.679% to 35.85% | 100 | 88.65% to 100.0% |  |
| >109.1 | 12.5 | 4.344% to 31.00% | 100 | 88.65% to 100.0% |  |
| >138.3 | 8.333 | 1.481% to 25.85% | 100 | 88.65% to 100.0% |  |

TABLE 11-continued

Immature neutrophils to CD8 ratio all time points. No hypoxia vs hypoxia

| Ratio | Sensitivity % | 95% CI | Specificity % | 95% CI | Likelihood ratio |
|---|---|---|---|---|---|
| >187.2 | 4.167 | 0.2137% to 20.24% | 100 | 88.65% to 100.0% | |

TABLE 12

Immature neutrophils to CD8 ratio all time points. No pneumonia vs pneumonia

| Ratio | Sensitivity % | 95% CI | Specificity % | 95% CI | Likelihood ratio |
|---|---|---|---|---|---|
| >0.3641 | 97.14 | 85.47% to 99.85% | 0 | 0.000% to 16.82% | 0.9714 |
| >0.4641 | 97.14 | 85.47% to 99.85% | 5.263 | 0.2700% to 24.64% | 1.025 |
| >0.5804 | 97.14 | 85.47% to 99.85% | 10.53 | 1.870% to 31.39% | 1.086 |
| >0.7651 | 97.14 | 85.47% to 99.85% | 15.79 | 5.520% to 37.57% | 1.154 |
| >0.8693 | 94.29 | 81.39% to 98.98% | 15.79 | 5.520% to 37.57% | 1.12 |
| >0.9141 | 91.43 | 77.62% to 97.04% | 15.79 | 5.520% to 37.57% | 1.086 |
| >0.9954 | 88.57 | 74.05% to 95.46% | 15.79 | 5.520% to 37.57% | 1.052 |
| >1.089 | 88.57 | 74.05% to 95.46% | 21.05 | 8.508% to 43.33% | 1.122 |
| >1.133 | 88.57 | 74.05% to 95.46% | 26.32 | 11.81% to 48.79% | 1.202 |
| >1.231 | 88.57 | 74.05% to 95.46% | 31.58 | 15.36% to 53.99% | 1.295 |
| >1.327 | 85.71 | 70.62% to 93.74% | 31.58 | 15.36% to 53.99% | 1.253 |
| >1.372 | 85.71 | 70.62% to 93.74% | 36.84 | 19.15% to 58.96% | 1.357 |
| >1.410 | 85.71 | 70.62% to 93.74% | 42.11 | 23.14% to 63.72% | 1.481 |
| >1.446 | 85.71 | 70.62% to 93.74% | 47.37 | 27.33% to 68.29% | 1.629 |
| >1.517 | 82.86 | 67.32% to 91.90% | 47.37 | 27.33% to 68.29% | 1.574 |
| >1.564 | 82.86 | 67.32% to 91.90% | 52.63 | 31.71% to 72.67% | 1.749 |
| >1.604 | 82.86 | 67.32% to 91.90% | 57.89 | 36.28% to 76.86% | 1.968 |
| >1.640 | 80 | 64.11% to 89.96% | 57.89 | 36.28% to 76.86% | 1.9 |
| >1.707 | 80 | 64.11% to 89.96% | 63.16 | 41.04% to 80.85% | 2.171 |
| >1.926 | 77.14 | 60.98% to 87.93% | 63.16 | 41.04% to 80.85% | 2.094 |
| >2.181 | 74.29 | 57.93% to 85.84% | 63.16 | 41.04% to 80.85% | 2.016 |
| >2.389 | 74.29 | 57.93% to 85.84% | 68.42 | 46.01% to 84.64% | 2.352 |
| >2.532 | 74.29 | 57.93% to 85.84% | 73.68 | 51.21% to 88.19% | 2.823 |
| >2.627 | 74.29 | 57.93% to 85.84% | 78.95 | 56.67% to 91.49% | 3.529 |
| >3.173 | 74.29 | 57.93% to 85.84% | 84.21 | 62.43% to 94.48% | 4.705 |
| >3.767 | 71.43 | 54.95% to 83.67% | 84.21 | 62.43% to 94.48% | 4.524 |
| >4.054 | 68.57 | 52.02% to 81.45% | 84.21 | 62.43% to 94.48% | 4.343 |
| >4.277 | 68.57 | 52.02% to 81.45% | 89.47 | 68.61% to 98.13% | 6.514 |
| >4.424 | 65.71 | 49.15% to 79.17% | 89.47 | 68.61% to 98.13% | 6.243 |
| >4.676 | 62.86 | 46.34% to 76.83% | 89.47 | 68.61% to 98.13% | 5.971 |

TABLE 12-continued

Immature neutrophils to CD8 ratio all time points. No pneumonia vs pneumonia

| Ratio | Sensitivity % | 95% CI | Specificity % | 95% CI | Likelihood ratio |
|---|---|---|---|---|---|
| >5.164 | 60 | 43.57% to 74.45% | 89.47 | 68.61% to 98.13% | 5.7 |
| >5.974 | 57.14 | 40.86% to 72.02% | 89.47 | 68.61% to 98.13% | 5.429 |
| >6.783 | 57.14 | 40.86% to 72.02% | 94.74 | 75.36% to 99.73% | 10.86 |
| >7.381 | 54.29 | 38.19% to 69.53% | 94.74 | 75.36% to 99.73% | 10.31 |
| >7.926 | 51.43 | 35.57% to 67.01% | 94.74 | 75.36% to 99.73% | 9.771 |
| >8.571 | 48.57 | 32.99% to 64.43% | 94.74 | 75.36% to 99.73% | 9.229 |
| >10.14 | 48.57 | 32.99% to 64.43% | 100 | 83.18% to 100.0% | |
| >11.99 | 45.71 | 30.47% to 61.81% | 100 | 83.18% to 100.0% | |
| >12.82 | 42.86 | 27.98% to 59.14% | 100 | 83.18% to 100.0% | |
| >13.06 | 40 | 25.55% to 56.43% | 100 | 83.18% to 100.0% | |
| >14.36 | 37.14 | 23.17% to 53.66% | 100 | 83.18% to 100.0% | |
| >16.05 | 34.29 | 20.83% to 50.85% | 100 | 83.18% to 100.0% | |
| >17.01 | 31.43 | 18.55% to 47.98% | 100 | 83.18% to 100.0% | |
| >19.46 | 28.57 | 16.33% to 45.05% | 100 | 83.18% to 100.0% | |
| >22.37 | 25.71 | 14.16% to 42.07% | 100 | 83.18% to 100.0% | |
| >26.62 | 22.86 | 12.07% to 39.02% | 100 | 83.18% to 100.0% | |
| >32.73 | 20 | 10.04% to 35.89% | 100 | 83.18% to 100.0% | |
| >36.67 | 17.14 | 8.103% to 32.68% | 100 | 83.18% to 100.0% | |
| >38.51 | 14.29 | 6.260% to 29.38% | 100 | 83.18% to 100.0% | |
| >62.64 | 11.43 | 4.535% to 25.95% | 100 | 83.18% to 100.0% | |
| >109.1 | 8.571 | 2.958% to 22.38% | 100 | 83.18% to 100.0% | |
| >138.3 | 5.714 | 1.015% to 18.61% | 100 | 83.18% to 100.0% | |
| >187.2 | 2.857 | 0.1466% to 14.53% | 100 | 83.18% to 100.0% | |

TABLE 13

ROC curve analysis for neutrophils to T-cell ratios in patients with pneumonia or hypoxia compared to those without as presented in FIG. 5A-B.

| | Pneumonia | | | Hypoxia | | |
|---|---|---|---|---|---|---|
| Variable | AUC (95% CI) | Std. Error | p-value | AUC (95% CI) | Std. Error | p-value |
| Total neutrophils/ CD8 T-cells (n = 54) | 0.7158 0.5754 to 0.8562 | 0.07163 | 0.0093 | 0.7958 0.6781 to 0.9136 | 0.06008 | 0.0002 |
| Early total neutrophils/ CD8 T-cells (n = 24) | 0.7143 0.4909 to 0.9377 | 0.114 | 0.079 | 0.8319 0.6526 to 1.0 | 0.09149 | 0.0121 |
| Immature neutrophils/ VD2 T-cells (n = 54) | 0.8451 0.7379 to 0.9523 | 0.05471 | <0.0001 | 0.9111 0.8306 to 0.9916 | 0.04108 | <0.0001 |

TABLE 13-continued

ROC curve analysis for neutrophils to T-cell ratios in patients
with pneumonia or hypoxia compared to
those without as presented in FIG. 5A-B.

| | Pneumonia | | | Hypoxia | | |
|---|---|---|---|---|---|---|
| Variable | AUC (95% CI) | Std. Error | p-value | AUC (95% CI) | Std. Error | p-value |
| Early immature neutrophils/ VD2 T-cells (n = 24) | 0.9071 0.7754 to 1.0 | 0.06723 | 0.0008 | 0.8908 0.7160 to 1.0 | 0.08915 | 0.0031 |

ROC analysis was performed on all 54 COVID-19 patients or a subset of 24 sampled between 2 to 7 days pio (24 patients, median 3 days pio). ROC curve was built by plotting true positive rate (sensitivity) against false positive rate (100%- sensitivity) and AUC was calculated from the plot using the Wilson/Brown method. ROC, receiver operating characteristic ; AUC, area under curve ; Ci, confidence interval ; Std. Error, standard error.

In this study, immunophenotyping of peripheral blood from COVID-19 patients revealed a significant shift in the ratio between mature and immature neutrophils associating with severity. The increased numbers of immature neutrophils and the disappearance of mature neutrophils likely reflect gradual and sustained mobilisation of these cells into the lungs in response to an ongoing inflammation, leading to premature release of immature neutrophils from the bone marrow[22]. Supporting this hypothesis, a recent study, investigating several myeloid populations between circulating PBMCs and the lung lavage of COVID-19 patients showed that granulocytes represent up to 80% of total CD45+ lung infiltrates[29]. In addition, autopsies of COVID-19 fatalities showed typical lesions associated with toxic neutrophil effects[30,31]. In line with this observation, marked morphological abnormalities of the circulating neutrophils were reported in COVID-19 patients[28]. These cells present typical hallmarks of immature neutrophils and their precursors such as band shaped nuclei and a lower expression of CD10 and CD16[32]. Consistent with our data, a recent non peer reviewed study on a small number of patients reported that the presence of "low density inflammatory neutrophils" was strongly associated with disease severity and IL-6 levels 33. Functionally these low density neutrophils showed spontaneous extracellular trap formation, enhanced cytokine production and associated with D-dimer and systemic IL-6 and TNF-α levels 33. We hypothesise that the $CD11b^{int}CD44^{low}CD16^{int}$ low density neutrophil population identified in that study is likely constituted primarily of CD10− immature neutrophils. More recently, two studies used flow cytometry, single cell sequencing and mass cytometry to confirm the immature and dysfunctional phenotype in the myeloid populations, including these neutrophils[34,35]. Interestingly, the diagnostic value of a neutrophil "left shift" (banded versus segmented neutrophils) had previously been explored in order to predict infectious diseases in addition to inflammatory diseases[36] and is therefore not limited to COVID-19 severity. Similarly, the presence of immature low density neutrophils have been reported in the literature for various infectious and inflammatory diseases 37-39 as well as induced by LPS in healthy subjects[40], highlighting the necessity of future studies to compare the role and function of these COVID-19 immature neutrophils with the circulating immature neutrophils present in other diseases.

During SARS-CoV-2 infection, immature neutrophil numbers strongly correlated with IL-6 and IP-10. IL-6 and IP-10 are consistently upregulated during a cytokine storm and are associated with severe ARDS[12,13,41,42] While some studies report inflammatory monocytes as the source of IL-6[12,43,44], our results suggest that immature neutrophils could also be a non-negligible source of IL-6 during COVID-19-induced cytokine storm. Indeed, neutrophils have been found to produce biologically relevant amounts of IL-6 after engagement of TLR8, a toll like receptor recognising single strand RNAs of viral or bacterial origin[45,46]. Since IL-17 operates upstream of IL-1 and IL-6, and is a major orchestrator of sustained neutrophils mobilisation 47, it is plausible that IL-17 could significantly affect the neutrophils compartment in COVID-19 patients. Consistent with this hypothesis, CD4 T-cells in COVID-19 patients are skewed towards a Th17 phenotype[16], and we also observed increased CD4+CD161+ T-cells in recovered patients. These CD4+CD161+ T-cells are known to be either IL-17 producer cells or their precursors[48]. Thus, our results could reflect the re-circulation of these cells from the lung or secondary lymphoid organs after infection and support the possibility of IL-17 in mediating neutrophil damage to the lungs. Together, this would support proposed anti-IL-17 or JAK2 inhibitor therapies for severe COVID-19 disease[49-51].

In addition to the changes in the heterogeneity of neutrophils, a strong decrease in T-cells was observed, especially in subsets that possess cytolytic activity such as CD8, VD1 and VD2 T-cells. These results are consistent with other studies showing a decrease of CD8+ during COVID-19 disease[15,16] As for VD2 T cells, which are not MHC-restricted T-cells[52,53] we showed a general decrease in the periphery with disease severity. This is in line with other inflammatory disease such as psoriasis 54 and Crohn's disease 55. However, in the lungs, during chronic obstructive pulmonary disease, γδ T-cell counts have been reported to be significantly lower in induced sputum (IS) and bronchoalveolar lavage (BAL) but not in peripheral blood, suggesting unclear inflammatory mechanisms that could influence γδ T-cells counts in the periphery 56 Interestingly, γδ T-cells, in particular VD2, are known to participate in influenza immune response 57, and actively recruit and activate neutrophils to the site of infection or inflammation[58,59]. Activated, neutrophils have also been found to inhibit γδ T-cells functional capacity, promoting the resolution of inflammation[60,61] Therefore, it will be essential to investigate the neutrophil to γδ T-cells relationship present in lungs of SARS-CoV-2 infected patients.

During aging, VD2 T-cell counts in the periphery have been shown to decrease with age for both males and females[62-65]. Interestingly, VD2 counts between males and females can be quite variable depending on the population sampled. Higher VD2 counts in males were observed in a Japanese population, while a similar study in Germany and Italy observed higher VD2 counts in females[62,65] Additionally, elderly individuals generally have systemic chronic low-grade inflammation, which was previously termed "inflamm-aging"[66], with higher basal levels of molecules such as CRP, TNF-α and IL-6[67-69]. These similarities in modulation of VD2 T-cell counts and cytokines between COVID-19 severity and aging could explain why elderly individuals are more susceptible to severe disease, since they have a higher basal level of inflammation and lower level of VD2 T-cells as compared to the young. In any case, the lower VD2 counts in elderly populations will influence the immature neutrophil to VD2 ratio by overestimating their risk to severe COVID-19 as compared to a younger population. However, since age is a very well established risk factor for severe COVID-19 disease[70-72], we postulate that the immature neutrophil to VD2 ratio takes into account the immunological age (measured by VD2 T-cell counts of the patient) which contributes to the improved sensitivity and specificity observed here with area under receiver operating characteristic analysis (FIG. 5A-B).

Our results indicate that an early post illness onset iNVD2R, accessible through a simple 5 colours flow cytometry panel (CD3; VD2; CD66b/CD15; CD10; CD45), would be an excellent prognostic screening tool for predicting probable patient progression to pneumonia or hypoxia. This prognostic possibility needs to be validated in a prospective cohort. Moreover, CD8 could also be included in the flow cytometry panel as a fallback option since VD2 counts could be decreased by medication, such as Azathioprine, as well as underlying conditions, such as inflammatory bowel disease, aging or psoriasis, which could be risk factors for COVID-19[55]. Analysis of the proposed parameter would allow for a more accurate and earlier prognosis due to the interconnection between neutrophils and Vδ2 T cells, which can then be utilised for early therapeutic interventions, improve patient triage and better healthcare resource management.

REFERENCES

1 Cohen, J. & Normile, D. New SARS-like virus in China triggers alarm. *Science* 367, 234-235, doi:10.1126/science.367.6475.234 (2020).

2 Guan, W. J., Ni, Z. Y., Hu, Y., Liang, W. H., Ou, C. Q., He, J. X., Liu, L., Shan, H., Lei, C. L., Hui, D. S. C., Du, B., Li, L. J., Zeng, G., Yuen, K. Y., Chen, R. C., Tang, C. L., Wang, T., Chen, P. Y., Xiang, J., Li, S. Y., Wang, J. L., Liang, Z. J., Peng, Y. X., Wei, L., Liu, Y., Hu, Y. H., Peng, P., Wang, J. M., Liu, J. Y., Chen, Z., Li, G., Zheng, Z. J., Qiu, S. Q., Luo, J., Ye, C. J., Zhu, S. Y., Zhong, N. S. & China Medical Treatment Expert Group for, C. Clinical Characteristics of Coronavirus Disease 2019 in China. *N Engl J Med*, doi:10.1056/NEJMoa2002032 (2020).

3 Wu, Z. & McGoogan, J. M. Characteristics of and Important Lessons From the Coronavirus Disease 2019 (COVID-19) Outbreak in China: Summary of a Report of 72314 Cases From the Chinese Center for Disease Control and Prevention. *JAMA*, doi:10.1001/jama.2020.2648 (2020).

4 Wang, D., Hu, B., Hu, C., Zhu, F., Liu, X., Zhang, J., Wang, B., Xiang, H., Cheng, Z., Xiong, Y., Zhao, Y., Li, Y., Wang, X. & Peng, Z. Clinical Characteristics of 138 Hospitalized Patients With 2019 Novel Coronavirus-Infected Pneumonia in Wuhan, China. *JAMA*, doi:10.1001/jama.2020.1585 (2020).

5 Chen, N., Zhou, M., Dong, X., Qu, J., Gong, F., Han, Y., Qiu, Y., Wang, J., Liu, Y., Wei, Y., Xia, J., Yu, T., Zhang, X. & Zhang, L. Epidemiological and clinical characteristics of 99 cases of 2019 novel coronavirus pneumonia in Wuhan, China: a descriptive study. *Lancet* 395, 507-513, doi:10.1016/S0140-6736(20)30211-7 (2020).

6 Connors, J. M. & Levy, J. H. COVID-19 and its implications for thrombosis and anticoagulation. *Blood* 135, 2033-2040, doi:10.1182/blood.2020006000 (2020).

7 Magro, C., Mulvey, J. J., Berlin, D., Nuovo, G., Salvatore, S., Harp, J., Baxter-Stoltzfus, A. & Laurence, J. Complement associated microvascular injury and thrombosis in the pathogenesis of severe COVID-19 infection: A report of five cases. *Transl Res* 220, 1-13, doi:10.1016/j.trsl.2020.04.007 (2020).

8 Jose, R. J. & Manuel, A. COVID-19 cytokine storm: the interplay between inflammation and coagulation. *Lancet Respir Med* 8, e46-e47, doi:10.1016/S2213-2600(20)30216-2 (2020).

9 Chen, G., Wu, D., Guo, W., Cao, Y., Huang, D., Wang, H., Wang, T., Zhang, X., Chen, H., Yu, H., Zhang, M., Wu, S., Song, J., Chen, T., Han, M., Li, S., Luo, X., Zhao, J. & Ning, Q. Clinical and immunological features of severe and moderate coronavirus disease 2019. *J Clin Invest* 130, 2620-2629, doi:10.1172/JC1137244 (2020).

10 Zheng, H. Y., Zhang, M., Yang, C. X., Zhang, N., Wang, X. C., Yang, X. P., Dong, X. Q. & Zheng, Y. T. Elevated exhaustion levels and reduced functional diversity of T cells in peripheral blood may predict severe progression in COVID-19 patients. *Cell Mol Immunol*, doi:10.1038/s41423-020-0401-3 (2020).

11 Qin, C., Zhou, L., Hu, Z., Zhang, S., Yang, S., Tao, Y., Xie, C., Ma, K., Shang, K., Wang, W. & Tian, D. S. Dysregulation of immune response in patients with COVID-19 in Wuhan, China. *Clin Infect Dis*, doi:10.1093/cid/ciaa248 (2020).

12 Zhou, Y., Fu, B., Zheng, X., Wang, D., Zhao, C., qi, Y., Sun, R., Tian, Z., Xu, X. & Wei, H. Pathogenic T cells and inflammatory monocytes incite inflammatory storm in severe COVID-19 patients. *National Science Review*, doi:10.1093/nsr/nwaa041 (2020).

13 Huang, C., Wang, Y., Li, X., Ren, L., Zhao, J., Hu, Y., Zhang, L., Fan, G., Xu, J., Gu, X., Cheng, Z., Yu, T., Xia, J., Wei, Y., Wu, W., Xie, X., Yin, W., Li, H., Liu, M., Xiao, Y., Gao, H., Guo, L., Xie, J., Wang, G., Jiang, R., Gao, Z., Jin, Q., Wang, J. & Cao, B. Clinical features of patients infected with 2019 novel coronavirus in Wuhan, China. *Lancet* 395, 497-506, doi:10.1016/S0140-6736(20)30183-5 (2020).

14 Hadjadj, J., Yatim, N., Barnabei, L., Corneau, A., Boussier, J., Smith, N., Pere, H., Charbit, B., Bondet, V., Chenevier-Gobeaux, C., Breillat, P., Carlier, N., Gauzit, R., Morbieu, C., Pene, F., Marin, N., Roche, N., Szwebel, T. A., Merkling, S. H., Treluyer, J. M., Veyer, D., Mouthon, L., Blanc, C., Tharaux, P. L., Rozenberg, F., Fischer, A., Duffy, D., Rieux-Laucat, F., Kerneis, S. & Terrier, B. Impaired type I interferon activity and inflammatory responses in severe COVID-19 patients. *Science* 369, 718-724, doi:10.1126/science.abc6027 (2020).

15 Xu, Z., Shi, L., Wang, Y., Zhang, J., Huang, L., Zhang, C., Liu, S., Zhao, P., Liu, H., Zhu, L., Tai, Y., Bai, C., Gao, T., Song, J., Xia, P., Dong, J., Zhao, J. & Wang, F. S. Pathological findings of COVID-19 associated with acute respiratory distress syndrome. *Lancet Respir Med* 8, 420-422, doi:10.1016/S2213-2600(20)30076-X (2020).

16 De Biasi, S., Meschiari, M., Gibellini, L., Bellinazzi, 539 C., Borella, R., Fidanza, L., Gozzi, L., Iannone, A., Lo Tartaro, D., Mattioli, M., Paolini, A., Menozzi, M., Milic, J., Franceschi, G., Fantini, R., Tonelli, R., Sita, M., Sarti, M., Trenti, T., Brugioni, L., Cicchetti, L., Facchinetti, F., Pietrangelo, A., Clini, E., Girardis, M., Guaraldi, G., Mussini, C. & Cossarizza, A. Marked T cell activation, senescence, exhaustion and skewing towards TH17 in patients with COVID-19 pneumonia. *Nat Commun* 11, 3434, doi:10.1038/s41467-020-17292-4 (2020).

17 Bourgoin, P., Biechele, G., Ait Belkacem, I., Morange, P. E. & Malergue, F. Role of the interferons in CD64 and CD169 expressions in whole blood: Relevance in the balance between viral- or bacterial-oriented immune responses. *Immun Inflamm Dis* 8, 106-123, doi:10.1002/iid3.289 (2020).

18 Lajaunias, F., Dayer, J. M. & Chizzolini, C. Constitutive repressor activity of CD33 on human monocytes requires sialic acid recognition and phosphoinositide 3-kinase-mediated intracellular signaling. *Eur J Immunol* 35, 243-251, doi:10.1002/eji.200425273 (2005).

19 Lubbers, J., Rodriguez, E. & van Kooyk, Y. Modulation of Immune Tolerance via Siglec-Sialic Acid Interactions. *Front Immunol* 9, 2807, doi:10.3389/fimmu.2018.02807 (2018).

20 Marini, O., Costa, S., Bevilacqua, D., Calzetti, F., Tamassia, N., Spina, C., De Sabata, D., Tinazzi, E., Lunardi, C., Scupoli, M. T., Cavallini, C., Zoratti, E., Tinazzi, I., Marchetta, A., Vassanelli, A., Cantini, M., Gandini, G., Ruzzenente, A., Guglielmi, A., Missale, F., Vermi, W., Tecchio, C., Cassatella, M. A. & Scapini, P. Mature CD10(+) and immature CD10(−) neutrophils present in G-CSF-treated donors display opposite effects on T cells. *Blood* 129, 1343-1356, doi:10.1182/blood-2016-04-713206 (2017).

21 Evrard, M., Kwok, I. W. H., Chong, S. Z., Teng, K. W. W., Becht, E., Chen, J., Sieow, J. L., Penny, H. L., Ching, G. C., Devi, S., Adrover, J. M., Li, J. L. Y., Liong, K. H., Tan, L., Poon, Z., Foo, S., Chua, J. W., Su, I. H., Balabanian, K., Bachelerie, F., Biswas, S. K., Larbi, A., Hwang, W. Y. K., Madan, V., Koeffler, H. P., Wong, S. C., Newell, E. W., Hidalgo, A., Ginhoux, F. & Ng, L. G. Developmental Analysis of Bone Marrow Neutrophils Reveals Populations Specialized in Expansion, Trafficking, and Effector Functions. *Immunity* 48, 364-379 e368, doi:10.1016/j.immuni.2018.02.002 (2018).

22 Ng, L. G., Ostuni, R. & Hidalgo, A. Heterogeneity of neutrophils. *Nat Rev Immunol* 19, 255-265, doi:10.1038/s41577-019-0141-8 (2019).

23 Young, B. E., Ong, S. W. X., Kalimuddin, S., Low, J. G., Tan, S. Y., Loh, J., Ng, O. T., Marimuthu, K., Ang, L. W., Mak, T. M., Lau, S. K., Anderson, D. E., Chan, K. S., Tan, T. Y., Ng, T. Y., Cui, L., Said, Z., Kurupatham, L., Chen, M. I., Chan, M., Vasoo, S., Wang, L. F., Tan, B. H., Lin, R. T. P., Lee, V. J. M., Leo, Y. S., Lye, D. C. & Singapore Novel Coronavirus Outbreak Research, T. Epidemiologic Features and Clinical Course of Patients Infected With SARS-CoV-2 in Singapore. *JAMA*, doi:10.1001/jama.2020.3204 (2020).

24 Young, B. E. a. O., Sean Wei Xiang and Ng, Lisa F P and Anderson, Danielle E. and Chia, Wan Ni and Chia, Po Ying and Ang, Li Wei and Mak, Tze-Minn and Kalimuddin, Shirin and Chai, Louis Yi Ann and Pada, Surinder and Tan, Seow Yen and Sun, Louisa and Parthasarathy, Purnima and Fong, Siew-Wai and Chan, Yi-Hao and Tan, Chee Wah and Lee, Bernett and Rotzschke, Olaf and Ding, Ying and Tambyah, Paul and Low, Jenny G H and Cui, Lin and Barkham, Timothy and Lin, Raymond Tzer Pin and Leo, Yee-Sin and Renia, Laurent and Wang, Lin-Fa and Lye, David Chien and Team, Singapore 2019 Novel Coronavirus Outbreak Research. Immunological and Viral Correlates of COVID-19 Disease Severity: A Prospective Cohort Study of the First 100 Patients in Singapore (Apr. 15, 2020). Available at SSRN: https://ssrn.com/abstract=3576846 orhttp://dx.doi.org/10.2139/ssrn.3576846 (2020).

25 Cossarizza, A., De Biasi, S., Guaraldi, G., Girardis, M., Mussini, C. & (MoCol9)#, M. C.-W. G.SARS-CoV-2, the Virus that Causes COVID-19: Cytometry and the New Challenge for Global Health. *Cytometry A* 97, 340-343, doi:10.1002/cyto.a.24002 (2020).

26 Liu, J., Li, S., Liu, J., Liang, B., Wang, X., Wang, H., Li, W., Tong, Q., Yi, J., Zhao, L., Xiong, L., Guo, C., Tian, J., Luo, J., Yao, J., Pang, R., Shen, H., Peng, C., Liu, T., Zhang, Q., Wu, J., Xu, L., Lu, S., Wang, B., Weng, Z., Han, C., Zhu, H., Zhou, R., Zhou, H., Chen, X., Ye, P., Zhu, B., Wang, L., Zhou, W., He, S., He, Y., Jie, S., Wei, P., Zhang, J., Lu, Y., Wang, W., Zhang, L., Li, L., Zhou, F., Wang, J., Dittmer, U., Lu, M., Hu, Y., Yang, D. & Zheng, X. Longitudinal characteristics of lymphocyte responses and cytokine profiles in the peripheral blood of SARS-CoV-2 infected patients. *EBioMedicine* 55, 102763, doi:10.1016/j.ebiom.2020.102763 (2020).

27 Lagunas-Rangel, F. A. Neutrophil-to-lymphocyte ratio and lymphocyte-to-C-reactive protein ratio in patients with severe coronavirus disease 2019 (COVID-19): A meta-analysis. *J Med Virol*, doi:10.1002/jmv.25819 (2020).

28 Zini, G., Bellesi, S., Ramundo, F. & d'Onofrio, G. Morphological a 599 nomalies of circulating blood cells in COVID-19. *Am J Hematol*, doi:10.1002/ajh.25824 (2020).

29 Sanchez-Cerrillo, I., Landete, P., Aldave, B., Sanchez-Alonso, S., Sanchez-Azofra, A., Marcos-Jimenez, A., Avalos, E., Alcaraz-Serna, A., de Los Santos, I., Mateu-Albero, T., Esparcia, L., Lopez-Sanz, C., Martinez-Fleta, P., Gabrie, L., Del Campo Guerola, L., de la Fuente, H., Calzada, M. J., Gonzalez-Alvaro, I., Alfranca, A., Sanchez-Madrid, F., Munoz-Calleja, C., Soriano, J. B., Ancochea, J. & Martin-Gayo, E. COVID-19 severity associates with pulmonary redistribution of CD1c+DC and inflammatory transitional and nonclassical monocytes. *J Clin Invest*, 2020.2005.2013.20100925, doi:10.1172/JC1140335 (2020).

30 Yao, X. H., Li, T. Y., He, Z. C., Ping, Y. F., Liu, H. W., Yu, S. C., Mou, H. M., Wang, L. H., Zhang, H. R., Fu, W. J., Luo, T., Liu, F., Guo, Q. N., Chen, C., Xiao, H. L., Guo, H. T., Lin, S., Xiang, D. F., Shi, Y., Pan, G. Q., Li, Q. R., Huang, X., Cui, Y., Liu, X. Z., Tang, W., Pan, P. F., Huang, X. Q., Ding, Y. Q. & Bian, X. W. [A pathological report of three COVID-19 cases by minimal invasive autopsies]. *Zhonghua Bing LiXue Za Zhi* 49, 411-417, doi:10.3760/cma.j.cn112151-20200312-00193 (2020).

31 Barnes, B. J., Adrover, J. M., Baxter-Stoltzfus, A., Borczuk, A., Cools-Lartigue, J., Crawford, J. M., Dassler-Plenker, J., Guerci, P., Huynh, C., Knight, J. S., Loda, M., Looney, M. R., McAllister, F., Rayes, R., Renaud, S., Rousseau, S., Salvatore, S., Schwartz, R. E., Spicer, J. D., Yost, C. C., Weber, A., Zuo, Y. & Egeblad, M. Targeting potential drivers of COVID-19: Neutrophil extracellular traps. *J Exp Med* 217, doi:10.1084/jem.20200652 (2020).

32 Hidalgo, A., Chilvers, E. R., Summers, C. & Koenderman, L. The Neutrophil Life Cycle. *Trends Immunol* 40, 584-597, doi:10.1016/j.it.2019.04.013 (2019).

33 Morrissey, S. M., Geller, A. E., Hu, X., Tieri, D., Cooke, E. A., Ding, C., Woeste, M., Zhange, H.-g., Cavallazi, R., Clifford, S. P., Chen, J., Kong, M., Watson, C. T., Huang, J. & Yan, J. Emergence of Low-density Inflammatory Neutrophils Correlates with Hypercoagulable State and Disease Severity in COVID-19 Patients. Preprint at https://www.medrxiv.org/content/medrxiv/early/2020/05/26/2020.05.22.20106724.full.pdf, 2020.2005.2022.20106724, doi:10.1101/2020.05.22.20106724 (2020).

34 Schulte-Schrepping, J., Reusch, N., Paclik, D., Baßler, K., Schlickeiser, S., Zhang, B., Kramer, B., Krammer, T., Brumhard, S., Bonaguro, L., De Domenico, E., Wendisch, D., Grasshoff, M., Kapellos, T. S., Beckstette, M., Pecht, T., Saglam, A., Dietrich, O., Mei, H. E., Schulz, A. R., Conrad, C., Kunkel, D., Vafadarnejad, E., Xu, C.-J., Horne, A., Herbert, M., Drews, A., Thibeault, C., Pfeiffer, M., Hippenstiel, S., Hocke, A., Müller-Redetzky, H., Heim, K.-M., Machleidt, F., Uhrig, A., Bosquillon de Jarcy, L., Jürgens, L., Stegemann, M., Glösenkamp, C. R., Volk, H.-D., Goffinet, C., Landthaler, M., Wyler, E., Georg, P., Schneider, M., Dang-Heine, C., Neuwinger, N., Kappert, K., Tauber, R., Corman, V., Raabe, J., Kaiser, K. M., Vinh, M. T., Rieke, G., Meisel, C., Ulas, T., Becker, M., Geffers, R., Witzenrath, M., Drosten, C., Suttorp, N., von Kalle, C., Kurth, F., Händler, K., Schultze, J. L., Aschenbrenner, A. C., Li, Y., Nattermann, J., Sawitzki, B., Saliba, A.-E. & Sander, L. E. Severe COVID-19 is marked by a dysregulated myeloid cell compartment. *Cell*, doi:https://doi.org/10.1016/j.cell.2020.08.001 (2020).

35 Silvin, A., Chapuis, N., Dunsmore, G., Goubet, A.-G., Dubuisson, A., Derosa, L., Almire, C., Hénon, C., Kosmider, O., Droin, N., Rameau, P., Catelain, C., Alfaro, A., Dussiau, C., Friedrich, C., Sourdeau, E., Marin, N., Szwebel, T.-A., Cantin, D., Mouthon, L., Borderie, D., Deloger, M., Bredel, D., Mouraud, S., Drubay, D., Andrieu, M., Lhonneur, A.-S., Saada, V., Stoclin, A., Willekens, C., Pommeret, F., Griscelli, F., Ng, L. G., Zhang, Z., Bost, P., Amit, I., Barlesi, F., Marabelle, A., Pène, F., Gachot, B., Andre, F., Zitvogel, L., Ginhoux, F., Fontenay, M. & Solary, E. Elevated calprotectin and abnormal myeloid cell subsets discriminate severe from mild COVID-19. *Cell*, doi:https://doi.org/10.1016/j.cell.2020.08.002 (2020).

36 Seebach, J. D., Morant, R., Ruegg, R., Seifert, B. & Fehr, J. The diagnostic value of the neutrophil left shift in predicting inflammatory and infectious disease. *Am J Clin Pathol* 107, 582-591, doi:10.1093/ajcp/107.5.582 (1997).

37 Carmona-Rivera, C. & Kaplan, M. J. Low-density granulocytes: a distinct class of neutrophils in systemic autoimmunity. *Semin Immunopathol* 35, 455-463, doi:10.1007/s00281-013-0375-7 (2013).

38 Silvestre-Roig, C., Fridlender, Z. G., Glogauer, M. & Scapini, P. Neutrophil Diversity in Health and Disease. *Trends Immunol* 40, 565-583, doi:10.1016/j.it.2019.04.012 (2019).

39 Mortaz, E., Alipoor, S. D., Adcock, I. M., Mumby, S. & Koenderman, L. Update on Neutrophil Function in Severe Inflammation. *Front Immunol* 9, 2171, doi:10.3389/fimmu.2018.02171 (2018).

40 van Grinsven, E., Textor, J., Hustin, 659 L. S. P., Wolf, K., Koenderman, L. & Vrisekoop, N. Immature Neutrophils Released in Acute Inflammation Exhibit Efficient Migration despite Incomplete Segmentation of the Nucleus. *J Immunol* 202, 207-217, doi:10.4049/jimmunol.1801255 (2019).

41 Aziz, M., Fatima, R. & Assaly, R. Elevated Interleukin-6 and Severe COVID-19: A Meta-Analysis. *J Med Virol*, doi:10.1002/jmv.25948 (2020).

42 Yang, Y., Shen, C., Li, J., Yuan, J., Wei, J., Huang, F., Wang, F., Li, G., Li, Y., Xing, L., Peng, L., Yang, M., Cao, M., Zheng, H., Wu, W., Zou, R., Li, D., Xu, Z., Wang, H., Zhang, M., Zhang, Z., Gao, G. F., Jiang, C., Liu, L. & Liu, Y. Plasma IP-10 and MCP-3 levels are highly associated with disease severity and predict the progression of COVID-19. *J Allergy Clin Immunol*, doi:10.1016/j.jaci.2020.04.027 (2020).

43 Wen, W., Su, W., Tang, H., Le, W., Zhang, X., Zheng, Y., Liu, X., Xie, L., Li, J., Ye, J., Dong, L., Cui, X., Miao, Y., Wang, D., Dong, J., Xiao, C., Chen, W. & Wang, H. Immune cell profiling of COVID-19 patients in the recovery stage by single-cell sequencing. *Cell Discov* 6, 31, doi:10.1038/s41421-020-0168-9 (2020).

44 Zhang, D., Guo, R., Lei, L., Liu, H., Wang, Y., Wang, Y., Dai, T., Zhang, T., Lai, Y., Wang, J., Liu, Z., He, A., O'Dwyer, M. & Hu, J. COVID-19 infection induces readily detectable morphological and inflammation-related phenotypic changes in peripheral blood monocytes, the severity of which correlate with patient outcome. Preprint at https://www.medrxiv.org/content/medrxiv/early/2020/03/26/2020.03.24.20042655.full.pdf, 2020.2003.2024.20042655, doi:10.1101/2020.03.24.20042655 (2020).

45 Zimmermann, M., Aguilera, F. B., Castellucci, M., Rossato, M., Costa, S., Lunardi, C., Ostuni, R., Girolomoni, G., Natoli, G., Bazzoni, F., Tamassia, N. & Cassatella, M. A. Chromatin remodelling and autocrine TNFalpha are required for optimal interleukin-6 expression in activated human neutrophils. *Nat Commun* 6, 6061, doi:10.1038/ncomms7061 (2015).

46 Cervantes, J. L., Weinerman, B., Basole, C. & Salazar, J. C. TLR8: the forgotten relative revindicated. *Cell Mol Immunol* 9, 434-438, doi:10.1038/cmi.2012.38 (2012).

47 Linden, A., Laan, M. & Anderson, G. P. Neutrophils, interleukin-17A and lung disease. *Eur Respir J* 25, 159-172, doi:10.1183/09031936.04.00032904 (2005).

48 Maggi, L., Santarlasci, V., Capone, M., Peired, A., Frosali, F., Crome, S. Q., Querci, V., Fambrini, M., Liotta, F., Levings, M. K., Maggi, E., Cosmi, L., Romagnani, S. & Annunziato, F. CD161 is a marker of all human IL-17-producing T-cell subsets and is induced by RORC. *Eur J Immunol* 40, 2174-2181, doi:10.1002/eji.200940257 (2010).

49 Pacha, O., Sallman, M. A. & Evans, S. E. COVID-19: a case for inhibiting IL-17? *Nat Rev Immunol*, doi:10.1038/s41577-020-0328-z (2020).

50 Megna, M., Napolitano, M. & Fabbrocini, G. May IL-17 have a role in COVID-19 infection? *Med Hypotheses* 140, 109749, doi:10.1016/j.mehy.2020.109749 (2020).

51 Wu, D. & Yang, X. O. TH17 responses in cytokine storm of COVID-19: An emerging target of JAK2 inhibitor Fedratinib. *J Microbiol Immunol Infect*, doi:10.1016/j.jmii.2020.03.005 (2020).

52 Tanaka, Y., Morita, C. T., Tanaka, Y., Nieves, E., Brenner, M. B. & Bloom, B. R. Natural and synthetic non-peptide antigens recognized by human gamma delta T cells. *Nature* 375, 155-158, doi:10.1038/375155a0 (1995).

53 Poupot, M. & Fournie, J. J. Non-peptide antigens activating human Vgamma9/Vdelta2 T lymphocytes. *Immunol Lett* 95, 129-138, doi:10.1016/j.imlet.2004.06.013 (2004).

54 Laggner, U., Di Meglio, P., Perera, G. K., Hundhausen, C., Lacy, K. E., Ali, N., Smith, C. H., Hayday, A. C., Nickoloff, B. J. & Nestle, F. O. Identification of a novel proinflammatory human skin-homing Vgamma9Vdelta2 T cell subset with a potential role in psoriasis. *J Immunol* 187, 2783-2793, doi:10.4049/jimmunol.1100804 (2011).

55 McCarthy, N. E., Hedin, C. R., Sanders, T. J., Amon, P., Hoti, I., Ayada, I., Baji, V., Giles, E. M., Wildemann, M., Bashir, Z., Whelan, K., Sanderson, I., Lindsay, J. O. & Stagg, A. J. Azathioprine therapy selectively ablates human Vdelta2(+) T cells in Crohn's disease. *J Clin Invest* 125, 3215-3225, doi:10.1172/JCI80840 (2015).

56 Urboniene, D., Babusyte, A., Lotvall, J., Sakalauskas, R. & Sitkauskiene, B. Distribution of gammadelta and other T-lymphocyte subsets in patients with chronic obstructive pulmonary disease and asthma. *Respir Med* 107, 413-423, doi:10.1016/j.rmed.2012.11.012 (2013).

57 Sant, S., Jenkins, M. R., Dash, P., Watson, K. A., Wang, Z., Pizzolla, A., Koutsakos, M., Nguyen, T. H., Lappas, M., Crowe, J., Loudovaris, T., Mannering, S. I., Westall, G. P., Kotsimbos, T. C., Cheng, A. C., Wakim, L., Doherty, P. C., Thomas, P. G., Loh, L. & Kedzierska, K. Human gammadelta T-cell receptor repertoire is shaped 58 Bonneville, M., O'Brien, R. L. & Born, W. K. Gammadelta T cell effector functions: a blend of innate programming and acquired plasticity. *Nat Rev Immunol* 10, 467-478, doi:10.1038/nri2781 (2010).

59 Davey, M. S., Lin, C. Y., Roberts, G. W., Heuston, S., Brown, A. C., Chess, J. A., Toleman, M. A., Gahan, C. G., Hill, C., Parish, T., Williams, J. D., Davies, S. J., Johnson, D. W., Topley, N., Moser, B. & Eberl, M. Human neutrophil clearance of bacterial pathogens triggers antimicrobial gammadelta T cell responses in early infection. *PLoS Pathog* 7, e1002040, doi:10.1371/journal.ppat.1002040 (2011).

60 Fazio, J., Kalyan, S., Wesch, D. & Kabelitz, D. Inhibition of human gammadelta T cell proliferation and effector functions by neutrophil serine proteases. *Scand J Immunol* 80, 381-389, doi:10.1111/sji.12221 (2014).

61 Sabbione, F., Gabelloni, M. L., Ernst, G., Gori, M. S., Salamone, G., Oleastro, M., Trevani, A., Geffner, J. & Jancic, C. C. Neutrophils suppress gammadelta T-cell function. *Eur J Immunol* 44, 819-830, doi:10.1002/eji.201343664 (2014).

62 Caccamo, N., Meraviglia, S., Ferlazzo, V., Angelini, D., Borsellino, G., Poccia, F., Battistini, L., Dieli, F. & Salerno, A. Differential requirements for antigen or homeostatic cytokines for proliferation and differentiation of human Vgamma9Vdelta2 naive, memory and effector T cell subsets. *Eur J Immunol* 35, 1764-1772, doi: 10.1002/eji.200525983 (2005).

63 Tan, C. T., Wistuba-Hamprecht, K., Xu, W., Nyunt, M. S., Vasudev, A., Lee, B. T., Pawelec, G., Puan, K. J., Rotzschke, O., Ng, T. P. & Larbi, A. Vdelta2+ and alpha/ss T cells show divergent trajectories during human aging. *Oncotarget* 7, 44906-44918, doi:10.18632/oncotarget.10096 (2016).

64 Vasudev, A., Ying, C. T., Ayyadhury, S., Puan, K. J., Andiappan, A. K., Nyunt, M. S., Shadan, N. B., Mustafa, S., Low, I., Rotzschke, O., Fulop, T., Ng, T. P. & Larbi, A. gamma/delta T cell subsets in human aging using the classical alpha/beta T cell model. *J Leukoc Biol* 96, 647-655, doi:10.1189/jlb.5A1213-650RR (2014).

65 Michishita, Y., Hirokawa, M., Guo, Y. M., Abe, Y., Liu, J., Ubukawa, K., Fujishima, N., Fujishima, M., Yoshioka, T., Kameoka, Y., Saito, H., Tagawa, H., Takahashi, N. & Sawada, K. Age-associated alteration of gammadelta T-cell repertoire and different profiles of activation induced death of Vdelta1 and Vdelta2 T cells. *Int J Hematol* 94, 230-240, doi:10.1007/si2185-011-0907-7 (2011).

66 Franceschi, C., Bonafe, M., Valensin, S., Olivieri, F., De Luca, M., Ottaviani, E. & De Benedictis, G. Inflammaging. An evolutionary perspective on immunosenescence. *Ann N Y Acad Sci* 908, 244-254, doi:10.1111/j.1749-6632.2000.tb06651.x (2000).

67 Fulop, T., Larbi, A., Dupuis, G., Le Page, A., Frost, E. H., Cohen, A. A., Witkowski, J. M. & Franceschi, C. Immunosenescence and Inflamm-Aging As Two Sides of the Same Coin: Friends or Foes? *Front Immunol* 8, 1960, doi:10.3389/fimmu.2017.01960 (2017).

68 Xu, W., Lau, Z. W. X., Fulop, T. & Larbi, A. The Aging of gammadelta T Cells. *Cells* 9, doi:10.3390/cells9051181 (2020).

69 Bonafe, M., Prattichizzo, F., Giuliani, A., Storci, G., Sabbatinelli, J. & Olivieri, F. Inflamm aging: Why older men are the most susceptible to SARS-CoV-2 complicated outcomes. *Cytokine Growth Factor Rev* 53, 33-37, doi:10.1016/j.cytogfr.2020.04.005 (2020).

70 Liu, Y., Mao, B., Liang, S., Yang, J. W., Lu, H. W., Chai, Y. H., Wang, L., Zhang, L., Li, Q. H., Zhao, L., He, Y., Gu, X. L., Ji, X. B., Li, L., Jie, Z. J., Li, Q., Li, X. Y., Lu, H. Z., Zhang, W. H., Song, Y. L., Qu, J. M., Xu, J. F. & Shanghai Clinical Treatment Experts Group for, C. Association between age and clinical characteristics and outcomes of COVID-19. *Eur Respir J* 55, doi:10.1183/13993003.01112-2020 (2020).

71 Li, J., Huang, D. Q., Zou, B., Yang, H., Hui, W. Z., Rui, F., Yee, N. T. S., Liu, C., Nerurkar, S. N., Kai, J. C. Y., Teng, M. L. P., Li, X., Zeng, H., Borghi, J. A., Henry, L., Cheung, R. & Nguyen, M. H. Epidemiology of COVID-19: A Systematic Review and Meta-analysis of Clinical Characteristics, Risk factors and Outcomes. *J Med Virol*, doi:10.1002/jmv.26424 (2020).

72 Vahidy, F. S., Nicolas, J. C., Meeks, J. R., Khan, O., Pan, A., Jones, S. L., Masud, F., Sostman, H. D., Phillips, R., Andrieni, J. D., Kash, B. A. & Nasir, K. Racial and ethnic disparities in SARS-CoV-2 pandemic: analysis of a COVID-19 observational registry for a diverse US metropolitan population. *BMJ Open* 10, e039849, doi: 10.1136/bmjopen-2020-039849 (2020).

73 Pung, R., Chiew, C. J., Young, B. E., Chin, S., 777 Chen, M. I., Clapham, H. E., Cook, A. R., Maurer-Stroh, S., Toh, M., Poh, C., Low, M., Lum, J., Koh, V. T. J., Mak, T. M., Cui, L., Lin, R., Heng, D., Leo, Y. S., Lye, D. C. & Lee, V. J. M. Investigation of three clusters of COVID-19 in Singapore: implications for surveillance and response measures. *Lancet* 395, 1039-1046, doi:10.1016/s0140-6736(20)30528-6 (2020).

74 Darnell, M. E. & Taylor, D. R. Evaluation of inactivation methods for severe acute respiratory syndrome coronavirus in noncellular blood products. *Transfusion* 46, 1770-1777, doi:10.1111/j.1537-2995.2006.00976.x (2006).

75 Chen, H., Lau, M. C., Wong, M. T., Newell, E. W., Poidinger, M. & Chen, J. Cytofkit: A Bioconductor Package for an Integrated Mass Cytometry Data Analysis Pipeline. *PLoS Comput Biol* 12, e1005112, doi:10.1371/journal.pcbi.1005112 (2016).

Applications

Embodiments of the methods disclosed herein provide a rapid and efficient care management of patients by identifying patients that may have a high or enhanced risk of developing severe infectious disease and/or inflammatory disease onset. Embodiments of the disclosed methods also seek to overcome the problems of identifying patients who may have an enhanced or increased risk of developing pneumonia and/or hypoxia symptoms of SAR-COV2.

Advantageously, immature neutrophils to VD2 T cell ratio shows very high sensitivity and specificity with pneumonia and hypoxia symptoms in SAR-CoV2-infected patients early after infection allowing for rapid and efficient care management of patients identified as high risk.

In some examples, the use of VD2 T-cells as the denominator of the ratio instead of CD8 T-cells may be used. In such examples, VD2 T-cells show a lower spread (standard deviation) as compared to CD8 T-cells in the different severity groups ( ), and decreases in the periphery with age. This advantageously allows the parameter to be automatically adjusted to the immunological age of the patient.

Even more advantageously, the technology is compatible with most standard colour cytometers available in hospitals and harnesses their rapid diagnostic capacities to perform assessment of the said parameters as a prognostic marker for infected patients (such as SAR-CoV2-infected patients). In addition, the methods as disclosed herein may be performed using antibodies and/or counting beads known in the art. Advantageously, antibodies and counting beads are easily packaged premixed and lyophilized allowing easy shipment and long shelf life. Usage of counting beads also advantageously allows for the comparison of the number of beads acquired to the theoretical number of beads in the mix. This allows correction of the acquired and detected cell population counts to the theoretical counts in the fixed volume of blood mixed with the full stain mix.

The present disclosure also provides for the possibility of having a standardized identification of immature neutrophil population using the combination of the highly specific markers in a kit (for example, as exemplified in Example 2, the full stain mix and/or the FMO mix).

The invention claimed is:

1. A method of evaluating risk of severe outcome of an infectious disease and/or an inflammatory disease in a patient, the method comprising:
    detecting a number of immune cells for each of VD2 (γδ2) T cells, CD8 T cells, and immature neutrophils in a blood sample obtained from the patient with flow cytometry and/or immunostaining panel markers,
    measuring the number of immune cells comprising VD2 (γδ2) T cells, CD8 T cells, and immature neutrophils in the blood sample,
    wherein the number of immature neutrophils is determined by measuring a number of cells having a cell surface phenotype $CD3^-$ $CD66b/CD15^+$ $CD16^{intermediate/-}$ $CD10^-$,
    wherein the number of VD2 T cells is determined by measuring the number of cells having a cell surface phenotype CD3+ VD2+,
    wherein the number of CD8 T cells is determined by measuring the number of cells having a surface phenotype CD3+CD8+, and
    evaluating the patient to have a severe outcome of the infectious disease and/or the inflammatory disease by calculating a ratio of immature neutrophils to VD2 T cell and/or a ratio of immature neutrophils to CD8 T cell, and
    wherein the patient is evaluated to have an enhanced risk of severe infectious disease and/or inflammatory disease outcome when:
    (i) the ratio of immature neutrophils to VD2 T cell in the blood sample is at least 2:1, and/or
    (ii) the ratio of immature neutrophils to CD8 T cell in the blood sample is at least 0.5:1, and
    administering a care treatment for severe infectious disease and/or inflammatory disease to the patient determined to have an enhanced risk of severe infectious disease and/or inflammatory disease outcome.

2. The method according to claim 1, wherein the infectious disease is a coronavirus infection.

3. The method according to claim 1, wherein the severe infectious disease outcome is pneumonia and/or hypoxia.

4. The method according to claim 1, wherein the method further comprises measuring the number of one or more cells selected from the group consisting of CD4+ T cells, mucosal-associated invariant T cells (MAIT), VD1 (γδ1) T cells, plasmacytoid dendritic cells (pDCs), dendritic cells (DCs), classical and intermediate monocytes.

5. The method according to claim 4, wherein a reduction in the number of the one or more cells as compared to a control indicates an enhanced risk of severe infectious disease and/or inflammatory disease outcome, and the control is obtained from a healthy subject having no coronavirus infection and/or severe infectious disease outcome.

6. The method according to claim 4, wherein the blood sample is obtained at a first time point and a second time point, and a reduction in the number of the one or more cells at the second time point as compared to first time point indicates an enhanced risk of severe infectious disease and/or inflammatory disease outcome.

7. The method according to claim 1, wherein the method further comprises measuring an expression of one or more myeloid activation markers on monocytes.

8. The method according to claim 7, wherein a reduction in an expression of the one or more myeloid activation markers on monocytes as compared to a control indicates an enhanced risk of severe infectious disease and/or inflammatory disease outcome, and the control is obtained from a healthy subject having no coronavirus infection and/or severe infectious disease outcome.

9. The method according to claim 7, wherein the blood sample is obtained at a first time point and a second time point, and a reduction in an expression of the one or more myeloid activation markers on monocytes in the second time point as compared to the first time point indicates an enhanced risk of severe infectious disease and/or inflammatory disease outcome.

10. The method according to claim 1, wherein the number of immune cells are determined by measuring a number of cells expressing markers comprising CD66b/CD15, CD16, CD10, CD3, VD2, and CD8.

11. The method according to claim 1, wherein the number of VD2 T cells is determined by measuring the number of cells having the cell surface phenotype CD45+ CD3+ VD2+.

12. The method according to claim 1, wherein the method further comprises determining the absolute number of immune cells measured in the blood sample.

13. The method according to claim 1, wherein the blood sample is obtained from the patient between 1 to 10 days post-illness onset (pio) and/or between 1 to 40 days post-treatment.

14. The method according to claim 1, wherein the infectious disease is a Severe Acute Respiratory Syndrome coronavirus 2 (SARS-COV-2) infection.

15. The method according to claim 1, wherein the patient is human.

16. The method according to claim 1, wherein the markers are detected with antibodies coupled to fluorophores.

* * * * *